US012290515B2

(12) United States Patent
Chain et al.

(10) Patent No.: US 12,290,515 B2
(45) Date of Patent: *May 6, 2025

(54) CO-CRYSTALS

(71) Applicant: CereSpir Incorporated, New York, NY (US)

(72) Inventors: Daniel G. Chain, New York, NY (US); Ronald Mueller, Northbrook, IL (US)

(73) Assignee: CereSpir Incorporated, New York, NY (US)

( * ) Notice: Subject to any disclaimer, the term of this patent is extended or adjusted under 35 U.S.C. 154(b) by 12 days.

This patent is subject to a terminal disclaimer.

(21) Appl. No.: 18/210,217

(22) Filed: Jun. 15, 2023

(65) Prior Publication Data
US 2023/0321070 A1   Oct. 12, 2023

Related U.S. Application Data

(63) Continuation of application No. 17/973,297, filed on Oct. 25, 2022, now Pat. No. 11,717,516, which is a continuation of application No. 17/897,388, filed on Aug. 29, 2022.

(60) Provisional application No. 63/238,928, filed on Aug. 31, 2021.

(51) Int. Cl.
*A61K 31/455* (2006.01)
*A61K 31/192* (2006.01)
*A61P 25/28* (2006.01)

(52) U.S. Cl.
CPC .......... *A61K 31/455* (2013.01); *A61K 31/192* (2013.01)

(58) Field of Classification Search
CPC ...... A61K 31/455; A61K 31/192; A61P 25/28
See application file for complete search history.

(56) References Cited

U.S. PATENT DOCUMENTS

| | | | |
|---|---|---|---|
| 7,662,995 B2 | 2/2010 | Raveglia et al. | |
| 8,022,250 B2 | 9/2011 | Raveglia et al. | |
| 8,076,505 B2 | 12/2011 | Folleas et al. | |
| 8,314,268 B2 | 11/2012 | Raveglia et al. | |
| 9,056,818 B2 | 6/2015 | Pivetti et al. | |
| 9,290,428 B2 | 3/2016 | Verzini et al. | |
| 9,592,210 B2 | 3/2017 | Imbimbo | |
| 11,717,516 B2 | 8/2023 | Chain | |
| 2006/0134198 A1 | 6/2006 | Tawa et al. | |
| 2015/0119428 A1 | 4/2015 | Holland et al. | |
| 2015/0209306 A1 | 7/2015 | Bredesen et al. | |
| 2015/0320706 A1 | 11/2015 | Imbimbo et al. | |
| 2016/0136136 A1 | 5/2016 | Cohen et al. | |

OTHER PUBLICATIONS

Kumar, Devendra et al. "*Secretase Inhibitors For the Treatment of Alzheimer's Disease: Long Road Ahead*". European Journal of Medicinal Chemistry, vol. 148, pp. 436-452, (2018).
Loconte, Valentina et al. "*Structure-Activity Relationships of Flurbiprofen Analogues as Stabilizers of the Amyloidogenic Protein Transthyretin*". Journal of Structural Biology, vol. 208, pp. 165-173, (2019).
Dhondale, M.R et al. "*Co-Crystallization Approach to Enhance the Stability of Moisture-Sensitive Drugs*". Pharmaceutcs, vol. 189,No. 15, (2023).
Zhi-Wei Zhang, et al., "The APP intracellular domain promotes LRRK2 expression to enable feed-for-ward neurodegenerative mechanisms in Parkinson's disease", Science Signaling, vol. 15, Issue 748, Aug. 23, 2022.
International Search Report and Written Opinion issued on Oct. 28, 2022, in connection with corresponding International Application No. PCT/US2022/041823.
Laszlo Fabian, et al., "Cocrystals of Fenamic Acids with Nicotinamide", Crystal Growth and Design, vol. 11, pp. 3552-3528, 2011.
Ala' Salem, et al., "Reliability of the Hansen solubility parameters as co-crystals formations prediction tool", International Journal of Pharmaceutics, 558, pp. 319-327, 2019.
Chow, S.F et al. "*Simultaneously Improving the Mechanical Properties, Dissolution Performance, and Hygroscopicity of Ibuprofen and Flurbiprofen by Cocrystallization with Nicotinamide*". Pharm Res, vol. 29, pp. 1854-1865, (2012).

*Primary Examiner* — Irina Neagu
(74) *Attorney, Agent, or Firm* — Davidson Kappel LLC

(57) ABSTRACT

Co-crystals of itanapraced; methods of preparation of the co-crystals; uses of the co-crystals as APIs; formulations containing the co-crystals; uses of the co-crystals and formulations for prevention and treatment of neurodegeneration disorders, infections, dementias, inflammation, and injuries; and methods of prevention and treatment of neurodegeneration disorders, infections, dementias, inflammation, and injuries are described.

10 Claims, 18 Drawing Sheets

CO-CRYSTALS

This application is a continuation of U.S. patent application Ser. No. 17/973,297, filed Oct. 25, 2022, which is a continuation of U.S. patent application Ser. No. 17/897,388, filed Aug. 29, 2022, which claims the benefit of U.S. Provisional Application No. 63/238,928, filed on Aug. 31, 2021, the disclosures of which are hereby incorporated by reference herein.

FIELD OF THE INVENTION

The invention generally relates to co-crystals; methods of preparation of co-crystals; uses of co-crystals as active pharmaceutical ingredients (APIs); dosage forms comprising co-crystals; methods of preparation of dosage forms; uses of the co-crystals and the dosage forms comprising co-crystals for prevention and treatment of neurodegeneration disorders, infections, dementias, inflammation, and injuries; and methods of prevention and treatment of neurodegeneration disorders, infections, dementias, inflammation, and injuries.

BACKGROUND OF THE INVENTION

An active pharmaceutical ingredient (API) is an ingredient in a pharmaceutical dosage form that is biologically active (i.e., a drug). Traditionally, a free base, a salt, a solvate, a hydrate, or a polymorph of the ingredient was used as an API.

A salt is a chemical compound formed from the reaction of an acid with a base.

A solvate is a multicomponent crystalline solid molecular adduct formed by solvation (i.e., the combination of solvent molecules or ions with molecules of the solute). The solvate contains molecules or ions of the solute and molecules of solvent(s) in a crystal lattice structure.

A hydrate is a multicomponent crystalline solid molecular adduct formed by hydration (i.e., the combination of water molecules with molecules or ions of the solute). The hydrate contains molecules or ions of the solute and molecules of water incorporated in a crystal lattice structure.

Polymorphs are single-component crystalline forms that have different arrangements or conformations of molecules of one compound in a crystal lattice.

Unlike salts, solvates, hydrates, and polymorphs; co-crystals are crystalline materials comprising molecules of two or more different compounds in a fixed stoichiometric ratio in a crystal lattice. The molecules of two or more different compounds are not covalently bound and do not interact ionically. Rather, the molecules of two or more different compounds interact nonionically with each other in the co-crystals.

Co-crystals are distinguishable from salts, because the components of co-crystals interact nonionically rather than ionically.

Co-crystals are distinguishable from polymorphs, because co-crystals contain molecules of two or more different compounds rather than molecules of a single compound.

Co-crystals are distinguishable from solvates, because the second component of the co-crystal (a coformer) is not a solvent and typically is nonvolatile.

Co-crystals are distinguishable from hydrates, because the second component of the co-crystal (a coformer) is not water and typically is nonvolatile.

Co-crystals are also distinguishable from each of the compounds in their crystal lattice, because co-crystals have physico-chemical properties that are different from those of the compounds in their crystal lattice. For example, the melting point, solubility, bioavailability, hygroscopicity, stability, and/or permeability of the co-crystal may be different from the melting point, solubility, bioavailability, hygroscopicity, stability, permeability of the components of the co-crystal.

The amyloid precursor protein (APP) is a broadly expressed transmembrane protein. APP is expressed, for example, in neurons, astrocytes and microglia. APP expression and its metabolism changes under various neuropathological conditions, especially in response to oxidative stress.

Cleavage of APP by gamma and beta sectretases acting sequentially, generates a series of fragments including, e.g., amyloid β (AB) peptides and APP intracellular domain (AICD).

AICD is a transcriptional modulator that has been implicated in various physiological processes, including synaptic plasticity and cytoskeletal organization. However, under conditions of severe oxidative stress, AICD interacts with a transcriptional co-activator FOXO3a, to promote cell death. Additionally, AICD and FOXO3a have been shown to jointly control mitochondrial function by modulating PTEN induced putative kinase 1 (PINK1) transcription and to control the expression of Leucine Rich Repeat Kinase 2 (LRRK2). LRRK2 mutations adversely impair multiple physiological processes, including synaptic activity and plasticity, maintenance of normal dendritic spine morphology. Several lines of evidence indicate that overactive LRRK2 interferes with autophagic processes, including mitophagy. Based on these properties, inhibition of AICD activity is therefore anticipated to have beneficial effects in treatment of a number of diseases.

Although, Aβ accumulation has received the most attention, AICD which is produced concomitantly, is increasingly recognized as a likely major contributor to the pathogenesis of Alzheimer's disease (AD) and numerous other neurodegenerative disorders, e.g., Parkinson's disease (PD), Multiple Sclerosis (MS), juvenile neuronal ceroid lipofuscinosis (JNCL) (Batten disease type-3), age-related macular degeneration (AMD); Amylolateral sclerosis (ALS), mild cognitive impairment (MCI), neurologic injury (Traumatic Brain Injury (TBI)) and neurologic inflammation.

OBJECTS AND SUMMARY OF THE INVENTION

It is an object of the invention to provide a co-crystal comprising an ingredient that binds APP in the intracellular domain.

It is an object of the invention to provide a co-crystal comprising an ingredient that inhibits translocation of AICD to the nucleus.

It is an object of the invention to provide a co-crystal comprising and ingredient that modulates transcriptional activity of AICD.

It is an object of the invention to provide a co-crystal comprising an ingredient that is capable of microglial modulation.

It is an object of the invention to provide a co-crystal comprising an ingredient that is capable of inhibiting inflammation.

It is an object of the invention to provide a co-crystal comprising itanapraced (aka CSP-1103, formerly CHF5074) and a coformer, e.g., nicotinamide.

It is a further object of the invention to provide a co-crystal of itanapraced that is more water soluble than itanapraced.

It is an additional object of the invention to provide a co-crystal comprising itanapraced and a coformer, wherein the co-crystal is less hygroscopic than itanapraced.

It is another object of the present invention to provide a method for preventing, inhibiting, reducing, eliminating, protecting or delaying the onset of acute and chronic neurodegeneration disorders, mild cognitive impairment, dementias, neurologic injury, and neurologic inflammation.

It is another object of the present invention to overcome or ameliorate at least one of the disadvantages of the prior art, or to provide a useful alternative.

In accordance with the above objects and others, the invention is directed to a pharmaceutical formulation comprising a co-crystal, the co-crystal comprising a crystal lattice comprising molecules of an active ingredient and a coformer, the active ingredient interacting nonionically with the coformer in the crystal lattice, wherein the active ingredient includes a carboxylic acid moiety and the coformer is a nonvolatile heterocyclic organic compound, the active ingredient and coformer being associated only by non-ionic and noncovalent bonds, and wherein the coformer is not a solvent. A stoichiometric ratio of the active ingredient to the coformer may be from about 0:5:1.5 to about 1.5:0.5. The coformer may be included in an amount sufficient to provide an improvement in a physical property of the active ingredient, as compared to a physical property of the active ingredient without the coformer. The improved physical property may, e.g., be hygroscopicity. In certain embodiment, the active ingredient is a praced (e.g., itanapraced), and the coformer is a heterocyclic organic compound having a pyridinyl moiety. Heterocyclic organic compounds having a pyridinyl moiety include, e.g., nicotinamide, picolinamide, isonicotinamide, isonicotinic acid, and nicotinic acid.

The invention is further directed to a pharmaceutical formulation comprising a therapeutically effective amount of an active ingredient (in certain embodiments preferably an AICD inhibitor), the active ingredient being in a form of a co-crystal, the co-crystal comprising molecules of the active ingredient and a coformer in a crystal lattice, the active ingredient interacting nonionically with the coformer in the crystal lattice, wherein the active ingredient and the coformer are associated only by non-ionic and noncovalent bonds, and the coformer is nonvolatile and is not a solvent. The coformer may be included in an amount sufficient to provide an improvement in a physical property (e.g., hydroscopicity, solubility, etc.) and/or bioavailability and/or an rate of dissolution and/or shorter time to Cmax of the active ingredient, as compared to a physical property, bioavailability, rate of dissolution, and time to Cmax of the active ingredient without the coformer (i.e., without interacting nonionically and being associated with the coformer only by non-ionic and noncovalent bonds). Once the coformer dissociates from the active pharmaceutical ingredient, the active ingredient becomes available to provide a pharmacologic effect(s).

The invention is also directed to a pharmaceutical formulation comprising a therapeutically effective amount of an AICD inhibitor, the AICD inhibitor being in a form of a co-crystal, the co-crystal comprising a crystal lattice comprising molecules of the AICD inhibitor and a coformer, the AICD inhibitor interacting nonionically with the coformer in the crystal lattice, wherein the AICD inhibitor and the coformer are associated only by non-ionic and noncovalent bonds, and the coformer is nonvolatile and is not a solvent. The coformer may be included in an amount sufficient to provide an improvement in a physical property of the AICD inhibitor, as compared to a physical property of the AICD inhibitor without the coformer. Thus, in some embodiments, the coformer may be included in an amount sufficient to provide an improvement in hygroscopicity of the AICD inhibitor, as compared to hygroscopicity of the AICD inhibitor without the coformer.

The invention is also directed to a pharmaceutical formulation comprising a therapeutically effective amount of an AICD inhibitor, the AICD inhibitor being in a form of a co-crystal, the co-crystal comprising molecules of the AICD inhibitor and a coformer in a crystal lattice, the AICD inhibitor interacting nonionically with the coformer in the crystal lattice, wherein the AICD inhibitor and the coformer are associated only by non-ionic and noncovalent bonds, and wherein the coformer is nonvolatile, is not a solvent, and is included in an amount sufficient to provide an improvement in bioavailability and/or an rate of dissolution and/or shorter time to Cmax of the AICD inhibitor, as compared to bioavailability, rate of dissolution, and time to Cmax of the AICD inhibitor without the coformer. In certain embodiments, when the pharmaceutical formulation is administered to a human, the coformer is dissociatable from the AICD inhibitor. Once the coformer dissociates from the AICD inhibitor, the AICD inhibitor becomes available to provide a pharmacologic effect(s), including, e.g., bind the intracellular domain of APP, inhibit the transcriptional activity of APP intracellular domain (AICD). The AICD inhibitor may modulate transcriptional activity of AICD. Thus, in some of the embodiments, the AICD inhibitor may induce transcriptional activity of AICD. In other embodiments, the AICD inhibitor may inhibit transcriptional activity of AICD.

The invention is also directed to a pharmaceutical formulation comprising a therapeutically effective amount of an AICD inhibitor, the AICD inhibitor being in a form of a co-crystal, the co-crystal comprising molecules of the AICD inhibitor and a coformer in a crystal lattice, the AICD inhibitor interacting nonionically with the coformer in the crystal lattice, wherein the AICD inhibitor and the coformer are associated only by non-ionic and noncovalent bonds, and wherein the coformer is a nonvolatile organic compound, is not a solvent and is included in an amount sufficient to provide an improvement in a physical property (e.g., hydroscopicity, solubility, etc.) and/or bioavailability and/or an rate of dissolution and/or shorter time to Cmax of the AICD inhibitor, as compared to a physical property, bioavailability, rate of dissolution, and time to Cmax of the AICD inhibitor without the coformer (i.e., without interacting nonionically and being associated by non-ionic and noncovalent bonds with the coformer), such that when the pharmaceutical formulation is administered to a human, the coformer dissociates from the AICD inhibitor. In some of the embodiments, the AICD inhibitor is a praced, and the coformer is selected from a group consisting of nicotinamide, picolinamide, isonicotinamide, isonicotinic acid, and nicotinic acid. In some of these embodiments, the co-crystal comprises itanapraced and a coformer, wherein the coformer is nicotinamide and the co-crystal comprises an X-ray Powder Diffraction Pattern (XRPD) with specific peaks, expressed in 2θ produced from a Cu radiation source ($\lambda$=1.54 Å after Ni filtering), at about 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ. For example, the XPRD may be substantially the same as the X-ray Powder Diffraction Pattern (XRPD) shown in FIG. 3A. In some of these embodiments, a stoichiometric ratio of itanapraced to nicotinamide is from about 0:8:1.2 to about 1.2:0.8 (e.g., about 1:1). In some of these embodiments, a stoichiometric ratio of itanapraced to nicotinamide is about 1:1. In all of these embodiments, the pharmaceutical formulation may be less hygroscopic than itanapraced.

The invention is also directed to a pharmaceutical formulation comprising a therapeutically effective amount of an AICD inhibitor, the AICD inhibitor being in a form of a co-crystal, the co-crystal comprising molecules of the AICD inhibitor and a coformer in a crystal lattice, the AICD inhibitor interacting nonionically with the coformer in the crystal lattice, wherein the AICD inhibitor and the coformer are associated only by non-ionic and noncovalent bonds, the coformer is a nonvolatile organic compound, is not a solvent, and is associated with the AICD inhibitor only via the non-ionic and noncovalent bonds, and wherein the coformer is included in an amount sufficient to provide an improvement in a physical property and/or bioavailability and/or an rate of dissolution and/or shorter time to Cmax of the AICD inhibitor, as compared to a physical property, bioavailability, rate of dissolution, and time to Cmax of the AICD inhibitor without the coformer, wherein the AICD inhibitor is a praced, and the coformer is selected from a group consisting of nicotinamide, picolinamide, isonicotinamide, isonicotinic acid, and nicotinic acid.

The invention is also directed to a pharmaceutical formulation comprising a therapeutically effective amount of an AICD inhibitor, the AICD inhibitor being in a form of a co-crystal, the co-crystal comprising molecules of the AICD inhibitor and a coformer in a crystal lattice, the AICD inhibitor interacting nonionically with the coformer in the crystal lattice, wherein the AICD inhibitor and the coformer are associated only by non-ionic and noncovalent bonds, the coformer is a heterocyclic organic compound and is not a solvent, and wherein the coformer is included in an amount sufficient to provide an improvement in a physical property and/or bioavailability and/or an rate of dissolution and/or shorter time to Cmax of the AICD inhibitor, as compared to a physical property, bioavailability, rate of dissolution, and time to Cmax of the AICD inhibitor without the coformer, wherein the AICD inhibitor is a praced, and the coformer is selected from a group consisting of nicotinamide, picolinamide, isonicotinamide, isonicotinic acid, and nicotinic acid; and the praced is itanapraced, the coformer is nicotinamide, and a stoichiometric ratio of itanapraced to nicotinamide is from about 0:8:1.2 to about 1.2:0.8, and the co-crystal comprises an X-ray Powder Diffraction Pattern (XRPD) that is substantially the same as the X-ray Powder Diffraction Pattern (XRPD) shown in FIG. 3A.

The invention is also directed to a pharmaceutical formulation comprising a therapeutically effective amount of a praced, the praced being in a form of a co-crystal, the co-crystal comprising molecules of the praced and a coformer in a crystal lattice, the praced interacting nonionically with the coformer in a crystal lattice, wherein the praced and the coformer are associated only by non-ionic and noncovalent bonds, the coformer is a nonvolatile heterocyclic organic compound having a pyridinyl moiety and is associated with the praced only via the non-ionic and noncovalent bonds, and wherein the coformer is included in an amount sufficient to provide an improved bioavailability and/or an enhanced rate of dissolution and/or shorter time to Cmax of the praced, as compared to a bioavailability, rate of dissolution, and time to Cmax of the praced without the coformer, such that when the pharmaceutical formulation is administered to a human, the coformer dissociates from the praced. Once the coformer dissociates from praced, the praced is available to provide a pharmacologic effect(s).

The invention is also directed to a pharmaceutical formulation comprising a therapeutically effective amount of a praced, the praced being in a form of a co-crystal, the co-crystal comprising molecules of the praced and a coformer in a crystal lattice, the praced interacting nonionically with the coformer in the crystal lattice, wherein the praced and the coformer are associated only by non-ionic and noncovalent bonds, the coformer is a nonvolatile heterocyclic organic compound having a pyridinyl moiety and is not a solvent, and wherein the coformer is included in an amount sufficient to render the co-crystal less hygroscopic, as compared to a hygroscopicity of the praced without the coformer, such that when the pharmaceutical formulation is administered to a human, the coformer dissociates from the praced.

The hydroscopicity of the pharmaceutical formulations according to the invention may be such that the pharmaceutical formulations gain or lose from about 0.01% to 0.20% w/w, from about 0.08% to 0.20% w/w, or from about 0.1% to 0.20% w/w, all at 25° C. between 5-95% RH (relative humidity), and hydroscopicity of the praced without the coformer may be such that the praced gains or loses more than 0.20% but less than 2% w/w, more than about 0.5% but less than 2% w/w or more than about 0.8% by less than 2% w/w, all at 25° C. between 5-95% RH (relative humidity). The reduced hygroscopicity of the pharmaceutical formulations may allow, e.g., for an increased stability and/or increased shelf-life and/or easier incorporation of the pharmaceutical formulations into a pharmaceutical dosage form(s), as compared to the praced without the coformer.

The invention is further directed to a pharmaceutical formulation comprising a therapeutically effective amount of a praced, the praced being in a form of a co-crystal, the co-crystal comprising molecules of the praced and a coformer in a crystal lattice, the praced interacting nonionically with the coformer in the crystal lattice, wherein the praced and the coformer are associated only by non-ionic and noncovalent bonds, the coformer is a nonvolatile heterocyclic organic compound having a pyridinyl moiety and is not a solvent, and wherein the coformer is included in an amount sufficient to render the co-crystal more water soluble, as compared to a water solubility of the praced without the coformer, such that when the pharmaceutical formulation is administered to a human, the coformer dissociates from the praced. For example, the co-crystal may be water soluble, whereas the praced without the coformer may not be water soluble or may have a lower solubility in water. The increased water solubility of the pharmaceutical formulation may allow, e.g., for an improved bioavailability and/or a faster onset of action and/or a shorter $T_{max}$ and/or higher plasma concentrations (e.g., $C_{max}$) and/or higher AUC, as compared to the administration of the praced without the coformer.

The invention encompasses a pharmaceutical formulation comprising a therapeutically effective amount of an AICD inhibitor having a carboxylic acid moiety, the AICD inhibitor being in a form of a co-crystal, the co-crystal comprising a crystal lattice comprising molecules of the AICD inhibitor and a coformer, the AICD inhibitor interacting nonionically with the coformer in the crystal lattice, wherein the AICD inhibitor and the coformer are associated only by non-ionic and noncovalent bonds, and wherein the coformer is a nonvolatile heterocyclic organic compound having a pyridinyl moiety and is not a solvent. The coformer may be included in an amount sufficient to provide an improvement in a physical property of the AICD inhibitor, as compared to a physical property of the AICD inhibitor without the coformer. The improved physical property may, e.g., be hygroscopicity.

In certain embodiments, the invention is directed to a pharmaceutical formulation comprising a co-crystal, the co-crystal comprising a crystal lattice comprising molecules of an AICD inhibitor and a coformer, the AICD inhibitor interacting nonionically with the coformer in the crystal lattice, wherein the AICD inhibitor includes a carboxylic acid moiety and the coformer is a nonvolatile heterocyclic organic compound and is not a solvent, the AICD inhibitor and the coformer being associated only by non-ionic and noncovalent bonds.

The invention is further directed to a pharmaceutical formulation comprising a therapeutically effective amount of an AICD inhibitor, the AICD inhibitor being in a form of a co-crystal, the co-crystal comprising a crystal lattice comprising molecules of the AICD inhibitor and a coformer, the AICD inhibitor interacting nonionically with the coformer in the crystal lattice, wherein the AICD inhibitor includes a carboxylic acid moiety and the coformer is a nonvolatile heterocyclic organic compound having a pyridinyl moiety, the AICD inhibitor and the coformer being associated only by non-ionic and noncovalent bonds, and the coformer is not a solvent.

The AICD inhibitor in the pharmaceutical formulations of the invention may, e.g., be a praced. In some of the embodiments, the praced is itanapraced, and the coformer is selected from a group consisting of nicotinamide, picolinamide, isonicotinamide, isonicotinic acid, and nicotinic acid.

The invention is also directed to a co-crystal comprising (i) an ingredient that binds APP and/or inhibits the transcriptional activity of AICD and/or is capable of microglial modulation and (ii) a coformer. The coformer itself may or may not be biologically active. The ingredient and the coformer are not bound covalently and ionically in the co-crystal. Instead, the ingredient and the coformer are associated by nonionic and noncovalent bonds, e.g., hydrogen bonding, van der Walls forces, and I-interactions. The co-crystal has physical and chemical properties that are different from those of the ingredient, the coformer, their polymorphs, salts, hydrates and solvates. For example, as compared to ingredient and the coformer, their polymorphs, salts, hydrates and solvates, the co-crystal may have an improved aqueous solubility and/or stability. The co-crystal may also have an improved bioavailability and/or an enhanced rate of dissolution and/or shorter time to Cmax, as compared to a bioavailability, rate of dissolution, and time to Cmax, of the ingredient. The co-crystal may, e.g., also be less hygroscopic than the ingredient, and may be more suitable for incorporation into a solid dosage form. The co-crystal may, e.g., be used as an active pharmaceutical ingredient (API) in a pharmaceutical formulations, including, e.g., solid dosage forms (e.g., tablets and capsules). The co-crystal and the pharmaceutical formulations may be used in the prevention and treatment of neurodegenerative disorders, including, e.g., Parkinson's disease (PD), Alzheimer's disease (AD), Multiple Sclerosis (MS), juvenile neuronal ceroid lipofuscinosis (JNCL) (Batten disease type-3), age-related macular degeneration (AMD); dementias (e.g., MCI), neurological infection, neurologic injury (Traumatic Brain Injury (TBI)) and neurologic inflammation.

The invention is more specifically directed in part to a co-crystal comprising itanapraced and a coformer. Intanapraced and the coformer are not bound covalently and ionically in the co-crystal. Instead, itanapraced and the coformer are associated by nonionic and noncovalent bonds. The coformer in the co-crystal may or may not be biologically active, and may, e.g., be selected from a group consisting of nicotinamide, picolinamide, isonicotinamide, isonicotinic acid, and nicotinic acid. The co-crystal has physical and chemical properties that are different from those of itanapraced, the coformer, their polymorphs, salts, hydrates and solvates. For example, as compared to itanapraced and the coformer, their polymorphs, salts, hydrates and solvates; the co-crystal may have an improved aqeuous solubility and/or stability, and may be more suitable for incorporation into a solid dosage form. The co-crystal may be less hygroscopic than itanapraced and/or more water soluble than itanapraced. The co-crystal may also be non-hygroscopic. The co-crystal may also have an improved bioavailability and/or an enhanced rate of dissolution and/or shorter time to $C_{max}$, as compared to a bioavailability, rate of dissolution, and time to $C_{max}$, of itanapraced.

In certain embodiments, the invention is directed to a co-crystal comprising a crystal lattice comprising molecules of itanapraced and a coformer, the AICD inhibitor interacting nonionically with the coformer in the crystal lattice, wherein the coformer is a nonvolatile heterocyclic organic compound having a pyridinyl moiety, the AICD inhibitor and the coformer being associated only by non-ionic and noncovalent bonds.

The invention is further directed to a co-crystal comprising itanapraced and nicotinamide. The stoichiometric ratio of itanapraced to nicotinamide in the co-crystal may be from about 0:8:1.2 to about 1.2:0.8 (e.g., about 1:1). Intanapraced and nicotinamide are not bound covalently and ionically in the co-crystal. Rather, intanapraced and nicotinamide are associated by nonionic and noncovalent bonds. In certain embodiments, itanapraced and nicotinamide may be associated at a pyridinyl moiety of nicotinamide and a carboxylic acid moiety of itanapraced. The co-crystal may comprise an X-ray Powder Diffraction Pattern (XRPD) with specific peaks, expressed in 2θ produced from a Cu radiation source (λ=1.54 Å after Ni filtering), at about 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ. The X-ray Powder Diffraction Pattern (XRPD) may be substantially the same as the X-ray Powder Diffraction Pattern (XRPD) shown in FIG. 3A. For example, the co-crystal may have an X-ray Powder Diffraction Pattern (XRPD) with specific peaks, expressed in 2θ produced from a Cu radiation source (λ=1.54 Å after Ni filtering) at about 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°. The co-crystal may provide a first endothermic event with an onset at 114.0° C., a peak maximum of 116.7° C., and a ΔH of 60.5 J/g, as measured by differential scanning calorimetry (DSC analysis). The co-crystal may further provide a second endothermic event with a peak maximum at 159.1° C. and an endset at 183.2° C., as measured by differential scanning calorimetry (DSC analysis). The co-crystal has physical and chemical properties that are different from those of itanapraced, nicotinamide, their polymorphs, salts, hydrates and solvates. As compared to itanapraced and nicotinamide their polymorphs, salts, hydrates and solvates; the co-crystal has an improved aquous solubility and/or is less hygroscopic than intanapraced. The co-crystal may have an improved stability, as compared to intanapraced. The co-crystal may be non-hygroscopic. Consequently, the co-crystal moremore suitable for incorporation into a solid dosage form (e.g., a tablet or a capsule). The co-crystal may also have an improved bioavailability and/or an enhanced rate of dissolution and/or shorter time to Cmax, as compared to a bioavailability, rate of dissolution, and time to Cmax, of itanapraced.

The invention is directed in part to a co-crystal comprising itanapraced and nicotinamide, wherein said co-crystal comprises nicotinamide and a) has an X-ray Powder Diffraction Pattern (XRPD) with specific peaks, expressed in 2θ produced from a Cu radiation source (λ=1.54 Å after Ni filtering), at 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ; and/or b) has an X-ray Powder Diffraction Pattern diffraction pattern as depicted in FIG. 3A.

The invention is directed in part to a co-crystal comprising itanapraced and nicotinamide, wherein said co-crystal comprises nicotinamide and has an X-ray Powder Diffraction Pattern (XRPD) with specific peaks, expressed in 2θ produced from a Cu radiation source (λ=1.54 Å after Ni filtering), at 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ; wherein the co-crystal is less hygroscopic than itanapraced.

The invention is directed in part to a co-crystal comprising itanapraced and nicotinamide, wherein said co-crystal comprises nicotinamide and has an X-ray Powder Diffraction Pattern diffraction pattern as depicted in FIG. 3A; wherein the co-crystal is less hygroscopic than itanapraced.

The invention is directed in part to a co-crystal comprising itanapraced and nicotinamide, wherein said co-crystal comprises nicotinamide and has an X-ray Powder Diffraction Pattern (XRPD) with specific peaks, expressed in 2θ produced from a Cu radiation source (λ=1.54 Å after Ni filtering), at 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ; wherein wherein the itanapraced and the nicotinamide are associated at a pyridinyl moiety of the nicotinamide and a carboxylic acid moiety of the itanapraced.

The invention is directed in part to a co-crystal comprising itanapraced and nicotinamide, wherein said co-crystal comprises nicotinamide and has an X-ray Powder Diffraction Pattern diffraction pattern as depicted in FIG. 3A; wherein wherein the itanapraced and the nicotinamide are associated at a pyridinyl moiety of the nicotinamide and a carboxylic acid moiety of the itanapraced.

The invention is directed in part to a co-crystal comprising itanapraced and nicotinamide, wherein said co-crystal comprises nicotinamide and has an X-ray Powder Diffraction Pattern (XRPD) with specific peaks, expressed in 2θ produced from a Cu radiation source (λ=1.54 Å after Ni filtering), at 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ, wherein the co-crystal provides a first endothermic event with an onset at 114.0° C., a peak maximum of 116.7° C., and a ΔH of 60.5 J/g, as measured by differential scanning calorimetry (DSC analysis).

The invention is directed in part to a co-crystal comprising itanapraced and nicotinamide, wherein said co-crystal comprises nicotinamide and has an X-ray Powder Diffraction Pattern (XRPD) with specific peaks, expressed in 2θ produced from a Cu radiation source (λ=1.54 Å after Ni filtering), at 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ, wherein the co-crystal provides a first endothermic event with an onset at 114.0° C., a peak maximum of 116.7° C., and a ΔH of 60.5 J/g, as measured by differential scanning calorimetry (DSC analysis), and a second endothermic event with a peak maximum at 159.1° C. and an endset at 183.2° C., as measured by differential scanning calorimetry (DSC analysis).

The invention further provides a process for preparing a co-crystal comprising an ingredient that binds APP and/or inhibits the transcriptional activity of AICD and/or is capable of microglial modulation, the process comprising dissolving the ingredient and a coformer in a solvent and isolating a co-crystal comprising the ingredient and the coformer.

In a still further aspect, the invention provides a process for the production of a co-crystal comprising an ingredient that binds APP and/or inhibits the transcriptional activity of AICD and/or is capable of microglial modulation, the process comprising: (i) grinding, heating or contacting in solution the ingredient with a coformer, under crystallization conditions, so as to form a solid phase; and (ii) isolating co-crystals comprising the ingredient and the coformer.

In a further aspect, the invention provides a process for the production of a co-crystal, which process comprises: (i) providing an ingredient that binds APP and/or inhibits the transcriptional activity of AICD and/or is capable of microglial modulation; (ii) providing a coformer; (iii) grinding, heating or contacting in solution the ingredient with the coformer under crystallization conditions, and (iv) isolating co-crystals formed thereby.

The invention also provides a process for preparing a co-crystal, the process comprising dissolving itanapraced and a coformer in a solvent and isolating a co-crystal comprising itanapraced and the coformer.

In a still further aspect the present invention provides a process for the production of a co-crystal, which comprises: (i) grinding, heating or contacting in solution itanapraced with a coformer, under crystallization conditions, so as to form a solid phase; and (ii) isolating co-crystals comprising the itanapraced and the coformer.

In a further aspect, the present invention provides a process for the production of a co-crystal, which process comprises: (i) providing itanapraced; (ii) providing nicotinamide; (iii) grinding, heating or contacting in solution the itanapraced with nicotinamide under crystallization conditions, and (iv) isolating co-crystals formed thereby.

The invention also provides a process for preparing a co-crystal, the process comprising dissolving itanapraced and nicotinamide in a solvent and isolating a co-crystal comprising itanapraced and nicotinamide.

In a still further aspect the present invention provides a process for the production of a co-crystal, which comprises: (i) grinding, heating or contacting in solution itanapraced with nicotinamide, under crystallization conditions, so as to form a solid phase; and (ii) isolating co-crystals comprising the itanapraced and the nicotinamide.

In a further aspect, the present invention provides a process for the production of a co-crystal, which process comprises: (i) providing itanapraced; (ii) providing nicotinamide; (iii) grinding, heating or contacting in solution the itanapraced with nicotinamide under crystallization conditions, and (iv) isolating co-crystals formed thereby.

Any of the co-crystals described in the present specification may, e.g., be used as an active pharmaceutical ingredient (API) in a pharmaceutical formulations, including, e.g., solid dosage forms (e.g., tablets and capsules).

The invention is further directed in part to a pharmaceutical formulation comprising an effective amount of a co-crystal as described in any of the paragraphs above and a pharmaceutically acceptable excipient. The co-crystal may, e.g., comprise from about 2% to about 98% of the formulation by weight. The pharmaceutically acceptable excipient may comprise from about 0.1% to about 99.9% of the formulation by weight. A unit dose of the pharmaceutical formulation may comprise from about 3 mg to about 3500 mg of the co-crystal, the co-crystal comprising itanapraced and nicotinamide, a stoichiometric ratio of intanapraced to nicotinamide in the co-crystal being from 0:8:1.2 to about 1.2:0.8 (e.g., about 1:1). The pharmaceutical formulation may, e.g., be a solid dosage form. The solid dosage forms may, e.g., be an oral solid dosage forms such as, e.g., tablets or a capsules. These oral solid dosage forms may be formulated as immediate release, controlled release, sustained (extended) release or modified release formulations.

The invention is further directed to a pharmaceutical itanapraced formulation with a greater solubility and/or dissolution and/or bioavailability and/or AUC and/or reduced time to $T_{max}$, and/or the time to reach peak blood serum levels and/or higher $C_{max}$ and/or the maximum blood serum concentration, when compared to the neutral form or salt of itanapraced alone. The pharmaceutical formulation comprises a co-crystal of itanapraced, rather than the neutral form, polymorph, solvate, hydrate, or salt of itanapraced.

In a further aspect, the invention provides a process for modulating the bioavailability of itanapraced when administered in its normal and effective dose range, whereby the AUC is increased and/or the time to Tmax is reduced and/or Cmax is increased, which process comprises:
  (1) grinding, heating or contacting in solution ipanapraced with a coformer under crystallization conditions, so as to form a co-crystal of the itanapraced and the coformer;
  (2) isolating co-crystals comprising itanapraced and the coformer.

Examples of the above embodiment include: co-crystal compositions with a time to $T_{max}$ that is reduced by at least 10% as compared to the free crystalline form, co-crystal compositions with a time to $T_{max}$ that is reduced by at least 20% over the free crystalline form, co-crystal compositions with a time to $T_{max}$ that is reduced by at least 40% over the free crystalline form, co-crystal compositions with a time to $T_{max}$ that is reduced by at least 50% over the free crystalline form, co-crystal compositions with a $T_{max}$ that is reduced by at least 60% over the free crystalline form, co-crystal compositions with a Tmax that is reduced by at least 70% over the free crystalline form, co-crystal compositions with a $T_{max}$ that is reduced by at least 80% over the free crystalline form, co-crystal compositions with a $C_{max}$ that is increased by at least 20% over the free crystalline form, co-crystal compositions with a $C_{max}$ that is increased by at least 30% over the free crystalline form, co-crystal compositions with a $C_{max}$ that is increased by at least 40% over the free crystalline form, co-crystal compositions with a $C_{max}$ that is increased by at least 50% over the free crystalline form, co-crystal compositions with a $C_{max}$ that is increased by at least 60% over the free crystalline form, co-crystal compositions with a $C_{max}$ that is increased by at least 70% over the free crystalline form, co-crystal compositions with a Cmax that is increased by at least 80% over the free crystalline form, co-crystal compositions with an AUC that is increased by at least 10% over the free crystalline form, co-crystal compositions with an AUC that is increased by at least 20% over the free crystalline form, co-crystal compositions with an AUC that is increased by at least 30% over the free crystalline form, co-crystal compositions with an AUC that is increased by at least 40% over the free crystalline form, co-crystal compositions with an AUC that is increased by at least 50% over the free crystalline form, co-crystal compositions with an AUC that is increased by at least 60% over the free crystalline form, co-crystal compositions with an AUC that is increased by at least 70% over the free crystalline form, or co-crystal compositions with an AUC that is increased by at least 80% over the free crystalline form.

In a further aspect the present invention provides a process for improving the dose response of itanapraced, which process comprises:
  (i) contacting in solution itanapraced with a coformer under crystallization conditions, so as to form a co-crystal of itanapraced and the co-crystal;
  (ii) isolating co-crystals comprising itanapraced and the coformer.

In a still further aspect the present invention provides a process for improving the stability of a itanapraced in its free form or a salt thereof, which process comprises:
  (i) Grinding, heating or contacting in solution itanapraced with a coformer under crystallization conditions, so as to form a co-crystal of itanapraced and the coformer;
  (ii) isolating co-crystals comprising itanapraced and the coformer.

In any of the processes described in the specification, the coformer may be selected from a group consisting of nicotinamide, picolinamide, isonicotinamide, isonicotinic acid, and nicotinic acid. Other coformers are also encompassed by the invention.

In any of the processes, the coformer may be nicotinamide.

The co-crystal and the pharmaceutical formulations as described in the specification may be used in the prevention and treatment of neurodegenerative disorders, including, e.g., Parkinson's disease (PD), Alzeimer's disease (AD), Multiple Sclerosis (MS), juvenile neuronal ceroid lipofuscinosis (JNCL) (Batten disease type-3), age-related macular degeneration (AMD); dementias (e.g., MCI), neurological infection, neurologic injury (Traumatic Brain Injury (TBI)) and neurologic inflammation. The co-crystal and pharmaceutical formulations may also be used in treatment of tauopathies, especially Amyotrophic Lateral Sclerosis (ALS), Pick's disease, Frontal Temporal Dementia (FTD) and Progressive Supranuclear Palsy (PSP) as well as brain hypoxia.

The invention is further directed to a method of preventing, inhibiting and/or treating a neurodegenerative condition in a human, comprising administering a therapeutically effective dosage regimen of a co-crystal comprising an ingredient that binds APP.

The invention is further directed to a method of preventing, inhibiting and/or treating a neurodegenerative condition in a human, comprising administering a therapeutically effective dosage regimen of a co-crystal comprising an ingredient that inhibits the transcriptional activity of AICD.

The invention is further directed to a method of preventing, inhibiting and/or treating a neurodegenerative condition in a human, comprising administering a therapeutically effective dosage regimen of a co-crystal comprising an ingredient capable of microglial modulation.

The invention is further directed to a method of preventing, inhibiting and/or treating a neurodegenerative condition in a human, comprising administering a therapeutically effective dosage regimen of a co-crystal comprising itanapraced. In certain embodiments, the co-crystal comprises itanapraced and a coformer, wherein the coformer is nicotinamide, a stoichiometric ratio of itanapraced to nicotinamide is from about 0:8:1.2 to about 1.2:0.8, and the co-crystal comprises an X-ray Powder Diffraction Pattern (XRPD) with specific peaks, expressed in 2θ produced from a Cu radiation source (λ=1.54 Å after Ni filtering), at about 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ.

The invention is further directed to a method of preventing, inhibiting and/or treating inflammation in a human, comprising administering a therapeutically effective dosage regimen of a co-crystal comprising an ingredient that inhibits the transcriptional activity of AICD.

The invention is further directed to a method of preventing, inhibiting and/or treating inflammation in a human, comprising administering a therapeutically effective dosage regimen of a co-crystal comprising an ingredient capable of microglial modulation.

The invention is further directed to a method of preventing, inhibiting and/or treating inflammation in a human, comprising administering a therapeutically effective dosage regimen of a co-crystal comprising an ingredient that binds APP.

The invention is further directed to a method of preventing, inhibiting and/or treating inflammation in a human, comprising administering a therapeutically effective dosage regimen of a co-crystal comprising itanapraced. In certain embodiments, the co-crystal comprises itanapraced and a coformer, wherein the coformer is nicotinamide, a stoichiometric ratio of itanapraced to nicotinamide is from about 0:8:1.2 to about 1.2:0.8, and the co-crystal comprises an X-ray Powder Diffraction Pattern (XRPD) with specific peaks, expressed in 2θ produced from a Cu radiation source (λ=1.54 Å after Ni filtering), at about 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ.

The invention is further directed to a method of preventing, inhibiting and/or treating dementia in a human, comprising administering a therapeutically effective dosage regimen of a co-crystal comprising an ingredient that inhibits the transcriptional activity of AICD.

The invention is further directed to a method of preventing, inhibiting and/or treating dementia in a human, comprising administering a therapeutically effective dosage regimen of a co-crystal comprising an ingredient capable of microglial modulation.

The invention is further directed to a method of preventing, inhibiting and/or treating dementia in a human, comprising administering a therapeutically effective dosage regimen of a co-crystal comprising an ingredient that binds APP.

The invention is further directed to a method of preventing, inhibiting and/or treating dementia in a human, comprising administering a therapeutically effective dosage regimen of a co-crystal comprising itanapraced. In certain embodiments, the co-crystal comprises itanapraced and a coformer, wherein the coformer is nicotinamide, a stoichiometric ratio of itanapraced to nicotinamide is from about 0:8:1.2 to about 1.2:0.8, and the co-crystal comprises an X-ray Powder Diffraction Pattern (XRPD) with specific peaks, expressed in 2θ produced from a Cu radiation source (λ=1.54 Å after Ni filtering), at about 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ.

The invention is further directed to a method of preventing, inhibiting and/or treating a neurologic injury (e.g., TBI) in a human, comprising administering a therapeutically effective dosage regimen of a co-crystal comprising an ingredient that inhibits the transcriptional activity of AICD.

The invention is further directed to a method of preventing, inhibiting and/or treating a neurologic injury in a human, comprising administering a therapeutically effective dosage regimen of a co-crystal comprising an ingredient capable of microglial modulation.

The invention is further directed to a method of preventing, inhibiting and/or treating neurologic injury in a human, comprising administering a therapeutically effective dosage regimen of a co-crystal comprising an ingredient that binds APP.

The invention is further directed to a method of preventing, inhibiting and/or treating neurologic injury in a human, comprising administering a therapeutically effective dosage regimen of a co-crystal comprising itanapraced. In certain embodiments, the co-crystal comprises itanapraced and a coformer, wherein the coformer is nicotinamide, a stoichiometric ratio of itanapraced to nicotinamide is from about 0:8:1.2 to about 1.2:0.8, and the co-crystal comprises an X-ray Powder Diffraction Pattern (XRPD) with specific peaks, expressed in 2θ produced from a Cu radiation source (λ=1.54 Å after Ni filtering), at about 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ.

The invention is specifically directed to a method of treating a neurodegenerative condition in a human, comprising administering a therapeutically effective dosage regimen of a co-crystal comprising itanapraced and a coformer, wherein the coformer is nicotinamide, a stoichiometric ratio of itanapraced to nicotinamide is from about 0:8:1.2 to about 1.2:0.8, and the co-crystal comprises an X-ray Powder Diffraction Pattern (XRPD) with specific peaks, expressed in 2θ produced from a Cu radiation source (λ=1.54 Å after Ni filtering), at about 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ. The neurodegenerative condition may be selected from a group consisting of Parkinson's disease, Alzeimer's disease, Multiple Sclerosis, juvenile neuronal ceroid lipofuscinosis, age-related macular degeneration, dementias, neurological infection, neurologic injury, a tauopathy, Pick's disease, and Progressive Supranuclear Palsy, brain hypoxia, and neurologic inflammation.

Thus, in certain embodiments, the invention is directed to a method of treating Parkinson's disease, the method comprising administering a therapeutically effective dosage regimen of a co-crystal comprising itanapraced and a coformer, wherein the coformer is nicotinamide, a stoichiometric ratio of itanapraced to nicotinamide is from about 0:8:1.2 to about 1.2:0.8, and the co-crystal comprises an X-ray Powder Diffraction Pattern (XRPD) with specific peaks, expressed in 2θ produced from a Cu radiation source (λ=1.54 Å after Ni filtering), at about 14.63°; 14.90°; 15.56°; 16.71°; 18.24°; 18.46°; 20.03°; 20.27°; 22.01°; 22.27°; 24.17°; 24.47°;

26.14°; 26.47°; 27.83°; 28.85°; 29.97°; 30.64°; 32.42°; 34.07°; and 39.14°, all +/−0.2 degrees 2θ.

The invention is further directed to a method of preventing, inhibiting and/or treating acute respiratory stress syndrome (ARDS) induced by the release of cytokines and other toxic molecules from the brain of a human infected by COVID-19 into the blood stream, comprising administering a therapeutically effective dosage regimen of a co-crystal comprising an ingredient that inhibits the transcriptional activity of AICD.

The invention is further directed to a method of preventing, inhibiting and/or treating acute respiratory stress syndrome (ARDS) induced by the release of cytokines and other toxic molecules from the brain of a human infected by COVID-19 into the blood stream, comprising administering a therapeutically effective dosage regimen of a co-crystal comprising an ingredient that binds APP.

The invention is further directed to a method of preventing, inhibiting and/or treating acute respiratory stress syndrome (ARDS) induced by the release of cytokines and other toxic molecules from the brain of a human infected by COVID-19 into the blood stream, comprising administering a therapeutically effective dosage regimen of a co-crystal comprising an ingredient capable of microglial modulation.

The invention is further directed to a method of preventing, inhibiting and/or treating acute respiratory stress syndrome (ARDS) induced by the release of cytokines and other toxic molecules from the brain of a human infected by COVID-19 into the blood stream, comprising administering a therapeutically effective dosage regimen of a co-crystal comprising itanapraced. In certain embodiments, the co-crystal comprises itanapraced and a coformer, wherein the coformer is nicotinamide, a stoichiometric ratio of itanapraced to nicotinamide is from about 0:8:1.2 to about 1.2:0.8, and the co-crystal comprises an X-ray Powder Diffraction Pattern (XRPD) with specific peaks, expressed in 2θ produced from a Cu radiation source ($\lambda$=1.54 Å after Ni filtering), at about 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ.

The invention is further directed to a method of prophylactic treatment to prevent a human who been exposed to COVID-19 or to reduce the risk of the human from becoming neurologically infected with and/or reduce the severity of illness from COVID-19, comprising administering a therapeutically effective dosage regimen of a co-crystal according to the invention. The method may further comprise co-administering another drug which prevents, inhibits, or treats a neurological infection of a human patent by a coronavirus such as COVID-19 by the same or different mechanism of action.

The invention is also directed to a method of preventing, inhibiting and/or treating neuroinfection caused by a virus in a human, comprising administering a therapeutically effective dosage regimen of a co-crystal that comprises a drug that binds amyloid precursor protein (APP) in humans and inhibits the transcriptional activity of its intracellular domain (AICD) or modulates microglial function by inhibiting the production of pro-inflammatory cytokines and promoting phagocytosis to increase clearance of the pathogen, thereby preventing, inhibiting and/or treating Acute Respiratory Stress Syndrome (ARDS) in the human.

The invention is further directed to the use of a pharmaceutical composition comprising a therapeutically effective amount of a co-crystal of the invention to prevent, inhibit and/or treat neurological infection of a human by COVID-19.

The invention is also directed to a pharmaceutical composition comprising a therapeutically effective amount of a co-crystal of the invention to inhibit the neurological infection of a human with COVID-19.

The pharmaceutical composition or formulation used in be methods of the invention may be an oral solid dosage form such as, e.g., a tablet or capsule. The pharmaceutical compositions may, for example, be administered prophylactically to humans in order to prevent or inhibit neurological infection with a coronavirus such as COVID-19.

The invention is also directed to a method of preventing, inhibiting and/or treating neurological disorder of a human, comprising administering a therapeutically effective dosage regimen of a co-crystal comprising a drug that binds amyloid precursor protein (APP) in humans and/or inhibit the transcriptional activity of its intracellular domain (AICD).

In other embodiments, the invention is directed to a method of preventing, inhibiting and/or treating neurological infection of a human by COVID-19, comprising administering a therapeutically effective dosage regimen of a co-crystal comprising a drug that modulates microglial function by inhibiting the production of pro-inflammatory cytokines and promoting phagocytosis to increase clearance of the pathogen.

The invention is also directed to a method of preventing, inhibiting and/or treating neuroinfection caused by a virus in a human, comprising administering a therapeutically effective dosage regimen of a co-crystal comprising a drug that binds amyloid precursor protein (APP) in humans and inhibits the transcriptional activity of its intracellular domain (AICD) or modulates microglial function by inhibiting the production of pro-inflammatory cytokines and promoting phagocytosis to increase clearance of the virus (pathogen), and thereby preventing, inhibiting and/or treating neuroinfection Acute Respiratory Stress Syndrome (ARDS) in the human.

The invention is further directd to a method of preventing, inhibiting and/or treating Acute Respiratory Stress Syndrome (ARDS) from which COVID-19 patients often die, comprising administering a therapeutically effective dosage regimen of a co-crystal comprising a drug that binds amyloid precursor protein (APP) in humans and inhibits the transcriptional activity of its intracellular domain (AICD) or that modulates microglial function by inhibiting the production of pro-inflammatory cytokines and promoting phagocytosis to increase clearance of the pathogen.

The invention is directed in part to a pharmaceutical composition comprising a therapeutically effective amount of a co-crystal comprising a praced to inhibit the neurological infection of a human with a coronavirus. In certain embodiments, the coronavirus is COVID-19.

In certain preferred embodiments of the invention, the formulations of the present invention are administered prophylactically to humans in order to prevent or inhibit neurological infection with a coronavirus such as COVID-19.

The invention is further directed in part to a method of prophylactic treatment to prevent a human who has been exposed to COVID-19 or to reduce the risk of the human from becoming infected with and/or reduce the severity of illness from COVID-19, comprising administering a therapeutically effective amount of a co-crystal comprising itanapraced. In certain embodiments, the method further comprises co-administering another drug which prevents, inhibits, or treats an infection of a human patent by a coronavirus such as COVID-19 by the same or different mechanism of action.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" in the present specification means a value within 20% (+20%) of the value recited immediately after the term "about," including the value equal to the upper limit (i.e., +20%) and the value equal to the lower limit (i.e.,-20%) of this range. For example, the phrase "about 100" encompasses any numeric value that is between 80 and 120, including 80 and 120.

The term "co-crystal" means a crystalline material composed of molecules of two or more different compounds in a crystal lattice, one or more of which is the API(s), in a defined stoichiometric ratio within the same crystal lattice that are associated by nonionic and noncovalent bonds.

The term "coformer" means a component that interacts nonionically with the API in the crystal lattice, that is preferably not a solvent, is typically nonvolatile, and includes heterocyclic organic compounds.

"Effective amount" or "therapeutically effective amount" are used interchangeably herein, and refer to an amount of a compound, formulation, material, or composition, as described herein effective to achieve a particular biological result. Such results may include, but are not limited to, the treatment of a disease or condition as determined by any means suitable in the art.

The term "polymorphs" means different crystalline forms of the same API and amorphous forms of the same API.

As used herein, the term "pharmaceutical composition" refers to a mixture of at least one compound of the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to oral, and parenteral (e.g., intravenous) administration.

"Pharmaceutically acceptable" refers to those properties and/or substances that are acceptable to the patient from a pharmacological/toxicological point of view and to the manufacturing pharmaceutical chemist from a physical/chemical point of view regarding composition, formulation; stability, patient acceptance and bioavailability.

The term "treat" or "treating", as used herein, includes but is not limited to, alleviation or amelioration of one or more symptoms or conditions; diminishment of extent of disease, disorder, or condition; stabilized (i.e., not worsening) state of disease, disorder, or condition; preventing spread of disease, disorder, or condition (e.g., delay or slowing the progress of the disease, disorder, or condition; amelioration or palliation of the disease, disorder, or condition; and remission (whether partial or total), whether detectable or undetectable.

"Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

As used herein, "preventing" includes preventing the initiation of a disease and/or reducing the severity or intensity of the disease.

As used herein, "alleviate" is used interchangeably with the term "treat." Treating a disease, disorder or condition may or may not include complete eradication or elimination of the symptom.

The term "salt" means a compound that results from replacement of part or all of the acid hydrogen of an acid by a metal or a radical acting like a metal: an ionic or electrovalent crystalline compound.

The term "therapeutic" as used herein means a treatment and/or prophylaxis. Throughout this disclosure, various aspects of the invention can be presented in a range format.

It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The term "substantially the same as the X-ray Powder Diffraction Pattern shown in FIG. 3A" is intended to indicate that the 2-theta angle values of the X-ray powder diffraction patterns may vary slightly (+) 0.2° from sample preparation to sample preparation and from one machine to another, from one sample to another, or as a result of slight variations in sample preparation and measurement conditions utilised, so the peak positions shown in FIG. 3A and described in the Peak List are not to be construed as absolute values.

The abbreviation "CSP-1103" means itanapraced.
The abbreviation "CHF5074" means itanapraced.
The abbreviation "NCT" means nicotinamide.
The abbreviation "CSPNCT" means co-crystal of itanapraced and nicotinamide.

For the purposes of the present invention, the term "non-hygrosopic" means that the molecule gains or loses less than 0.20% w/w, at 25° C. between 5-95% RH (relative humidity).

For the purposes of the present invention, the term "slightly hygroscopic" means that the molecule gains or loses more than 0.20% w/w but less than 2% w/w-at 25° C. between 5-95% RH (relative humidity).

For the purposes of the present invention, the "neurodegenerative condition" includes Parkinson's disease (PD), Alzeimer's disease (AD), Multiple Sclerosis (MS), juvenile neuronal ceroid lipofuscinosis (JNCL) (Batten disease type-3), age-related macular degeneration (AMD); dementias (e.g., MCI), neurological infection, neurologic injury (Traumatic Brain Injury (TBI)) and neurologic inflammation. The "neurodegenerative condition" also includes tauopathies, especially Amyotrophic Lateral Sclerosis (ALS), Pick's disease, Frontal Temporal Dementia (FTD) and Progressive Supranuclear Palsy (PSP) as well as brain hypoxia.

For the purposes of the present invention, "AUC" is the area under the plot of plasma concentration of itanapraced (not logarithm of the concentration) against time after itanapraced administration. The area is conveniently determined by the "trapezoidal rule": the data points are connected by straight line segments, perpendiculars are erected from the abscissa to each data point, and the sum of the areas of the triangles and trapezoids so constructed is computed. When the last measured concentration (Cn, at time tn) is not zero, the AUC from tn to infinite time is estimated by Cn/kcl.

The AUC is of particular use in estimating bioavailability of itanapraced, and in estimating total clearance of itanapraced (CIT). Following single intravenous doses, AUC=D/CIT, for single compartment systems obeying first-order elimination kinetics; alternatively, AUC=$C_0/k_{el}$. With routes other than the intravenous, for such systems, AUC=F·D/CIT, where F is the availability of the itanapraced.

For the purposes of the present invention, "dose response" is the quantitative relationship between the magnitude of response and the dose inducing the response and may be measured by conventional means known in the art. The curve relating effect (as the dependent variable) to dose (as the independent variable) for a itanapraced-cell system is the "dose-response curve". Typically, the dose-response curve is the measured response to a itanapraced plotted against the dose of the itanapraced (mg/kg) given. The dose response curve can also be a curve of AUC against the dose of the intanapraced given.

DETAILED DESCRIPTION OF THE INVENTION

The ingredient in the co-crystal of the invention may be itanapraced. Itanapraced is a first-in-class, orally active, small-molecule compound being developed by Applicant CereSpir, under a licensing agreement with Chiesi for the treatment of mild cognitive impairment, i.e. prevention of disease progression in patients at risk of developing Alzheimer's disease (AD).

Itanapraced

Itanapraced, 1-(3',4'-dichloro-2-fluoro[1,1'-biphenyl]-4-yl)-cyclopropanecarboxylic acid) (aka CSP-1103, formerly CHF 5074), belongs to a new class of drug compounds ("praceds") that bind the amyloid precursor protein (APP) and inhibit the transcriptional activity of its intracellular domain (AICD). Itanapraced may also modulate microglia.

The chemical structure of itanapraced is as follows:

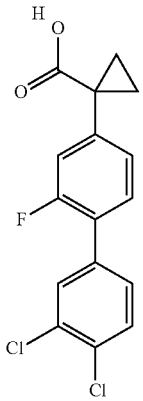

Itanapraced is an orally available brain-penetrant small molecule that has been tested in over 200 subjects in several Phase 1 studies and a Phase 2 study in mild cognitive impairment (MCI), with favorable results (Ross, 2013).

In addition to good safety and tolerability, itanapraced produced beneficial dose-related CSF differences in two key neuroinflammatory mediators, TNF-α and soluble CD40L, as well as in levels of total tau, a recognized marker of neurodegeneration. Patients also exhibited stable cognition throughout the duration of the trial.

Itanapraced has also been reported to have numerous beneficial effects in transgenic Alzheimer's mouse models (Imbimbo, 2007, 2009; Lanzillotta 2011), in a rat traumatic brain injury model (Lin et al., 2017) and in mouse models of Parkinson's Disease (manuscript submitted) and Juvenile Batten disease (unpublished).

Figure 10:
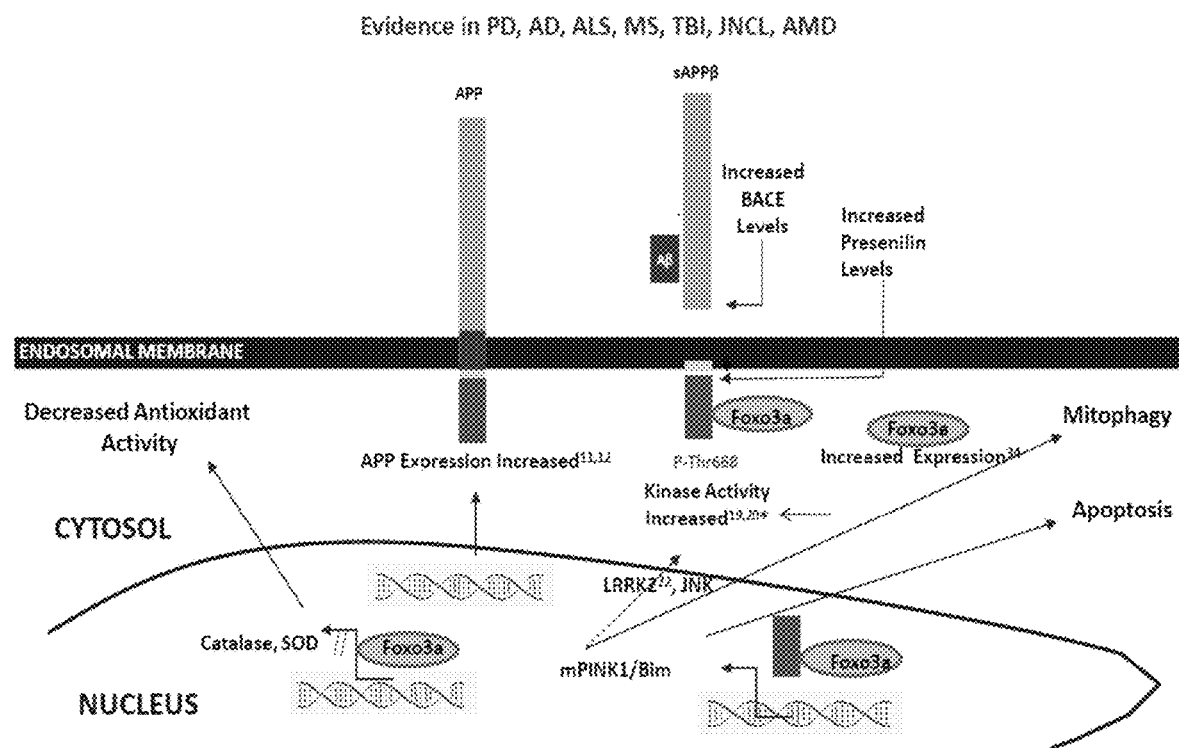
FIG. 10 depicts a model of dyregulated response to oxidative stress.

Thus, itanapraced appears to be effective in a broad range of disease indications pointing to a common mechanism linked by oxidative stress and neuroinflammation. A potential mechanism is depicted in FIG. 10.

Of particular relevance is the finding than itanapraced prevented the accumulation of hypertrophic microglia in the injured brain and attenuated both neurological and acute lung injury in rats after TBI (Li 2017).

It is believed than itanapraced could be used to prevent, inhibit or treat CNS infection and neurological damage in humans following peripheral COVID-19 infection which may also mitigate lung damage and loss of function.

Itanapraced is being explored for a number of disease indications including Parkinson's disease, Juvenile Batten disease and mild cognitive impairment by the Applicant. It is a small molecule with good oral bioavailability, a long plasma half-life and substantial penetration into the brain.

In a Phase 2 study in patients with mild cognitive impairment (MCI) treated up to two years (double blind for 3 months; open label thereafter), itanapraced was found to be well tolerated and produced dose-related statistically significant reductions, in the brain, of two key neuroinflammatory mediators, soluble CD40 ligand and TNF-α as well as, total tau, a recognized marker of neurodegeneration. In addition, patients exhibited stable cognitive function throughout the long duration of the trial.

With itanapraced, the Applicant has the most advanced compound that targets LRRK-mediated neurotoxicity with significant clinical trial experience involving more than 200 human subjects.

Nicotinamide

Nicotinamide (NCT) is a form of vitamin B3. It is a water soluble vitamin. Nicotinamide has the following structure:

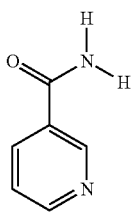

Nicotinamide is a precursor of (NAD) (+), which means cells can use a chemical reaction to turn nicotinamide into (NAD) (+). (NAD) (+) is a crucial component of the chemical reaction that mitochondria use to produce energy.

Nicotinamide found in food and used as a dietary supplement and medication. As a supplement, it may be used by mouth to prevent and treat pellagra (niacin deficiency). While nicotinic acid (niacin) may also be used for this purpose, nicotinamide has the benefit of not causing skin flushing. As a cream, nicotinamide may used to treat acne.

Nicotinamide can be used a coformer to form co-crystal of the present invention. Depending on the embodiment and dose, it may or may not have biological activity in the co-crystal of the invention.

In the cytoplasm of mammalian cells, AICD physically interacts with the transcription factor forkhead box O (FoxO), which is a crucial downstream mediator of APP-induced cell death and locomotion defect; and also translocates with FoxO into the nucleus upon oxidative stress.

Under conditions of acute oxidative stress, AICD transcriptional activity may cause cell damage by interacting with FOXO3a, a critical component of the physiological response mechanism to oxidative stress.

APP may therefore modulate FoxO-mediated cell death through AICD, which acts as a transcriptional co-activator of FoxO.

In addition, in neurons, astrocytes and microglia, APP may have a proinflammatory function.

Itanapraced may bind the amyloid precursor protein (APP) and inhibit the transcriptional activity of its intracellular domain (AICD). Itanapraced may also modulate microglia. Itanapraced may also inhibit inflammation. In some of the embodiments, nicotinamide may augment therapeutic activtity of intanapraced.

The co-crystals of the present invention may comprise itanapraced and nicotinamide and may therefore be used for treatment of neurodegeneration disorders, infections, dementias, inflammation, and injuries.

Dosage

The co-crystals of the present disclosure may be administered to a human subject at a dose of a dose of about 3 mg/day to about 3000 mg/day, about 4 mg/day to about 2500 mg/day, about 5 mg/day to about 2000 mg/day, about 10 mg/day to about 1500 mg/day, 10 mg/day to about 1000 mg/day, about 50 mg/day to about 600 mg/day, about 50 mg/day to about 500 mg/day, about 50 mg/day to about 400 mg/day, 50 mg/day to about 300 mg/day, or about 100 mg/day to about 30 mg/day.

The formulations of present invention may contain from about 3 mg to about 3500 mg of a co-crystal (e.g., a co-crystal comprising itanapraced and nicotinamide), accounting for more than once a day administration. Thus, the formlations of the present invention may be administered anywhere from 1 to 4 times per day, in order to provide the full daily dose.

Administration

The formulations of the present invention may be administered by any pharmaceutically effective route. For example, the co-crystals may be formulated in a manner such that they can be administered orally, intranasally, rectally, vaginally, sublingually, buccally, parenterally, or transdermally, and thus, be formulated accordingly. The co-crystals can be administered in liquid, tablet, parenteral, transrectal, transdermal or in any other form of administration suitable in order to achieve a therapeutic effect. Such formulations may contain additional fillers, carriers, excipient or excipients, inert or not, known to those skilled in the art of pharmaceutical preparations, in order to provide appropriate volume and/or facilitate absorption of the active drugs.

Different embodiments of the invention include, but are not limited to, the following examples: All possible combinations and permutations of co-crystals. In certain embodiments, the co-crystal is administered together or separately but concurrently with an additional drug which may work via the same or different mechanism to prevent, inhibit or treat infection by a neurogedenerative disorder. Another embodiment of the invention includes multiple variations in the pharmaceutical dosages of each drug in combination in a single dosage form as further outlined below. Another embodiment of the invention includes various forms of preparations including using solids, liquids, immediate or delayed or extended-release forms. Many types of variations are possible as known to those skilled in the art. Another embodiment of the invention includes multiple routes of administration, which may differ in different patients according to their preference, co-morbidities, side effect profile, and other factors (IV, PO, transdermal, etc.). Another embodiment of the invention includes the presence of other substances with the co-crystals comprising active drugs, known to those skilled in the art, such as fillers, carriers, gels, skin patches, lozenges or other modifications in the preparation to facilitate absorption through various routes (such as gastrointestinal, transdermal, etc.) and/or to extend the effect of the drugs, and/or to attain higher or more stable serum levels or to enhance the therapeutic effect of the active drugs in the combination.

Dosage Forms

In certain embodiments, the co-crystal of the invention may be formulated in a pharmaceutically acceptable oral dosage form. Oral dosage forms may include but are not limited to, oral solid dosage forms and oral liquid dosage forms. Oral solid dosage forms may include but are not limited to, tablets, capsules, caplets, powders, pellets, multiparticulates, beads, spheres and/or any combinations thereof. These oral solid dosage forms may be formulated as immediate release, controlled release, sustained (extended) release or modified release formulations.

The oral solid dosage forms of the present invention may also contain pharmaceutically acceptable excipients such as fillers, diluents, lubricants, surfactants, glidants, binders, dispersing agents, suspending agents, disintegrants, viscosity-increasing agents, film-forming agents, granulation aid, flavoring agents, sweetener, coating agents, solubilizing agents, and combinations thereof. Each of these excipient(s) may, e.g., comprise from about 0.1% to about 99.9%, from about 0.5% to about 95%, from about 1% to about 95%, from about 2% to about 95%, from about 3% to about 95%, or from about 5% to about 95% of the formulation by weight.

The solid dosage form may comprise a pharmaceutical composition comprising a co-crystal comprising itanapraced and a coformer, wherein the coformer is nicotinamide and the co-crystal comprises an X-ray Powder Diffraction Pattern (XRPD) with specific peaks, expressed in 2θ produced from a Cu radiation source (λ=1.54 Å after Ni filtering), at about 14.63°; 14.90°; 15.56°; 16.71°; 18.24°; 18.46°; 20.03°; 20.27°; 22.01°; 22.27°; 24.17°; 24.47°; 26.14°; 26.47°; 27.83°; 28.85°; 29.97°; 30.64°; 32.42°; 34.07°; and 39.14°, all +/−0.2 degrees 2θ; and (ii) a pharmaceutically acceptable excipient.

In some embodiments, the solid dosage forms of the present invention may be in the form of a tablet, (including a suspension tablet, a fast-melt tablet, a bite-disintegration tablet, a rapid-disintegration tablet, an effervescent tablet, or a caplet), a pill, a powder (including a sterile packaged powder, a dispensable powder, or an effervescent powder), a capsule (including both soft or hard capsules, e.g., capsules made from animal-derived gelatin or plant-derived HPMC, or "sprinkle capsules"), solid dispersion, solid solution, bioerodible dosage form, controlled release formulations, pulsatile release dosage forms, multiparticulate dosage forms, pellets, granules, or an aerosol. In other embodiments, the pharmaceutical formulation is in the form of a powder. In still other embodiments, the pharmaceutical formulation is in the form of a tablet, including but not limited to, a fast-melt tablet. Additionally, pharmaceutical formulations of the present invention may be administered as a single capsule or in multiple capsule dosage form. In some embodiments, the pharmaceutical formulation is administered in two, or three, or four, capsules or tablets.

The pharmaceutical solid dosage forms described herein can comprise the co-crystal of the present invention as an API and one or more pharmaceutically acceptable additive(s) such as a compatible carrier, binder, complexing agent, ionic dispersion modulator, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof. In still other aspects, using standard coating procedures, such as those described in Remington's Pharmaceutical Sciences, 20th Edition (2000), a film coating is provided around the active agent(s) of the present invention formulation. In one embodiment, some or all of the active agent(s) of the present invention particles are coated. In another embodiment, some or all of the active agent(s) of the present invention particles are microencapsulated. In yet another embodiment, some or all of the active agent(s) of the present invention is amorphous material coated and/or microencapsulated with inert excipients. In still another embodiment, the active agent(s) of the present invention particles not microencapsulated and are uncoated.

Suitable carriers for use in the solid dosage forms described herein include, but are not limited to, acacia, gelatin, colloidal silicon dioxide, calcium glycerophosphate, calcium lactate, maltodextrin, glycerin, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose (e.g., Avicel®, Avicel® PH101, Avicel® PH102, Avicel® PH105, etc.), cellulose powder, dextrose, dextrates, dextrose, dextran, starches, pregelatinized starch, hydroxypropylmethylcellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

If needed, suitable disintegrants for use in the solid dosage forms described herein include, but are not limited to, natural starch such as corn starch or potato starch, a pregelatinized starch such as National 1551 or Amijel®, or a sodium starch glycolate such as Promogel® or Explotab®, a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, Ac-Di-Sol, methylcellulose, croscarmellose, or a cross-linked cellulose, such as cross-linked sodium carboxymethylcellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Binders impart cohesiveness to solid oral dosage form formulations: for powder-filled capsule formulation, they aid in plug formation that can be filled into soft or hard shell capsules and in tablet formulation, binders ensure that the tablet remains intact after compression and help assure blend uniformity prior to a compression or fill step. Materials suitable for use as binders in the solid dosage forms described herein include, but are not limited to, carboxymethylcellulose, methylcellulose (e.g., Methocel®), hydroxypropylmethylcellulose (e.g. Hypromellose USP Pharmacoat-603, hydroxypropylmethylcellulose acetate stearate (Aqoate HS-LF and HS), hydroxyethylcellulose, hydroxypropylcellulose (e.g., Klucel®), ethylcellulose (e.g., Ethocel®), and microcrystalline cellulose (e.g., Avicel®), microcrystalline dextrose, amylose, magnesium aluminum silicate, polysaccharide acids, bentonites, gelatin, polyvinylpyrrolidone/vinyl acetate copolymer, crosspovidone, povidone, starch, pregelatinized starch, tragacanth, dextrin, a sugar, such as sucrose (e.g., Dipac®), glucose, dextrose, molasses, mannitol, sorbitol, xylitol (e.g., Xylitab®), lactose, a natural or synthetic gum such as acacia, tragacanth, ghatti gum, mucilage of isapol husks, starch, polyvinylpyrrolidone (e.g., Povidone® CL, Kollidon® CL, Polyplasdone® XL-10, and Povidone® K-12), larch arabogalactan, Vecgum®, polyethylene glycol, waxes, sodium alginate, and the like. In general, binder levels of 20-70% are used in powder-filled gelatin capsule formulations. Binder usage level in tablet formulations is a function of whether direct compression, wet granulation, roller compaction, or usage of other excipients such as fillers which itself can act as moderate binders are used. Formulators skilled in the art can determine the binder level for the formulations, but binder usage level of up to 70% in tablet formulations is common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Non-water-soluble diluents are compounds typically used in the formulation of pharmaceuticals, such as calcium phosphate, calcium sulfate, starches, modified starches and microcrystalline cellulose, and micro cellulose (e.g., having a density of about 0.45 g/cm3, e.g. Avicel, powdered cellulose), and talc.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like. Wetting agents include surfactants.

Suitable surfactants for use in the solid dosage forms described herein include, for example, docusate and its pharmaceutically acceptable salts, sodium lauryl sulfate, sorbitan monooleate, polyoxyethylene sorbitan monooleate, polysorbates, poloxamers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 18000, vinylpyrrolidone/vinyl acetate copolymer (S630), sodium alginate, gums, such as, e.g., gum tragacanth and gum acacia, guar gum, xanthans, including xanthan gum, sugars, cellulosic, such as, e.g., sodium carboxymethylcellulose, methylcellulose, sodium carboxymethylcellulose, hydroxypropylmethylcellulose, hydroxyethylcellulose, polysorbate-80, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), butyl hydroxyanisole (BHIA), sodium ascorbate, Vitamin E TPGS, ascorbic acid, sorbic acid and tocopherol.

Immediate-release formulations may be prepared by combining super disintegrant such as Croscarmellose sodium and different grades of microcrystalline cellulose in different ratios. To aid disintegration, sodium starch glycolate will be added.

In cases where the two (or more) drugs included in the fixed-dose combinations of the present invention are incompatible, cross-contamination can be avoided, e.g., by incorporation of the drugs in different drug layers in the oral dosage form with the inclusion of a barrier layer(s) between the different drug layers, wherein the barrier layer(s) comprise one or more inert/non-functional materials.

The above-listed additives should be taken as merely examples and not limiting, of the types of additives that can be included in solid dosage forms of the present invention. The amounts of such additives can be readily determined by one skilled in the art, according to the particular properties desired.

Oral liquid dosage forms include, but are not limited to, solutions, emulsions, suspensions, and syrups. These oral liquid dosage forms may be formulated with any pharmaceutically acceptable excipient known to those of skill in the art for the preparation of liquid dosage forms. For example, water, glycerin, simple syrup, alcohol, and combinations thereof.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as but not limited to, an oil, water, an alcohol, and combinations of these pharmaceutically suitable surfactants, suspending agents, emulsifying agents, may be added for oral or parenteral administration. Suspensions may include oils. Such oils include, but are not limited to, peanut oil, sesame oil, cottonseed oil, corn oil, and olive oil. Suspensions may also contain esters of fatty acids such as ethyl oleate, isopropyl myristate, fatty acid glycerides, and acetylated fatty acid glycerides. Suspension formulations may include alcohols, such as, but not limited to, ethanol, isopropyl alcohol, hexadecyl alcohol, glycerol, and propylene glycol. Ethers, such as but not limited to, poly (ethylene glycol), petroleum hydrocarbons such as mineral oil and petrolatum; and water may also be used in suspension formulations.

In some embodiments, formulations are provided comprising the co-crystal of the present invention particles described herein and at least one dispersing agent or suspending agent for oral administration to a subject. The formulation may be a powder and/or granules for suspension, and upon admixture with water, a substantially uniform suspension is obtained. As described herein, the aqueous dispersion can comprise amorphous and non-amorphous the active agent(s) of the present invention particles of consisting of multiple effective particle sizes such that the active agent(s) of the present invention particles having a smaller effective particle size is absorbed more quickly and the active agent(s) of the present invention particles having a larger effective particle size are absorbed more slowly. In certain embodiments, the aqueous dispersion or suspension is an immediate-release formulation. In another embodiment, an aqueous dispersion comprising amorphous the active agent(s) of the present invention particles is formulated such that a portion of the active agent(s) of the present invention particles are absorbed within, e.g., about 3 hours after administration and about 90% of the active agent(s) of the present invention particles are absorbed within, e.g., about 10 hours after administration. In other embodiments, addition of a complexing agent to the aqueous dispersion results in a larger span of the active agent(s) of the present invention containing particles to extend the drug absorption phase such that 50-80% of the particles are absorbed in the first 3 hours and about 90% are absorbed by about 10 hours. Dosage forms for oral administration can be aqueous suspensions selected from the group including, but not limited to, pharmaceutically acceptable aqueous oral dispersions, emulsions, solutions, and syrups. See, e.g., Singh et al., Encyclopedia of Pharmaceutical Technology, 2nd Ed., pp. 754-757 (2002). In addition to the active agent(s) of the present invention particles, the liquid dosage forms may comprise additives, such as (a) disintegrating agents; (b) dispersing agents; (c) wetting agents; (d) at least one preservative, (e) viscosity enhancing agents, (f) at least one sweetening agent, and (g) at least one flavoring agent.

Examples of disintegrating agents for use in the aqueous suspensions and dispersions include, but are not limited to, a starch, e.g., a natural starch such as corn starch or potato starch, a pregelatinized starch such as National 1551 or Amijel®, or sodium starch glycolate such as Promogel® or Explotab®; a cellulose such as a wood product, microcrystalline cellulose, e.g., Avicel®, Avicel® PH101, Avicel® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sol®), cross-linked carboxymethylcellulose, or cross-linked croscarmellose; a cross-linked starch such as sodium starch glycolate; a cross-linked polymer such as crosspovidone; a cross-linked polyvinylpyrrolidone; alginate such as alginic acid or a salt of alginic acid such as sodium alginate; a clay such as Veegum® HV (magnesium aluminum silicate); a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein are known in the art and include, for example, hydrophilic polymers, electrolytes, Tween® 60 or 80, PEG, polyvinylpyrrolidone (PVP; commercially known as Plasdone®), and the carbohydrate-based dispersing agents such as, for example, hydroxypropylcellulose and hydroxypropylcellulose ethers (e.g., HPC, HPC-SL, and HPC-L), hydroxypropylmethylcellulose and hydroxypropylmethylcellulose ethers (e.g. HPMC K100, HPMC K4M, HPMC K15M, and HPMC K100M), carboxymethylcellulose sodium, methylcellulose, hydroxyethylcellulose, hydroxypropylmethylcellulose phthalate, hydroxypropylmethylcellulose acetate stearate, noncrystalline cellulose, magnesium aluminum silicate, triethanolamine, polyvinyl alcohol (PVA), polyvinylpyrrolidone/vinyl acetate copolymer (Plasdone®, e.g., S-630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)). In other embodiments, the dispersing agent is selected from a group not comprising one of the following agents: hydrophilic polymers; electrolytes; Tween® 60 or 80; PEG; polyvinylpyrrolidone (PVP); hydroxypropyl cellulose and hydroxypropyl cellulose ethers (e.g., HPC, HPC-SL, and HPC-L); hydroxypropyl methylcellulose and hydroxypropyl methylcellulose ethers (e.g. HPMC K100, HPMC K4M, HPMC K15M, HPMC K100M, and Pharmacoat® USP 2910 (Shin-Etsu)); carboxymethylcellulose sodium; methylcellulose; hydroxyethylcellulose; hydroxypropylmethylcellulose phthalate; hydroxypropylmethylcellulose acetate stearate; non-crystalline cellulose; magnesium aluminum silicate; triethanolamine; polyvinyl alcohol (PVA); 4-(1,1,3,3-tetramethyl butyl)-phenol polymer with ethylene oxide and formaldehyde; poloxamers (e.g., Pluronics F68®, F88®, and F108®, which are block copolymers of ethylene oxide and propylene oxide); or poloxamines (e.g., Tetronic 908®, also known as Poloxamine 908®).

Wetting agents (including surfactants) suitable for the aqueous suspensions and dispersions described herein are known in the art and include, but are not limited to, acetyl alcohol, glycerol monostearate, polyoxyethylene sorbitan fatty acid esters (e.g., the commercially available Tweens® such as e.g., Tween 20® and Tween 80® (ICI Specialty Chemicals)), and polyethylene glycols (e.g., Carbowaxs 3350® and 1450®, and Carpool 934® (Union Carbide)), oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphatidylcholine and the like.

Suitable preservatives for the aqueous suspensions or dispersions described herein include, for example, potassium sorbate, parabens (e.g., methylparaben and propylparaben) and their salts, benzoic acid and its salts, other esters of para hydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

In one embodiment, the aqueous liquid dispersion can comprise methylparaben and propylparaben in a concentration ranging from about 0.01% to about 0.3% methylparaben by weight to the weight of the aqueous dispersion and about 0.005% to about 0.03% propylparaben by weight to the total aqueous dispersion weight. In yet another embodiment, the aqueous liquid dispersion can comprise methylparaben from about 0.05 to about 0.1 weight % and propylparaben from about 0.01 to about 0.02 weight % of the aqueous dispersion.

Suitable viscosity enhancing agents for the aqueous suspensions or dispersions described herein include, but are not limited to, methyl cellulose, xanthan gum, carboxymethylcellulose, hydroxypropyl cellulose, hydroxypropylmethyl cellulose, Plasdone® S-630, carbomer, polyvinyl alcohol, alginates, acacia, chitosans and combinations thereof. The concentration of the viscosity-enhancing agent will depend upon the agent selected and the viscosity desired.

In addition to the additives listed above, the liquid the active agent(s) of the present invention formulations can also comprise inert diluents commonly used in the art, such as water or other solvents, solubilizing agents, emulsifiers, and/or sweeteners.

The formulations suitable for intramuscular, subcutaneous, or intravenous injection may comprise physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles including water, ethanol, polyols (propylene glycol, polyethylene-glycol, glycerol, cremophor and the like), suitable mixtures thereof, vegetable oils (such as olive oil) and injectable organic esters such as ethyl oleate. Additionally, the active agent(s) of the present invention can be dissolved at concentrations of >1 mg/ml using water-soluble beta cyclodextrins (e.g. beta-sulfobutyl-cyclodextrin and 2-hydroxypropylbetacyclodextrin. Proper fluidity can be maintained, for example, by the use of a coating such as a lecithin, by the maintenance of the required particle size in the case of dispersions, and by the use of surfactants. The active agent(s) of the present invention formulations suitable for subcutaneous injection may also contain additives such as preserving, wetting, emulsifying, and dispensing agents. Prevention of the growth of microorganisms can be ensured by various antibacterial and antifungal agents, such as parabens, benzoic acid, benzyl alcohol, chlorobutanol, phenol, sorbic acid, and the like. It may also be desirable to include isotonic agents, such as sugars, sodium chloride, and the like. Prolonged drug absorption of the injectable pharmaceutical form can be brought about by the use of agents delaying absorption, such as aluminum monostearate and gelatin. The active agent(s) of the present invention suspension formulations designed for extended-release via subcutaneous or intramuscular injection can avoid first-pass metabolism and lower dosages of the active agent(s) of the present invention will be necessary to maintain plasma levels of about 50 ng/ml. In such formulations, the particle size of the active agent(s) of the present invention particles and the range of the particle sizes of the active agent(s) of the present invention particles can be used to control the release of the drug by controlling the rate of dissolution in fat or muscle.

In still other embodiments, effervescent powders containing at least one co-crystal of the invention may be prepared. Effervescent salts have been used to disperse medicines in water for oral administration. Effervescent salts are granules or coarse powders containing a medicinal agent in a dry mixture, usually composed of sodium bicarbonate, citric acid and/or tartaric acid. When salts of the present invention are added to water, the acids and the base react to liberate carbon dioxide gas, thereby causing "effervescence." Examples of effervescent salts include e.g: sodium bicarbonate or a mixture of sodium bicarbonate and sodium carbonate, citric acid and/or tartaric acid. Any acid-base combination that results in the liberation of carbon dioxide can be used in place of the combination of sodium bicarbonate and citric and tartaric acids, as long as the ingredients were suitable for pharmaceutical use and result in a pH of about 6.0 or higher.

In other embodiments, a powder comprising the co-crystal of the present invention formulations described herein may be formulated to comprise one or more pharmaceutical excipients and flavors. Such a powder may be prepared, for example, by mixing the active agent(s) of the present invention formulation and optional pharmaceutical excipients to form a bulk blend composition. Additional embodiments also comprise a suspending agent and/or a wetting agent. This bulk blend is uniformly subdivided into unit dosage packaging or multi-dosage packaging units. The term "uniform" means the homogeneity of the bulk blend is substantially maintained during the packaging process.

In certain embodiments of the present invention, pharmaceutical compositions may be formulated into a dosage form suitable for parenteral use. For example, the dosage form may be a lyophilized powder, a solution, suspension (e.g., depot suspension).

In other embodiments, pharmaceutical compositions may be formulated into a topical dosage form such as, but not limited to, a patch, a gel, a paste, a cream, an emulsion, liniment, balm, lotion, and ointment.

Tablets of the invention described here can be prepared by methods well known in the art. Various methods for the preparation of the immediate release, modified release, controlled release, and extended-release dosage forms (e.g., as matrix tablets, tablets having one or more modified, controlled, or extended-release layers, etc.) and the vehicles therein are well known in the art. Generally recognized compendium of methods include: Remington: The Science and Practice of Pharmacy, Alfonso R. Gennaro, Editor, 20th Edition, Lippincott Williams & Wilkins, Philadelphia, PA; Sheth et al. (1980) Compressed tablets, in Pharmaceutical dosage forms, Vol 1, edited by Lieberman and Lachtman, Dekker, NY.

In certain embodiments, solid dosage forms, e.g., tablets, effervescent tablets, and capsules, are prepared by mixing the active agent(s) of the present invention particles with one or more pharmaceutical excipients to form a bulk blend composition. When referring to these bulk blend compositions as homogeneous, it is meant that the active agent(s) of the present invention particles are dispersed evenly throughout the composition so that the composition may be readily subdivided into equally effective unit dosage forms, such as tablets, pills, and capsules. The individual unit dosages may also comprise film coatings, which disintegrate upon oral ingestion or upon contact with diluents. These the active agent(s) of the present invention formulations can be manufactured by conventional pharmaceutical techniques.

Conventional pharmaceutical techniques for preparation of solid dosage forms include, e.g., one or a combination of methods: (1) dry mixing, (2) direct compression, (3) milling, (4) dry or non-aqueous granulation, (5) wet granulation, or (6) fusion. Sec, e.g., Lachman et al., Theory and Practice of Industrial Pharmacy (1986). Other methods include, e.g., spray drying, pan coating, melt granulation, granulation, fluidized bed spray drying or coating (e.g., Wurster coating), tangential coating, top spraying, tableting, extruding and the like.

Compressed tablets are solid dosage forms prepared by compacting the bulk blend the active agent(s) of the present invention formulations described above. In various embodiments, compressed tablets which are designed to dissolve in the mouth will comprise one or more flavoring agents. In other embodiments, the compressed tablets will comprise a film surrounding the final compressed tablet. In some embodiments, the film coating can provide a delayed release of the active agent(s) of the present invention formulation. In other embodiments, the film coating aids in patient compliance (e.g., Opadry® coatings or sugar coating). Film coatings comprising Opadry® typically range from about 1% to about 3% of the tablet weight. Film coatings for delayed-release usually comprise 2-6% of a tablet weight or 7-15% of a spray-layered bead weight. In other embodiments, the compressed tablets comprise one or more excipients.

A capsule may be prepared, e.g., by placing the bulk blend of co-crystals of the present invention formulation, described above, inside of a capsule. In some embodiments, the co-crystals are placed in a soft gelatin capsule. In other embodiments, the co-crystals are placed in standard gelatin capsules or non-gelatin capsules such as capsules comprising HPMC. In other embodiments, the co-crystals of the present invention formulations are placed in a sprinkle capsule, wherein the capsule may be swallowed whole or the capsule may be opened and the contents sprinkled on food prior to eating. In some embodiments of the present invention, the therapeutic dose is split into multiple (e.g., two, three, or four) capsules. In some embodiments, the entire dose of the active agent(s) of the present invention formulation is delivered in a capsule form. For example, the capsule may comprise between about 100 mg to about 1000 mg of the active agent(s) of the present invention.

In certain preferred embodiments, the formulations of the present invention are fixed-dose combinations of a co-crystal comprising itanapraced and at least one drug which can prevent, inhibit or treat a coronavirus infection in a human by a similar or different mechanism than the praced drug. Fixed-dose combination formulations may contain the following combinations in the form of single-layer monolithic tablet or multi-layered monolithic tablet or in the form of a core tablet-in-tablet or multi-layered multi-disk tablet or beads inside a capsule or tablets inside a capsule but not limited to: (a) therapeutically efficacious fixed-dose combinations of immediate-release formulations; (b) therapeutically efficacious fixed-dose combinations of immediate release and extended-release drugs contained in a single dosage form; (c) therapeutically efficacious fixed-dose combinations of extended-release formulations of the drug(s).

The pharmaceutical compositions described herein can be formulated into any suitable dosage form, including but not limited to, aqueous oral dispersions, aqueous oral suspensions, solid dosage forms including oral solid dosage forms, aerosols, controlled release formulations, fast melt formulations, effervescent formulations, self-emulsifying dispersions, solid solutions, liposomal dispersions, lyophilized formulations, tablets, capsules, pills, powders, delayed-release formulations, immediate-release formulations, modified release formulations, extended-release formulations, pulsatile release formulations, multi particulate formulations, and mixed immediate release and controlled release formulations. In some embodiments, the co-crystals of the present invention formulations provide a therapeutically effective amount of the active agent(s) of the present invention over an interval of about 30 minutes to about 24 hours after administration, enabling, for example, a four times a day (Q.I.D.), a three times a day (t.i.d.), a twice-a-day (b.i.d.), or a once-a-day (q.d.) administration. The dosage form comprises co-crystals and a sufficient amount of a controlled release agent admixed with and/or coating the co-crystal to provide a desired in-vitro release profile and render the dosage form suitable, e.g., for a four time a day, a three times a day, a two times a day, or a once-a-day administration. In one embodiment, the co-crystals formulated into a controlled release or pulsatile solid dosage form for twice-a-day administration. In other embodiments, the co-crystals of the present invention are dispersed in aqueous dispersion for twice-a-day administration. Generally speaking, one will desire to administer an amount of the co-crystals of the present invention that is effective to achieve a plasma level commensurate with the concentrations found to be effective in vivo for a period of time effective to elicit a desired therapeutic effect.

Depending on the desired release profile, the oral solid dosage forms of the present invention may contain a suitable amount of controlled-release agents, extended-release agents, and/or modified-release agents (e.g., delayed-release agents). The pharmaceutical solid oral dosage forms comprising the active agent(s) of the present invention described herein can be further formulated to provide a modified or controlled release of the active agent(s) of the present invention. In some embodiments, the solid dosage forms described herein can be formulated as a delayed release dosage form such as and enteric-coated delayed release oral dosage forms, i.e., as an oral dosage form of a pharmaceutical composition as described herein which utilizes an enteric coating to affect release in the small intestine of the gastrointestinal tract. The enteric-coated dosage form may be a compressed or molded or extruded tablet/mold (coated or uncoated) containing granules, powder, pellets, beads or particles of the active ingredient and/or other composition components, which are themselves coated or uncoated. The enteric coated oral dosage form may also be a capsule (coated or uncoated) containing pellets, beads or granules of the solid carrier or the composition, which are themselves coated or uncoated. Enteric coatings may also be used to prepare other controlled release dosage forms including extended-release and pulsatile release dosage forms.

In other embodiments, the active agent(s) of the formulations described herein are delivered using a pulsatile dosage form. Pulsatile dosage forms comprising the active agent(s) of the present invention formulations described herein may be administered using a variety of formulations known in the art. For example, such formulations include, but are not limited to, those described in U.S. Pat. Nos. 5,011,692, 5,017,381, 5,229,135, and 5,840,329, each of which is specifically incorporated by reference. Other dosage forms suitable for use with the active agent(s) of the present invention formulations are described in, for example, U.S. Pat. Nos. 4,871,549, 5,260,068, 5,260,069, 5,508,040, 5,567,441 and 5,837,284, all of which are specifically incorporated by reference. In one embodiment, the controlled release dosage form is pulsatile release solid oral dosage form comprising at least two groups of particles, each containing active agent(s) of the present invention as described herein. The first group of particles provides a substantially immediate dose of the active agent(s) of the present invention upon ingestion by a subject. The first group of particles can be either uncoated or comprise a coating and/or sealant. The second group of particles comprises coated particles, which may comprise from about 2% to about 75%, preferably from about 2.5% to about 70%, or from about 40% to about 70%, by weight of the total dose of the active agent(s) of the present invention in said formulation, in admixture with one or more binders.

Coatings for providing a controlled, delayed, or extended-release may be applied to the drug(s) or to a core containing the drug(s). The coating may comprise a pharmaceutically acceptable ingredient in an amount sufficient, e.g., to provide a delay of from about 2 hours to about 7 hours following ingestion before release of the second dose. Suitable coatings include one or more differentially degradable coatings such as, by way of example only, pH-sensitive coatings (enteric coatings) such as acrylic resins (e.g., Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® S12.5, and Eudragit® NE30D, Eudragit® NE 40DR) either alone or blended with cellulose derivatives, e.g., ethylcellulose, or non-enteric coatings having variable thickness to provide differential release of the active agent(s) of the present invention formulation.

Many other types of controlled/delayed/extended-release systems known to those of ordinary skill in the art and are suitable for use with the active agent(s) of the present invention formulations described herein. Examples of such delivery systems include, e.g., polymer-based systems, such as polylactic and polyglycolic acid, polyanhydrides and polycaprolactone, cellulose derivatives (e.g., ethylcellulose), porous matrices, nonpolymer-based systems that are lipids, including sterols, such as cholesterol, cholesterol esters and fatty acids, or neutral fats, such as mono-, di- and triglycerides; hydrogel release systems; silastic systems; peptide-based systems; wax coatings, bioerodible dosage forms, compressed tablets using conventional binders and the like. Scc, e.g., Liberman et al., Pharmaceutical Dosage Forms, 2 Ed., Vol. 1, pp. 209-214 (1990); Singh et al., Encyclopedia of Pharmaceutical Technology, 2nd Ed., pp. 751-753 (2002); U.S. Pat. Nos. 4,327,725, 4,624,848, 4,968,509, 5,461,140, 5,456,923, 5,516,527, 5,622,721, 5,686,105, 5,700,410, 5,977,175, 6,465,014 and 6,932,983, each of which is specifically incorporated by reference. In certain embodiments, the controlled release systems may comprise the controlled/delayed/extended-release material incorporated with the drug(s) into a matrix, whereas in other formulations, the controlled release material may be applied to a core containing the drug(s). In certain embodiments, one drug may be incorporated into the core while the other drug is incorporated into the coating. In some embodiments, materials include shellac, acrylic polymers, cellulosic derivatives, polyvinyl acetate phthalate, and mixtures thereof. In other embodiments, materials include Eudragit® series E, L, RL, RS, NE, L, L300, S, 100-55, cellulose acetate phthalate, Aquateric, cellulose acetate trimellitate, ethyl cellulose, hydroxypropylmethylcellulose phthalate, hydroxypropylmethylcellulose acetate succinate, polyvinyl acetate phthalate, and Cotteric. The controlled/delayed/extended-release systems may utilize a hydrophilic polymer, including but not limited to a water-swellable polymer (e.g., a natural or synthetic gum). The hydrophilic polymer may be any pharmaceutically acceptable polymer which swells and expands in the presence of water to slowly release the active agent(s) of the present invention. These polymers include polyethylene oxide, methylcellulose, hydroxypropyl cellulose, hydroxypropylmethylcellulose, and the like.

The performance of acrylic polymers (primarily their solubility in biological fluids) can vary based on the degree and type of substitution. Examples of suitable acrylic polymers which may be used in matrix formulations or coatings include methacrylic acid copolymers and ammonia methacrylate copolymers. The Eudragit series E, L, S, RL, RS and NE (Rohm Pharma) are available as solubilized in an organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in the stomach and dissolve in the intestine; Opadry Enteric is also insoluble in the stomach and dissolves in the intestine.

Examples of suitable cellulose derivatives for use in matrix formulations or coatings include ethyl cellulose; reaction mixtures of partial acetate esters of cellulose with phthalic anhydride. The performance can vary based on the degree and type of substitution. Cellulose acetate phthalate (CAP) dissolves in pH >6. Aquateric (FMC) is an aqueous-based system and is a spray-dried CAP psuedolatex with particles <1 µm. Other components in Aquateric can include pluronic, Tweens, and acetylated monoglycerides. Other suitable cellulose derivatives include cellulose acetate trimellitate (Eastman); methylcellulose (Pharmacoat, Methocel); hydroxypropylmethylcellulose phthalate (HPMCP); hydroxypropylmethylcellulose succinate (HPMCS); and hydroxypropylmethylcellulose acetate succinate (e.g., AQOAT (Shin Etsu)). The performance can vary based on the degree and type of substitution. For example, HPMCP such as, HP-50, HP-55, HP-55S, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules or as fine powders for aqueous dispersions. Other suitable cellulose derivatives include hydroxypropylmethylcellulose.

In some embodiments, the coating may contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate, and triacetin. Conventional coating techniques such as spray or pan coating are employed to apply coatings. The coating thickness must be sufficient to ensure that the oral dosage form remains intact until the desired site of topical delivery in the intestinal tract is reached.

Extended-release multi-layered matrix tablets may be prepared by using fixed-dose combinations of a drug(s) from Group 1 together with a drug(s) from Group 2. Such formulations may comprise one or more of the drugs within a hydrophilic or hydrophobic polymer matrix. For example, a hydrophilic polymer may comprise guar gum, hydroxypropylmethylcellulose, and xanthan gum as matrix formers. Lubricated formulations may be compressed by a wet granulation method.

Multilayer tablet delivery (e.g., such as that used in the GeoMatrix™ technology) comprises a hydrophilic matrix core containing the active ingredient and one or two impermeable or semi-permeable polymeric coatings. This technology uses films or compressed polymeric barrier coatings on one or both sides of the core. The presence of polymeric coatings (e.g., such as that used in the GeoMatrix™ technology) modifies the hydration/swelling rates of the core and reduces the surface area available for drug release. These partial coatings provide modulation of the drug dissolution profile: they reduce the release rate from the device and shift the typical time-dependent release rate towards constant release. This technology enables customized levels of controlled release of specific drugs and/or simultaneous release of two different drugs at different rates that can be achieved from a single tablet. The combination of layers, each with different rates of swelling, gelling and erosion, is used for the rate of drug release in the body. Exposure of the multilayer tablet as a result of the partial coating may affect the release and erosion rates, therefore, transformation of a multilayered tablet with exposure on all sides to the gastrointestinal fluids upon detachment of the barrier layer will be considered.

Multi-layered tablets containing combinations of immediate release and modified/extended release of two different drugs or dual release rate of the same drug in a single dosage form may be prepared by using hydrophilic and hydrophobic polymer matrices.

Dual release repeat action multi-layered tablets may be prepared with an outer compression layer with an initial dose of rapidly disintegrating matrix in the stomach and a core inner layer tablet formulated with components that are insoluble in the gastric media but release efficiently in the intestinal environment.

In one embodiment, the dosage form is a solid oral dosage form which is an immediate release dosage form whereby >80% of the active agent(s) of the present invention particles hours after administration. In other embodiments, the invention provides an (e.g., solid oral) dosage form that is a controlled release or pulsatile release dosage form. In such instances, the release may be, e.g., 30 to 60% of the active agent(s) of the present invention particles by weight are released from the dosage form within about 2 hours after administration and about 90% by weight of the active agent(s) of the present invention released from the dosage form, e.g., within about 7 hours after administration. In yet other embodiments, the dosage form includes at least one active agent in an immediate-release form and at least one active agent in the delayed-release form, or sustained-release form. In yet other embodiments, the dosage form includes at least two active agents that are released at different rates as determined by in-vitro dissolution testing or via oral administration.

The various release dosage formulations discussed above and others known to those skilled in the art can be characterized by their disintegration profile. A profile is characterized by the test conditions selected. Thus the disintegration profile can be generated at a pre-selected apparatus type, shaft speed, temperature, volume, and pH of the dispersion media. Several disintegration profiles can be obtained. For example, a first disintegration profile can be measured at a pH level approximating that of the stomach (about pH 1.2); a second disintegration profile can be measured at a pH level approximating that of one point in the intestine or several pH levels approximating multiple points in the intestine (about 6.0 to about 7.5, more specifically, about 6.5 to 7.0). Another disintegration profile can be measured using distilled water. The release of formulations may also be characterized by their pharmacokinetic parameters, for example, Cmax, Tmax, and AUC (0-t).

In certain embodiments, the controlled, delayed or extended-release of one or more of the drugs of the fixed-dose combinations of the invention may be in the form of a capsule having a shell comprising the material of the rate-limiting membrane, including any of the coating materials previously discussed, and filled with the active agent(s) of the present invention particles. A particular advantage of this configuration is that the capsule may be prepared independently of the active agent(s) of the present invention particles; thus process conditions that would adversely affect the drug can be used to prepare the capsule. Alternatively, the formulation may comprise a capsule having a shell made of a porous or a pH-sensitive polymer made by a thermal forming process. Another alternative is a capsule shell in the form of an asymmetric membrane; i.e., a membrane that has a thin skin on one surface and most of whose thickness is constituted of a highly permeable porous material. The asymmetric membrane capsules may be prepared by a solvent exchange phase inversion, wherein a solution of polymer, coated on a capsule-shaped mold, is induced to phase-separate by exchanging the solvent with a miscible non-solvent. In another embodiment, spray layered active agent(s) of the present invention particles are filled in a capsule. An exemplary process for manufacturing the spray layered the active agent(s) of the present invention is the fluidized bed spraying process. The active agent(s) of the present invention suspensions or the active agent(s) of the present invention complex suspensions described above may be sprayed onto sugar or microcrystalline cellulose (MCC) beads (20-35 mesh) with Wurster column insert at an inlet temperature of 50° C. to 60° C. and air temp of 30° C. to 50° C. A 15 to 20 wt % total solids content suspension containing 45 to 80 wt % the active agent(s) of the present invention, 10 to 25 wt % hydroxymethylpropylcellulose, 0.25 to 2 wt % of SLS, 10 to 18 wt % of sucrose, 0.01 to 0.3 wt % simethicone emulsion (30% emulsion) and 0.3 to 10% NaCl, based on the total weight of the solid content of the suspension, are sprayed (bottom spray) onto the beads through 1.2 mm nozzles at 10 mL/min and 1.5 bar of pressure until a layering of 400 to 700% wt % is achieved as compared to initial beads weight. The resulting spray layered the active agent(s) of the present invention particles or the active agent(s) of the present invention complex particles comprise about 30 to 70 wt % of the active agent(s) of the present invention based on the total weight of the particles. In one embodiment the capsule is a size 0 soft gelatin capsule. In one embodiment, the capsule is a swelling plug device. In another embodiment, the swelling plug device is further coated with cellulose acetate phthalate or copolymers of methacrylic acid and methylmethacrylate. In some embodiments, the capsule includes at least 100 mg (or at least 300 mg or at least 400 mg) the active agent(s) of the present invention and has a total weight of less than 800 mg (or less than 700 mg). The capsule may contain a plurality of the active agent(s) of the present invention-containing beads, for example, spray layered beads. In some embodiments, the beads are 12-25% the active agent(s) of the present invention by weight. In some embodiments, some or all of the active agent(s) of the present invention containing beads are coated with a coating comprising 6 to 15% (or 8 to 12%) of the total bead weight. Optimization work typically involves lower loading levels and the beads constitute 30 to 60% of the finished bead weight. The capsule may contain a granulated composition, wherein the granulated composition comprises the active agent(s) of the present invention.

The capsule may provide pulsatile release the active agent(s) of the present invention oral dosage form. Such formulations may comprise: (a) a first dosage unit comprising a first the active agent(s) of the present invention dose that is released substantially immediately following oral administration of the dosage form to a patient; (b) a second dosage unit comprising a second the active agent(s) of the present invention dose that is released approximately 3 to 7 hours following administration of the dosage form to a patient. For pulsatile release capsules containing beads, the beads can be coated with a coating comprising 6 to 15% (or 8 to 12%) of the total bead weight. In some embodiments, the coating is a coating that is insoluble at pH 1 to 2 and soluble at pH greater than 5.5. In certain embodiments, the formulation may comprise a pulsatile release capsule comprising at least two active agents (e.g., one drug from Group 1 and one drug from Group 2). This pulsatile release capsule may contain a plurality of beads in which some beads are immediate-release beads and other beads are formulated, for example with the use of a coating, for modified release, typically from about 3 to about 10 hours after administration. In other embodiments, the pulsatile release capsule contains a plurality of beads formulated for modified release and the active agent(s) of the present invention powder, for example, spray granulated the active agent(s) of the present invention, for immediate release.

In some embodiments, the release of the active agent(s) of the present invention particles can be modified with a modified release coating, such as an enteric coating using cellulose acetate phthalate or a sustained release coating comprising copolymers of methacrylic acid and methylmethacrylate. In one embodiment, the enteric coating may be present in an amount of about 0.5 to about 15 wt %, more specifically, about 8 to about 12 wt %, based on the weight of, e.g., the spray layered particles. In one embodiment, the spray layered particles coated with the delayed and/or sustained release coatings can be filled in a modified release capsule in which both enteric-coated and immediate release the active agent(s) of the present invention beads are filled into a soft gelatin capsule. Additional suitable excipients may also be filled with the coated particles in the capsule. The uncoated particles release the active agent(s) of the present invention immediately upon administration while the coated particles do not release the active agent(s) of the present invention until these particles reach the intestine. By controlling the ratios of the coated and uncoated particles, desirable pulsatile release profiles may be obtained. In some embodiments, the ratios between the uncoated and the coated particles are e.g., 20/80, or 30/70, or 40/60, or 50/50, w/w to obtain desirable release.

In certain embodiments, the drugs contained in a fixed-dose combination of the present invention may be in the form of beads contained within a capsule. In certain embodiments, some beads may release one or both drugs immediately, while other beads would release one or both drugs over an extended period of time or after a delay (delayed-release).

In certain embodiments, spray layered active agent(s) of the present invention particles can be compressed into tablets with commonly used pharmaceutical excipients. Any appropriate apparatus for forming the coating can be used to make the enteric coated tablets, e.g., fluidized bed coating using a Wurster column, powder layering in coating pans or rotary coaters; dry coating by double compression technique; tablet coating by film coating technique, and the like. Sec, e.g., U.S. Pat. No. 5,322,655; Remington's Pharmaceutical Sciences Handbook: Chapter 90 "Coating of Pharmaceutical Dosage Forms", 1990. In certain embodiments, the spray layered the active agent(s) of the present invention described above and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the active agent(s) of the present invention formulation into the gastrointestinal fluid. In other embodiments, the spray layered the active agent(s) of the present invention particles or spray layered the active agent(s) of the present invention complex particles with enteric coatings described above and one or more excipients are dry blended and compressed into a mass, such as a tablet. In one embodiment, the enteric-coated particles in the tablet substantially avoid the release of the active agent(s) of the present invention, for example, less than 15 wt %, in the stomach but releases substantially all the active agent(s) of the present invention (enterically or sustained-release coated), for example, greater than 80 wt %, in the intestine.

In certain embodiments, a pulsatile release the active agent(s) of the present invention formulation comprises a first dosage unit comprising a formulation made from the active agent(s) of the present invention containing granules made from a spray drying or spray granulated procedure or a formulation made from the active agent(s) of the present invention complex containing granules made from a spray drying or spray granulated procedure without enteric or sustained-release coatings and a second dosage unit comprising spray layered the active agent(s) of the present invention particles or spray layered the active agent(s) of the present invention complex particles with enteric or sustained-release coatings. In one embodiment, the first dosage unit and the second dosage unit are wet or dry blended and compressed into a mass to make a pulsatile release tablet.

In certain embodiments, binding, lubricating and disintegrating agents are blended (wet or dry) to the spray layered the active agent(s) of the present invention to make a compressible blend. The first and second dosage units are compressed separately and then compressed together to form a bilayer tablet. In yet another embodiment, the first dosage unit is in the form of an overcoat and completely covers the second dosage unit.

In certain embodiments, ingredients (including or not including the active agent(s)) of the invention are wet granulated. The individual steps in the wet granulation process of tablet preparation include milling and sieving of the ingredients, dry powder mixing, wet massing, granulation, drying, and final grinding. In various embodiments, the active agent(s) of the present invention composition is added to the other excipients of the pharmaceutical formulation after they have been wet granulated. Alternatively, the ingredients may be subjected to dry granulation, e.g., via compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). No wet binder or moisture is involved in any of the steps. In some embodiments, the active agent(s) of the present invention formulation is dry granulated with other excipients in the pharmaceutical formulation. In other embodiments, the active agent(s) of the present invention formulation is added to other excipients of the pharmaceutical formulation after they have been dry granulated.

In other embodiments, the formulation of the present invention formulations described herein is a solid dispersion. Methods of producing such solid dispersions are known in the art and include, but are not limited to, for example, U.S. Pat. Nos. 4,343,789, 5,340,591, 5,456,923, 5,700,485, 5,723,269, and U.S. Pub. Appl. 2004/0013734, each of which is specifically incorporated by reference. In some embodiments, the solid dispersions of the invention comprise both amorphous and non-amorphous the active agent(s) of the present invention and can have enhanced bioavailability as compared to conventional the active agent(s) of the present invention formulations. In still other embodiments, the active agent(s) of the present invention formulations described herein are solid solutions. Solid solutions incorporate a substance together with the active agent and other excipients such that heating the mixture results in the dissolution of the drug and the resulting composition is then cooled to provide a solid blend that can be further formulated or directly added to a capsule or compressed into a tablet.

The pharmaceutical agents which make up the combination therapy disclosed herein may be a combined dosage form or in separate dosage forms intended for substantially simultaneous administration. The pharmaceutical agents that make up the combination therapy may also be administered sequentially, with either therapeutic compound being administered by a regimen calling for two-step administration.

Covid-19

Various reports indicate that a significant proportion of patients with COVID-19 show neurologic symptoms, such as headache, nausea, vomiting as well as loss of taste and smell and in rare cases even encephalitis (Li, 2020; Yeager 2020; Filatov, 2020). It is believed that these neurologic symptoms indicate that the virus may also invade the central nervous system such as was previously reported for SARS-COV or MERS. The route by which the viruses enter the CNS is still not known but there is increasing evidence that they may first invade peripheral nerve terminals, and then gain access to the CNS via transsynaptic transfer (Li 2012, 2013).

The consequent neurological damage caused by a coronavirus such as COVID-19 has the potential to exacerbate lung damage in two ways: First, some coronaviruses have been demonstrated able to spread to the medullary cardio-respiratory center in the brain stem causing damage that could interfere with control of respiratory function. Second, we believe, by releasing cytokines and other toxins into the blood circulation, which then lodge in the lungs contributing to Acute Respiratory Stress Syndrome (ARDS) from which COVID-19 patients often die.

A similar mechanism has been proposed to account for the large proportion (20-30%) of ARDS in patients who have suffered traumatic brain injury (TBI) where ensuing damage to the blood brain barrier (BBB) leads to acute release of a variety of factors, including proinflammatory immune cells, cytokines and toxins, released from hyperactivated or injured microglia, astrocytes and neurons (Hu, 2017; Puntambekar, 2018). The brain similarly orchestrates a complex immunological tissue reaction to coronavirus infection (Bergman, 2006). A recent report indicates that microglia in particular are essential for protection against coronavirus induced encephalitis (Wheeler, 2018).

Example 1

Instruments and Experimental Details
X-Ray Powder Diffractometer (XRPD)

X-ray powder diffraction analyses are obtained using a BRUKER D8 ADVANCE equipped with a Cu radiation source operated at 40 kV and 40 mA (2=1.54 Å after Ni filtering) configured in a Bragg-Brentano geometry, equipped with a 90-position AUTO-CHANGER and a silicon strip detector (SSD160-2). A coupled theta-two theta continuous PSD (Position Sensitive Device) fast scan from 4 to 40 degrees are collected over approximately 32 minutes (0.5 sec/0.01° step). A sample is placed onto a polished zero-background silicon wafer by gently distributing onto the flat surface and is analyzed as a flat plate specimen.
Differential Scanning Calorimeter (DSC)

DSC runs are generated on a TA Instruments DSC 2500 equipped with an auto-sampler and RCS90. Typically, 1-3 mg of sample in a Tzero hermetically sealed aluminum pan is heated at 10° C. per minute ramp rate from either −80° C. or near ambient temperature to around the degradation onset as determined by TGA in T4P mode is used. A purge of dry nitrogen at 50 mL/min is maintained over the sample during the experiment. The instrument control and data analysis are operated under TRIOS software.

Thermogravimetric Analyzer (TGA)

TGA data are collected using a TA Instruments Discovery TGA equipped with an autosampler. Typically, 2-5 mg of sample is placed in a pre-tared, Tzero aluminum pan either as a hermetically sealed pan which would be automatically punched open before sample loading for analysis, or as an open pan. A 10° C. per minute ramp rate from ambient temperature to 375° C. using a 25 mL/min nitrogen purge is used. The instrument control and data analysis are operated under TRIOS software.
Dynamic Vapor Sorption (DVS)

Samples are analyzed using a TA Instruments Q5000SA gravimetric water sorption analyzer. The relative humidity (RH) is adjusted in 10% RH increments between 5-95% (±1% RH) at 25° C. (±0.5°° C.). The mass of a sample is continuously monitored and recorded with respect to RH and time with criteria for mass equilibrium set as a percent mass change <0.0100 for 5 minutes with a time limit of 720 minutes per step. The humidity is controlled by mixing dry and wet nitrogen streams with a total flow rate of 200 mL/min. The instrument control and data analysis are operated under Advantage for Q Series and Universal Analysis software, respectively.
Polarized Light Optical Microscope (PLM)

Samples are analyzed using a Nikon Eclipse LV100N POL polarized light microscope equipped with a FLIR Grasshopper3, 3.2 MP, 121 FPS color digital camera.
Nuclear Magnetic Resonance Spectroscopy (NMR)

1H-NMR data are acquired on Bruker 400 MHz spectrometer at ambient temperature and the chemical shifts reported in ppm.
pKa Values The pKa values are calculated using ACD/pKa (Classic, GALAS), version 2019.2.1, Advanced Chemistry Development, Inc., Toronto, ON, Canada, www.acdlabs.com.

Example 2

CSP-1103

Figure 1A:
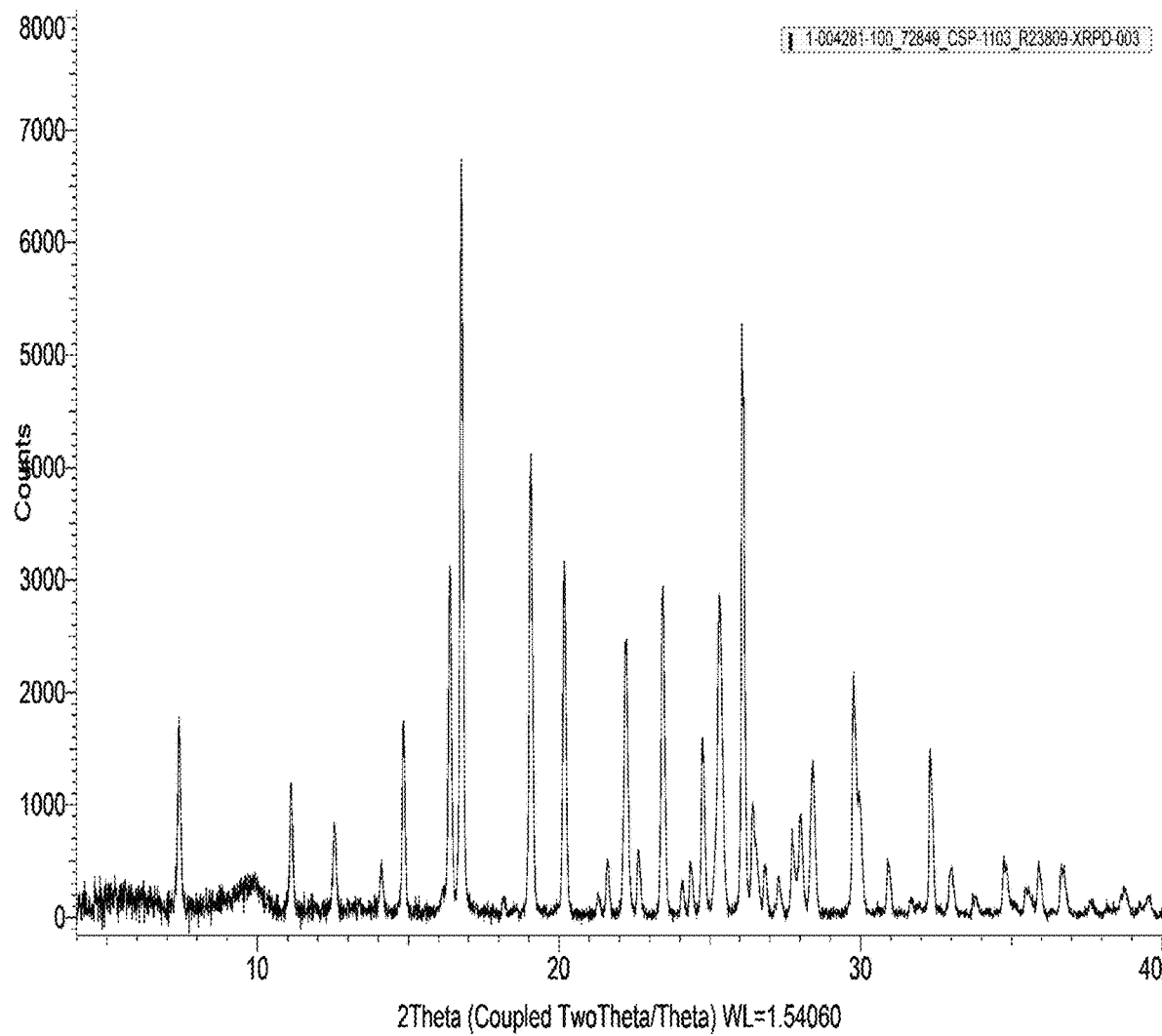
FIG. 1A is the XRPD for CSP-1103.
Figure 1B:
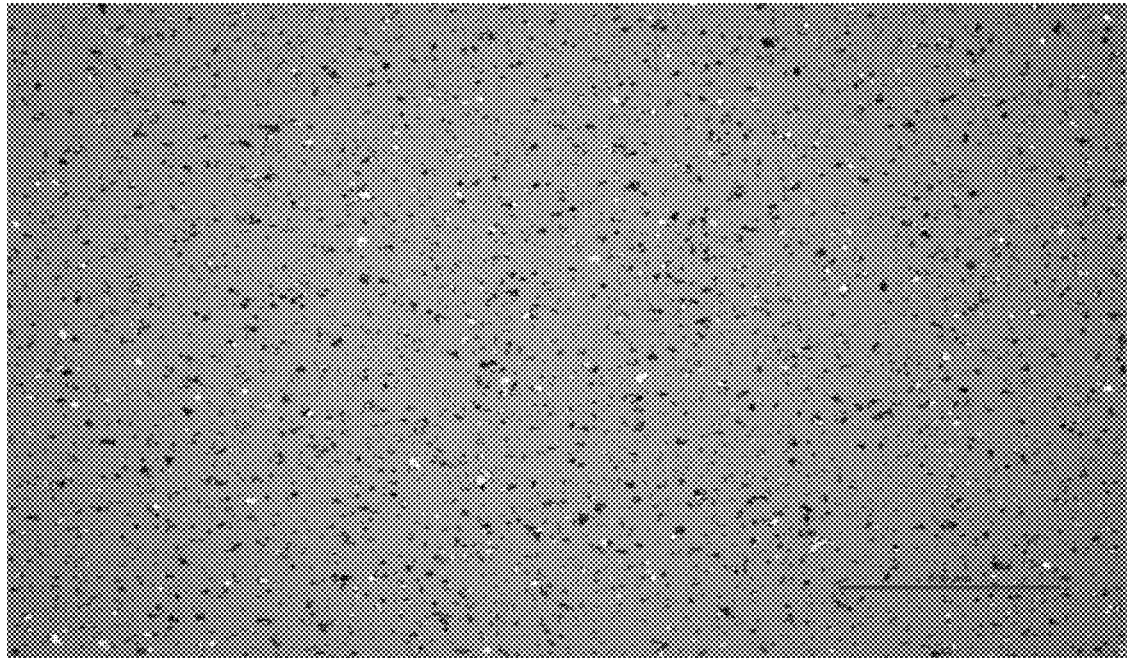
FIGS. 1B-1E depict photomicrographs at various magnifications of CSP-1103.
Figure 1C:
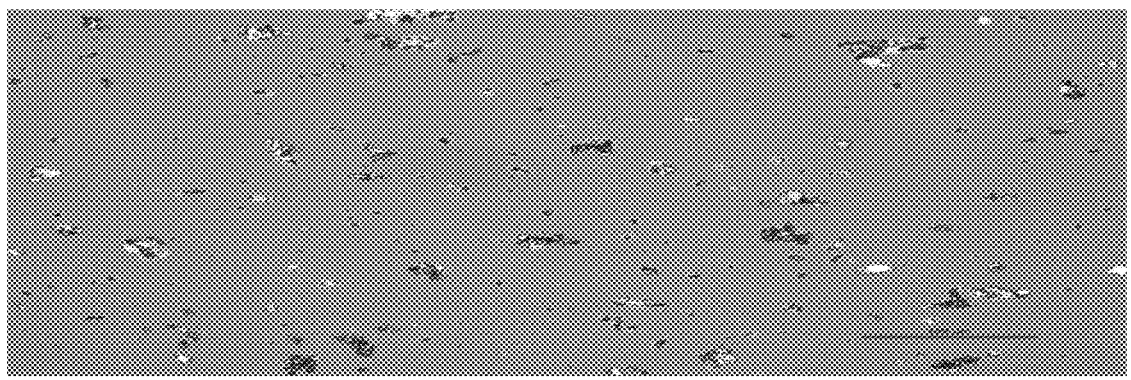
Figure 1D:
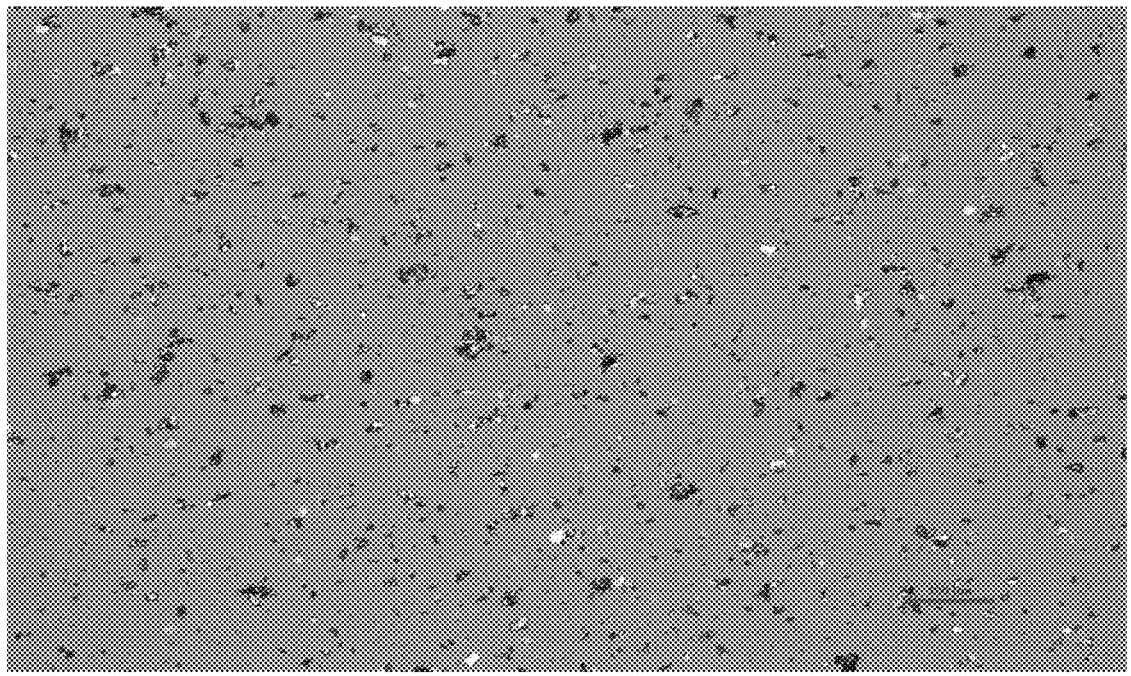
Figure 1E:
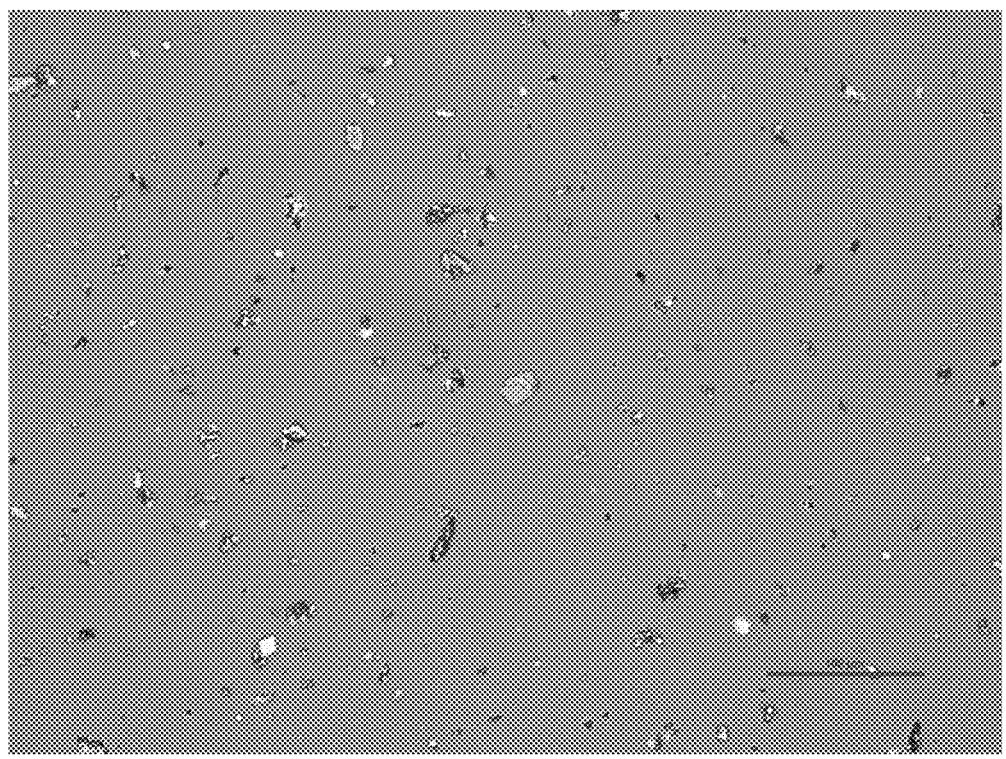

The XRPD for CSP-1103 displayed a typical crystalline pattern and is replicated in FIG. 1A.

The DSC for CSP-1103 displayed a single endothermic event with an onset at 200.2° C. and a peak maximum of 201.0° C. and a ΔH of 123.1 J/g followed by degradation. Degradation appears to start occurring after 200° C. by TGA. Mass loss from ambient temperature to 195.0° C. was 0.6%, and to 208.0° C. was 0.9% (total loss).

DVS adsorption and desorption results for CSP-1103 (5-95% RH, 25° C.) are presented in Table 1.

TABLE 1

| R23809-DVS-003, CSP-1103, lot N1200856 (1-004281-100, 72849) | | | | | | | |
|---|---|---|---|---|---|---|---|
| Cycle 1 of 2 | RH Start (%) | RH Stop (%) | Mass Change (%) | Cycle 2 of 2 | RH Start (%) | RH Stop (%) | Mass Change (%) |
| Adsorption | 5 | 95 | 1.10 | Adsorption | 5 | 95 | 1.13 |
| Desorption | 95 | 5 | −1.11 | Desorption | 95 | 5 | −1.13 |

The average water sorbed or desorbed for this material is 1.1±0.0% between 5-95% RH. This material should be considered slightly hygroscopic at 95% RH (<2% and ≥0.2%, Ph. Eur. 9.0). The XRPD results for the preexposed and post-exposed materials are comparable to each other, e.g., no solid form change.

Photomicrographs were obtained for CSP-1103 by PLM and then calibrated according to the objective magnification.

The particles exhibit birefringence indicating the material is crystalline. The particles at lower magnifications appear as aggregates (loosely held particles) consisting of irregularly-shaped primary particles ranging from <2-25 μm by <2-25 μm; see FIG. 1B-1E.

The calculated pKa value for the carboxylic acid moiety of CSP-1103 is 4.1±0.4

The 1H-NMR for CSP-1103 in DMSO-d6 displayed three distinct chemical shift regions: (1) the acidic proton at δ12.5 ppm; (2) the aromatic protons between at δ7.2-7.8 ppm; and (3) the cyclopropyl protons with one set of two protons at δ1.2 ppm and another set of two protons between 1.4-1.5 ppm with both integrating to two protons for each set.

Either the acidic proton, the aromatic proton at δ7.8 (singlet), the aromatic proton at δ7.7 (doublet), or either set of the cyclopropyl protons can be used to integrate CSP to determine the ratio between it and a coformer verifying the stoichiometric ratio in the co-crystal.

Example 3

Cocrystallization screens using solvent-assisted grinding (SAG) and slurry/solubilization (S/S) techniques were investigated with CSP-1103 and different coformers.

Coformers which are considered GRAS (generally recognized as safe) and/or identified as approved inactive ingredients for drug products were investigated. The relevant information on the coformers is provided in Table 2.

determine if the coformers had remained in solution. Qualitative solubility results for coformers in various solvents is presented in Table 3 (A)-(F):

TABLE 3(A)

| Solvent | Molecule | 0.2M | 0.1M | 0.05M | >65 hours |
|---------|----------|------|------|-------|-----------|
| acetone | ASC | YX | YX | YX ✓ | X |
|         | BZA | ✓ | NA | NA | ✓ |
|         | CFA | YX | Y ✓ | NA | ✓ |
|         | CAF | YX | YX | YX ✓ | ✓ |
|         | CA  | Y ✓ | NA | NA | ✓ |
|         | GMA | YX | YX | YX | X |
|         | NCT | Y ✓ | NA | NA | ✓ |
|         | PA  | YX | YX | YX | X |
|         | SAC | ✓ | NA | NA | ✓ |
|         | VN  | ✓ | NA | NA | ✓ |

TABLE 3(B)

| Solvent | Molecule | 0.2M | 0.1M | 0.05M | >65 hours |
|---------|----------|------|------|-------|-----------|
| methanol (BP 65° C.) | ASC | Y ✓ | NA | NA | ✓ |
|         | BZA | ✓ | NA | NA | ✓ |
|         | CFA | ✓ | NA | NA | ✓ |
|         | CAF | YX | YX ✓ | YX ✓ | X |
|         | CA  | ✓ | NA | NA | ✓ |
|         | GMA | YX | YX | YX | X |

TABLE 2

| Molecule | Abbreviation | CAS# | MW (g/mol) | GRAS[1] | pKa$_1$ | IID[2] | Classification | Other Classification |
|----------|--------------|------|------------|---------|---------|--------|----------------|----------------------|
| L-ascorbic acid | ASC | 50-81-7 | 176.12 | Y(1) | 4.2 | Y | acid | |
| benzoic acid | BZA | 65-85-0 | 122.12 | Y(1) | 4.2 | Y | acid/aromatic | |
| caffeic acid | CFA | 331-39-5 | 180.16 | N | 3.6 | Y | hydroxycinnamic acid/ phenylpropanoid | |
| caffeine | CAF | 58-08-2 | 194.19 | Y(3, 4) | NA | Y | xanthine alkaloid | |
| citric acid | CA | 77-92-9 | 192.13 | Y(1) | 2.9 | Y | acid/alcohol | |
| glutamic acid | GMA | 617-65-2 | 147.13 | Y(2) | 2.2 | Y | α-amino acid | |
| nicotinamide | NCT | 98-92-0 | 122.13 | Y(1) | 3.4 | N | pyridinyl/amide | nutraceutical/ supplement |
| phenylalanine | PA | 63-91-2 | 165.169 | N | 1.8 | Y | α-amino acid | nutraceutical/ supplement |
| saccharin | SAC | 81-07-2 | 183.18 | N | 1.7 | Y | amide | |
| vanillin | VN | 121-33-5 | 152.15 | N | 7.4 | Y | phenolic aldehyde | |

[1]Numbers in parentheses are the conclusions from the Select Committee on Generally Recognized as Safe Substances (SCOGS US FDA) and can be found at https://www.fda.gov/food/generally-recognized-safe-gras/gras-substances-scogs-database.
[2]Inactive Ingredient Search for Approved Drug Products can be found at https://www.accessdata.fda.gov/scripts/cder/iig/index.cfm The XRPD for the coformers all displayed typical crystalline patterns and was used as reference points during the cocrystallization screen. If further characterizations were needed for a coformer, they were done on an as-needed basis.

Coformer solubility assessment was then performed. The following solvents were selected under these solvent classifications, which represent typical manufacturing solvents and have good solvent-solvent miscibility:

1. Aprotic Polar: acetone, ethyl acetate, acetonitrile;
2. Hydrogen Bond Donor: ethanol, methanol; and
3. Electron Pair Donor: MTBE instead of diethyl ether.

Approximately 0.1 mmol of the coformer was weighed out into a 1-dram vial, enough solvent was added to achieve a 0.2 M concentration, and if required, gentle heating was applied at 45° C. for about 1 minute. If the coformer did not dissolve, additional solvent was added to achieve either a 0.1 M or a 0.05 M concentration, and if required, gentle heating was applied. After 65 hours, observations were made to TABLE 3(B)-continued

| Solvent | Molecule | 0.2M | 0.1M | 0.05M | >65 hours |
|---------|----------|------|------|-------|-----------|
|         | NCT | ✓ | NA | NA | ✓ |
|         | PA  | YX | YX | YX | X |
| ethanol (BP 79° C.) | ASC | YX | YX | YX ✓ | ✓ |
|         | BZA | ✓ | NA | NA | ✓ |
|         | CFA | Y ✓ | NA | NA | ✓ |
|         | CAF | YX | YX | YX | X |
|         | CA  | Y ✓ | NA | NA | ✓ |
|         | GMA | YX | YX | YX | X |
|         | NCT | Y ✓ | NA | NA | ✓ |
|         | PA  | YX | YX | YX | X |
|         | SAC | YX | Y ✓ | NA | ✓ |
|         | VN  | ✓ | NA | NA | ✓ |
|         | SAC | ✓ | NA | NA | ✓ |
|         | VN  | ✓ | NA | NA | ✓ |

TABLE 3(C)

| Solvent | Molecule | 0.2M | 0.1M | 0.05M | >65 hours |
|---|---|---|---|---|---|
| ethanol (BP 79° C.) | ASC | YX | YX | YX✓ | ✓ |
|  | BZA | ✓ | NA | NA | ✓ |
|  | CFA | Y✓ | NA | NA | ✓ |
|  | CAF | YX | YX | YX | X |
|  | CA | Y✓ | NA | NA | ✓ |
|  | GMA | YX | YX | YX | X |
|  | NCT | Y✓ | NA | NA | ✓ |
|  | PA | YX | YX | YX | X |
|  | SAC | YX | Y✓ | NA | ✓ |
|  | VN | ✓ | NA | NA | ✓ |

TABLE 3(D)

| Solvent | Molecule | 0.2M | 0.1M | 0.05M | >65 hours |
|---|---|---|---|---|---|
| acetonitrile (BP 82° C.) | ASC | YX | YX | YX | X |
|  | BZA | ✓ | NA | NA | ✓ |
|  | CFA | YX | YX | YX | X |
|  | CAF | YX | YX✓ | Y✓ | ✓ |
|  | CA | YX | YX✓ | YX✓ | ✓ |
|  | GMA | YX | YX | YX | X |
|  | NCT | YX | Y✓ | NA | ✓ |
|  | PA | YX | YX | YX | X |
|  | SAC | Y✓ | NA | NA | ✓ |
|  | VN | ✓ | NA | NA | ✓ |

TABLE 3(E)

| Solvent | Molecule | 0.2M | 0.1M | 0.05M | >65 hours |
|---|---|---|---|---|---|
| ethyl acetate (BP 77° C.) | ASC | YX | YX | YX | X |
|  | BZA | ✓ | NA | NA | ✓ |
|  | CFA | YX | YX | YX | X |
|  | CAF | YX | YX | YX✓ | X |
|  | CA | YX | YX | YX✓ | ✓ |
|  | GMA | YX | YX | YX | X |
|  | NCT | YX | YX | Y✓ | ✓ |
|  | PA | YX | YX | YX | X |
|  | SAC | Y✓ | NA | NA | ✓ |
|  | VN | ✓ | NA | NA | ✓ |

TABLE 3(F)

| Solvent | Molecule | 0.2M | 0.1M | 0.05M | > 65 hours |
|---|---|---|---|---|---|
| MTBE (BP 85° C.) | ASC | YX | YX | YX | X |
|  | BZA | ✓ | NA | NA | ✓ |
|  | CFA | YX | YX | Y | X |
|  | CAF | YX | YX | YX✓ | X |
|  | CA | YX | YX | YX✓ | ✓ |
|  | GMA | YX | YX | YX | X |
|  | NCT | YX | YX | YX | X |
|  | PA | YX | YX | YX | X |
|  | SAC | YX | YX✓ | Y✓ | ✓ |
|  | VN | ✓ | NA | NA | ✓ |

Legend for Tables 3 (A)-3 (F)

✓ no heat added; dissolved
Y✓ heat added; dissolved
YX✓ heat added; nearly dissolved The solubility assessment of CSP-1103 was then performed. Approximately 0.05 mmol of CSP-1103 was weighed out into a 1-dram vial, enough solvent was added to achieve a 0.2 M concentration, and if required, gentle heating was applied at 45° C. for 1 minute. If the API did not dissolve, additional solvent was added to achieve either a 0.1 M or a 0.05 M concentration, and if required, gentle heating was applied. After 12 hours, observations were made to determine if the API had remained in solution. Qualitative solubility results for CSP-1103 in various solvents is presented in Table 4.

TABLE 4

| Solvents | 0.2M | 0.1M | 0.05M | >12 hours |
|---|---|---|---|---|
| acetone | YX | YX | ✓ | ✓ |
| MTBE | YX | Y✓ | NA | ✓ |
| ethanol | YX | YX✓ | Y✓ | ✓ |
| ethyl acetate | YX | Y✓ | NA | ✓ |
| methanol | YX | YX | Y✓ | X * |
| acetonitrile | YX | YX | YX | X |

Legend

✓ no heat added; dissolved
YX heat added; not dissolved
Y✓ heat added; dissolved
YX✓ heat added; nearly dissolved Coformer and CSP-1103 aqueous solubility assessment was then performed. In a 1-dram vial, enough solvent was added to achieve a 0.05 M aqueous concentration along with some gentle heating at 45° C. for 1 minute to determine if the material would completely dissolve. After 24 hours, observations were made to determine if the material had remained in solution. Qualitative aqueous solubility results for the coformers and CSP-1103 in various solvents is presented in Table 5.

TABLE 5

| Molecule | 0.05M | >24 hours |
|---|---|---|
| ASC | ✓ | ✓ |
| BZA | YX✓ | X |
| CFA | YX | X |
| CAF | Y✓ | ✓ |
| CA | ✓ | ✓ |
| GMA | YX✓ | ✓ |
| NCT | ✓ | ✓ |
| PA | ✓ | ✓ |
| SAC | YX | X |
| VN | Y✓ | ✓ |
| CSP-1103 | YX | X |

Legend

✓ no heat added; dissolved
YX heat added; not dissolved
Y✓ heat added; dissolved
YX✓ heat added; nearly dissolved Solvent-assisted Grinding and Slurry Cocrystallization Investigations were then conducted. Consolidating the solubility results identified the appropriate coformers and solvents to be investigated for the potential co-crystal formation between a coformer and CSP-1103 by both solvent-assisted grinding (SAG) and slurry/solubilization (S/S) techniques. All the organic solvents are miscible with each other. Water is not miscible with ethyl acetate and MTBE. Consolidated solubility results for coformers and CSP-1103 in various solvents is presented in Table 6.

TABLE 6

| | Solvents | | | | | | |
|---|---|---|---|---|---|---|---|
| | Aprotic Polar | | | | | | Electron Pair |
| | | ethyl | | H-Bond Acceptor | | | Donor |
| Materials | acetone | acetate | acetonitrile | ethanol | methanol | water | MTBE |
| L-ascorbic acid | ✗ | ✗ | ✗ | ✓ | ✓ | ✓ | ✗ |
| benzoic acid | ✓ | ✓ | ✓ | ✓ | ✓ | ✗ | ✓ |
| caffeic acid | ✓ | ✗ | ✗ | ✓ | ✓ | ✗ | ✗ |
| caffeine | ✓ | ✓ | ✓ | ✗ | ✓ | ✓ | ✗ |
| citric acid | ✓ | ✓ | ✓ | ✓ | ✓ | ✓ | ✓ |
| glumatic acid | ✗ | ✗ | ✗ | ✗ | ✗ | ✓ | ✗ |
| nicotinamide | ✓ | ✓ | ✓ | ✓ | ✓ | ✓ | ✗ |
| phenylalanine | ✗ | ✗ | ✗ | ✗ | ✗ | ✓ | ✗ |
| saccharin | ✓ | ✓ | ✓ | ✓ | ✓ | ✗ | ✓ |
| vanillin | ✓ | ✓ | ✓ | ✓ | ✓ | ✓ | ✓ |
| CSP-1103 | ✓ | ✓ | ✗ | ✓ | ✓ | ✗ | ✓ |

Between 0.08 to 0.11 mmol of CSP-1103 was weighed out into a 1-dram vial. Next, approximately 0.09 to 0.13 mmol of a coformer was weighed out and transferred to the vial. In all cases, the coformer would be either equal or greater than the mmol concentration of CSP-1103, but not more than 0.2 mmol. Grinding media was then added to the vial, 50 µL of the solvent, and was ground in a mixer.

After mixing, a portion of the material was removed and placed onto an XRPD plate for analysis. If warranted, the dried material from the XRPD plate was used to run TGA and DSC; otherwise, the dried material was added back into the vial for the slurry/solubilization cocrystallization experiments. Two (2) mL of the same solvent used in the SAG experiments were added into the vial and heated between 45-75° C. for up to 15 minutes to dissolve the components. In all cases, the solvent was allowed to evaporate to dryness before the XRPD analysis. Consolidated XRPD results for the SAG and the S/S cocrystallization investigations are presented in Table 7.

TABLE 7

| R23809-006-### SAG | Solvent | CSP (mmol) | Coformer | mmol | Designation | XRPD via SAG | R23809-006-### S/S | XRPD via S/S |
|---|---|---|---|---|---|---|---|---|
| 001 | acetone | 0.09 | BZA | 0.11 | CSPBZA | ✗ | 001SE | ✗ |
| 002 | | 0.10 | CFA | 0.12 | CSPCFA | ✗ | 002SE | ✗ |
| 003 | | 0.10 | CAF | 0.11 | CSPCAF | ✗ | 003SE | ✗ |
| 004 | | 0.10 | CA | 0.11 | CSPCA | ✗ | 004SE | ✓ |
| 005 | | 0.09 | NCT | 0.11 | CSPNCT | ✗ | 005SE | ✓ |
| 006 | | 0.09 | SAC | 0.11 | CSPAC | ✗ | 006SE | ✗ |
| 007 | | 0.11 | VN | 0.13 | CSPVN | ✗ | 007SE | ✗ |
| 008 | methanol | 0.08 | ASC | 0.10 | CSPASC | ✗ | 008SE | ✗ |
| 009 | | 0.09 | BZA | 0.10 | CSPBZA | ✗ | 009SE | ✗ |
| 010 | | 0.10 | CFA | 0.12 | CSPCFA | ✗ | 010SE | ✗ |
| 011 | | 0.08 | CA | 0.10 | CSPCA | ✓ | 011SE | ✓ |
| 012 | | 0.10 | NCT | 0.12 | CSPNCT | ✗ | 012SE | ✗ |
| 013 | | 0.09 | SAC | 0.10 | CSPSAC | ✗ | 013SE | ✗ |
| 014 | | 0.09 | VN | 0.10 | CSPVN | ✗ | 014SE | ✗ |
| 015 | 75% | 0.11 | BZA | 0.12 | CSPBZA | ✗ | 015SE | ✗ |
| 016 | MTBE | 0.10 | CA | 0.12 | CSPCA | ✗ | 016SE | ✓ |
| 017 | 25% | 0.08 | SAC | 0.10 | CSPSAC | ✗ | 017SE | ✗ |
| 018 | MeOH | 0.09 | VN | 0.10 | CSPVN | ✗ | 018SE | ✗ |
| 037 | 75% | 0.08 | ASC | 0.09 | CSPASC | ✗ | 037SE | ✗ |
| 038 | water | 0.09 | CAF | 0.10 | CSPCAF | ✗ | 038SE | ✗ |
| 039 | 25% | 0.10 | CA | 0.11 | CSPCA | ✓ | 039SE | ✗ |
| 040 | MeOH | 0.10 | GMA | 0.11 | CSPGMA | ✗ | 040SE | ✗ |
| 041 | | 0.10 | NCT | 0.12 | CSPNCT | ✗ | 041SE | ✗ |
| 042 | | 0.08 | PA | 0.09 | CSPPA | ✗ | 042SE | ✗ |
| 043 | | 0.09 | VN | 0.10 | CSPVN | ✗ | 043SE | ✗ |
| 019 | Ethyl | 0.08 | BZA | 0.09 | CSPBZA | ✗ | 019SE | ✗ |
| 020 | acetate | 0.09 | CA | 0.11 | CSPCA | ✗ | 020SE | ✗ |
| 021 | | 0.09 | NCT | 0.11 | CSPNCT | ✗ | 021SE | ✓ |
| 022 | | 0.08 | SAC | 0.09 | CSPSAC | ✗ | 022SE | ✓ |
| 023 | | 0.08 | VN | 0.10 | CSPVA | ✓ | 023SE | ✓ |
| 024 | ethanol | 0.08 | ASC | 0.09 | CSPASC | ✗ | 024SE | ✗ |
| 025 | | 0.08 | BZA | 0.10 | CSPBZA | ✗ | 025SE | ✗ |
| 026 | | 0.08 | CFA | 0.09 | CSPCFA | ✗ | 026SE | ✗ |
| 027 | | 0.11 | CA | 0.13 | CSPCA | ✓ | 027SE | ✓ |
| 028 | | 0.10 | NCT | 0.10 | CSPNCT | ✗ | 028SE | ✓ |
| 029 | | 0.09 | SAC | 0.11 | CSPSAC | ✗ | 029SE | ✓ |
| 030 | | 0.09 | VN | 0.11 | CSPVN | ✗ | 030SE | ✗ |

TABLE 7-continued

| R23809-006-### SAG | Solvent | CSP (mmol) | Coformer | mmol | Designation | XRPD via SAG | R23809-006-### S/S | XRPD via S/S |
|---|---|---|---|---|---|---|---|---|
| 031 | acetonitrile | 0.10 | BZA | 0.12 | CSPBZA | ✗ | 031SE | ✗ |
| 032 | | 0.09 | CAF | 0.10 | CSPCAF | ✗ | 032SE | ✗ |
| 033 | | 0.09 | CA | 0.10 | CSPCA | ✓ | 033SE | ✓ |
| 034 | | 0.10 | NCT | 0.12 | CSPNCT | ✗ | 034SE | ✗ |
| 035 | | 0.10 | SAC | 0.11 | CSPSAC | ✗ | 035SE | ✗ |
| 036 | | 0.09 | VN | 0.09 | CSPVN | ✗ | 036SE | ✗ |

Based on the experimental results from the cocrystallization screens, it was concluded that co-crystals may be potentially produced between CSP-1103 and the following coformers:

1. Citric acid from methanol or acetonitrile,
2. Nicotinamide from ethyl acetate,
3. Saccharin from ethyl acetate, and
4. Vanillin from ethyl acetate.

There is some evidence that co-crystals may exist between CSP-1103 and ascorbic acid produced from ethyl acetate and between CSP-1103 and caffeine produced from acetonitrile.

The qualitative solvent solubility for CSP-1103 and the coformers overlaid with the cocrystallization screens' results are presented in Table 8. Table 8 displays the molar concentrations for the components pending investigation for the potential formation of co-crystals with that combination of components and solvent.

TABLE 8

| Coformers | acetone (BP 56° C.) | ethyl acetate (BP 77° C.) | acetonitrile (BP 82° C.) | MTBE (BP 55° C.) | ethanol (BP 79° C.) | methanol (BP 65° C.) | water (BP 100° C.) |
|---|---|---|---|---|---|---|---|
| L-ascorbic acid | ✗ | ✗ | ✗ | ✗ | 0.05 | 0.2 | ✓ |
| benzoic acid | ✓ | ✓ | ✓ | ✓ | ✓ | ✓ | ✗ |
| caffeic acid | ✓ | ✗ | ✗ | ✗ | ✓ | ✓ | ✗ |
| caffeine | ✓ | ✗ | 0.1 | ✗ | ✗ | ✗ | ✓ |
| citric acid | ✓ | ✓ | 0.1 | 0.05 | 0.2 | 0.2 | ≥0.05 |
| glutamic acid | ✗ | ✗ | ✗ | ✗ | ✗ | ✗ | ✓ |
| nicotinamide | 0.2 | 0.05 | ✓ | ✗ | 0.2 | ✓ | ✓ |
| phenylalanine | ✗ | ✗ | ✗ | ✗ | ✗ | ✗ | ✓ |
| saccharin | ✓ | 0.2 | ✓ | ✓ | 0.1 | ✓ | ✗ |
| vanillin | ✓ | 0.2 | ✓ | ✓ | ✓ | ✓ | ✓ |
| CSP-1103 | 0.05 | 0.1 | ✗ | 0.1 | 0.05 | 0.05 | ✗ |

Based on the qualitative solubility assessment, in most cases, the coformers are more soluble than CSP-1103, and that if the solubilities differ enough, the co-crystal may be incongruently saturating in that solvent system.

Example 4

API to coformer ratios were then investigated. Approximately 0.5 mmol of CSP-1103 was weighed out into a 1-dram vial. Next, depending on the coformer to CSP ratio, the appropriate millimoles of the coformer were weighed out and transferred to the vial. The solvent was then added to the vial and heated with stirring between 45-75° C. for up to 60 minutes. The slurries were then allowed to cool while continuing to stir overnight.

After overnight stirring, at a minimum, a portion of the slurry was removed and placed onto an XRPD plate for analysis. If warranted, the dried material from the XRPD plate was used to run TGA and DSC; otherwise, the dried material was added back into the vial.

Then additional solvent was added to the vial and heated with stirring between 45-75° C. for up to 60 minutes. The slurries were then allowed to cool while continuing to stir overnight. After XRPD analyses, another solvent addition was repeated for all investigations except for VN (initial study).

The results of the investigations are presented in Table 9.

TABLE 9

| Vanillin (VN) | | | | First Solvent Addition | | | Second Solvent Addition | | |
|---|---|---|---|---|---|---|---|---|---|
| R23809-010-### | VN Ratio to CSP | CSP (mmol) | VN (mmol) | R23809-10-### | EtOAc (mL) | XRPD | R23809-010-### | EtOAc (mL) | XRPD |
| 021 | 1 | 0.50 | 0.50 | 021 | 0.50 | > | 21CS | 1.50 | > |
| 022 | 2 | 0.49 | 1.00 | 022 | 0.50 | ≈ | 22C | 1.50 | > |
| 023 | 3 | 0.50 | 1.48 | 023 | 0.50 | < | 23C | 1.50 | > |
| 024 | 4 | 0.54 | 2.14 | 024 | 0.50 | < | 24C | 1.50 | < |
| 025 | 5 | 0.50 | 2.55 | 025 | 0.50 | < | 25C | 1.50 | < |

| Saccharin | | | | First Solvent Addition | | | Second Solvent Addition | | | Third Solvent Addition | | |
|---|---|---|---|---|---|---|---|---|---|---|---|---|
| R23809-10-### | SAC Ratio to CSP | CSP (mmol) | SAC (mmol) | R23809-10-### | EtOAc (mL) | XRPD Results | R23809-10-### | EtOAc (mL) | XRPD Results | R23809-010-### | EtOAc (mL) | XRPD Results |
| 016 | 1 | 0.55 | 0.57 | 016 | 0.75 | > | 16C 2nd heat | 1.75 | ≈ | 16CS | 1.25 | > |
| 017 | 2 | 0.60 | 1.24 | 017 | 0.75 | < | 17C | 1.75 | < | 17CS | 2.50 | > |
| 018 | 3 | 0.57 | 1.72 | 018 | 0.75 | < | 18C | 1.75 | < | 18CS | 2.75 | < |
| 019 | 4 | 0.57 | 2.30 | 019 | 0.75 | < | 19C | 1.75 | < | 19CS | 3.25 | < |
| 020 | 5 | 0.57 | 2.87 | 020 | 0.75 | < | 20C | 1.75 | < | 20CS | 3.75 | < |

| Citric Acid (CA) | | | | First Solvent Addition | | | Second Solvent Addition | | | Third Solvent Addition | | |
|---|---|---|---|---|---|---|---|---|---|---|---|---|
| R23809-011-### | CA Ratio to CSP | CSP (mmol) | CA (mmol) | R23809-011-### | CAN (mL) | XRPD Results | R23809-011-### | CAN (mL) | XRPD Results | R23809-011-### | CAN (mL) | XRPD Results |
| 006 | 1 | 0.50 | 0.50 | 006 | 0.75 | > | 006-1 | 2.00 | > | 006-2 | 2.50 | > |
| 007 | 2 | 0.58 | 1.17 | 007 | 0.75 | ≈ | 007-1 | 2.00 | < | 007-2 | 2.50 | < |
| 008 | 3 | 0.54 | 1.63 | 008 | 0.75 | > | 008-1 | 2.00 | < | 008-2 | 2.50 | < |
| 009 | 4 | 0.52 | 2.09 | 009 | 0.75 | < | 009-1 | 2.00 | < | 009-2 | 2.50 | < |
| 010 | 5 | 0.50 | 2.50 | 010 | 0.7 | < | 010-1 | 2.00 | < | 010-2 | 2.50 | < |

| Nicotinamide (NCT) | | | | First Solvent Addition | | | Second Solvent Addition | | | Third Solvent Addition | | |
|---|---|---|---|---|---|---|---|---|---|---|---|---|
| R23809-011-### | NCT Ratio to CSP | CSP (mmol) | NCT (mmol) | R23809-011-### | EtOAc (mL) | XRPD Results | R23809-011-### | EtOAc (mL) | XRPD Results | R23809-011-### | EtOAc (mL) | XRPD Results |
| 031 | 1 | 0.53 | 0.55 | 031 | 0.75 | > | 031-1 | 1.75 | ≈ | 031-2 | 3 | > |
| 032 | 2 | 0.50 | 1.03 | 032 | 0.75 | ≈ | 032-1 | 1.75 | ≈ | 032-2 | 3 | ≈ |
| 033 | 3 | 0.50 | 1.52 | 033 | 0.75 | < | 033-1 | 1.75 | < | 033-2 | 3 | ≈ |
| 034 | 4 | 0.53 | 2.12 | 034 | 0.75 | < | 034-1 | 1.75 | < | 034-2 | 3 | < |
| 035 | 5 | 0.53 | 2.66 | 035 | 0.75 | < | 035-1 | 1.75 | < | 035-2 | 3 | < |

| Citric Acid (CA) | | | | First Solvent Addition | | | Second Solvent Addition | | | Third Solvent Addition | | |
|---|---|---|---|---|---|---|---|---|---|---|---|---|
| R23809-011-### | CA Ratio to CSP | CSP (mmol) | CA (mmol) | R23809-011-### | MeOH (mL) | XRPD Results | R23809-011-### | MeOH (mL) | XRPD Results | R23809-011-### | MeOH (mL) | XRPD Results |
| 001 | 1 | 0.55 | 0.58 | 001 | 1.50 | > | 001-1 | 2.00 | > | 001-2 | 3.0 | > |
| 002 | 2 | 0.51 | 1.03 | 002 | 1.50 | > | 002-1 | 2.00 | > | 002-1 | 3.0 | > |
| 003 | 3 | 0.55 | 1.65 | 003 | 1.50 | > | 003-1 | 2.00 | > | 003-1 | 3.0 | > |
| 004 | 4 | 0.54 | 2.18 | 004 | 1.50 | > | 004-1 | 2.00 | > | 004-2 | 3.0 | > |
| 005 | 5 | 0.54 | 2.71 | 005 | 1.50 | > | 005-1 | 2.00 | > | 005-2 | 3.0 | > |

The XRPD results indicated the slurry investigations did not produce co-crystals but only mixtures of CSP-1103 and the coformer. A greater than symbol (">") implies that CSP-1103 was qualitatively greater in quantity than the coformer. A less than symbol ("<") implies that CSP-1103 was qualitatively lesser in quantity than the coformer. In some cases, both components appear to be in equal concentrations ("~").

Example 5

Co-Crystal Production Via Saturated Coformer Solutions

Various solvents were saturated with a coformer, and then a known volume was transferred into a 1-dram vial. Approximately 0.01 mmol of CSP-1103 was weighed out into the 1-dram vial containing the saturated solution, heated with gentle agitation between 45-75° C. for up to 60 minutes. The vial was then allowed to stand at ambient temperature for slow evaporation. Crystalline materials were harvested after the solution evaporated sufficiently.

The crystalline material was placed onto an XRPD plate for analysis. If warranted, the crystalline material from the XRPD plate was used to run TGA and DSC, and other physicochemical techniques; otherwise, the material was added back into the vial.

The Experimental details for saturated coformer solutions investigations are presented in Table 10.

TABLE 10

| R23809 Experiment | Coformer (sat.) | Solvent | CSP (mmol) | Solvent Added (mL) | Comments |
|---|---|---|---|---|---|
| 012-004 | CA | MTBE | 0.10 | 1 | CSP and CA mixture |
| 012-005 | CA | MeOH | 0.10 | 4 | XRPD indicates possible co-crystal-investigate further |
| 012-006 | CA | EtOH | 0.10 | 3 | CSP and CA mixture |
| 012-007 | CA | EtOH/H$_2$O | 0.09 | 4 | gelled solution-use EtOAc instead of water |
| 013-001 | CA | EtOH/EtOAc | 0.10 | 1 | CSP and CA mixture |
| 012-001 | NCT | EtOAc | 0.09 | 1 | XRPD indicates possible co-crystal-investigate further |
| 012-008 | NCT | EtOH/H$_2$O | 0.09 | 2 | CSP and NCT mixture |
| 013-002 | NCT | EtOH/EtOAc | 0.10 | 1 | solvent nearly evaporated-XRPD indicates possible co-crystal-investigate further |
| 012-002 | SAC | EtOAc | 0.09 | 1 | CSP and SAC mixture |
| 012-003 | VN | EtOAc | 0.10 | 1 | CSP and VN mixture |
| 012-009 | VN | EtOH/H$_2$O | 0.10 | 2 | CSP and VN mixture |
| 013-003 | VN | EtOH/EtOAc | 0.11 | 1 | mostly VN |

Based on the XRPD results, experiments R23809-012-005 (CA), R23809-012-001 (NCT), and R23809-013-002 (NCT) possibly indicated co-crystal formation, further thermal and NMR characterizations were warranted for these samples. Based on the experimental results, R23809-012-005 was found to be a mixture of the single components of CSP and CA; R23809-012-001 was found to be nearly a pure co-crystal of CSP and NCT-CSPNCT; and R23809-013-002 was found to be a mixture of two components, NCT along with a lesser amount of CSPNCT. The ratio between CSP and NCT for R23809-012-001 is 1.1 to 1.0 and for R23809-013-002 is 1 to 4.

Example 6

Cocrystallization attempts between itanapraced (CSP-1103) and nicotinamide (NCT) were made. Attempts at producing co-crystals from solvents saturated with a coformer led to the harvesting of a co-crystal between CSP-1103 and nicotinamide (CSPNCT).

Figure 2:
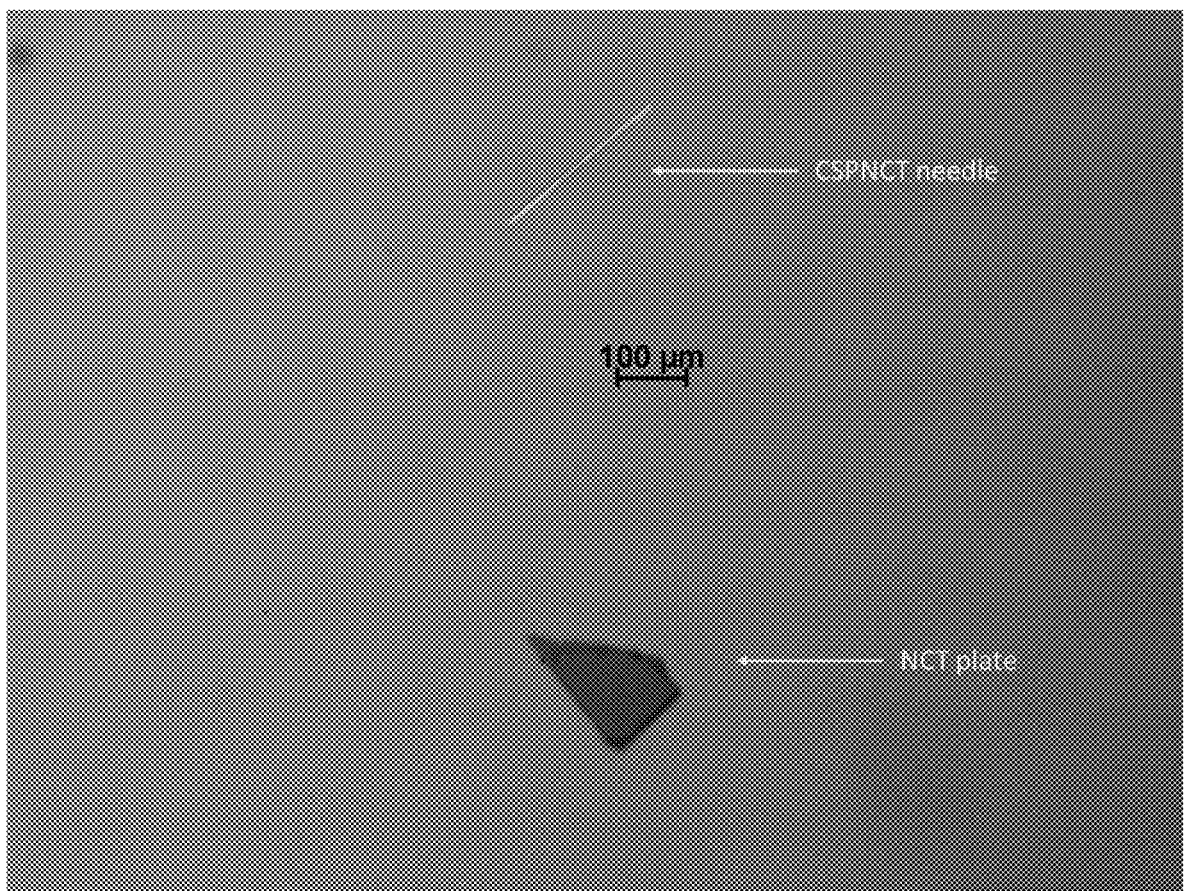
FIG. 2 is a photomicrograph of CSPNCT needle along with NCT.

The crystal habit of NCT is that of colorless plate-like morphonology, and the crystal habit of CSP of colorless needles. The crystal habit of the CSPNCT is that of colorless needles; see FIG. 2.

Preliminary single-crystal X-ray diffraction results indicate that the supramolecular structural interaction is between the NCT pyridinyl moiety and the CSP carboxylic acid moiety.

The unit cell and symmetry of the two components of the co-crystal were characterized by single crystal diffraction to be:

C.SP-1103 (300° K): P2 (1)/c (Monoclinic) with a=23.9851 (4) Å, b=7.36928 (15) Å, c=8.22003 (15) Å, and β=95.0080 (17)°, and NCT (150° K): P2 (1)/c (Monoclinic) with a=3.877 (4) Å, b=15.60 (1) Å, c=9.375 (6) Å, and β=98.45 (7)°.

Figure 3A:
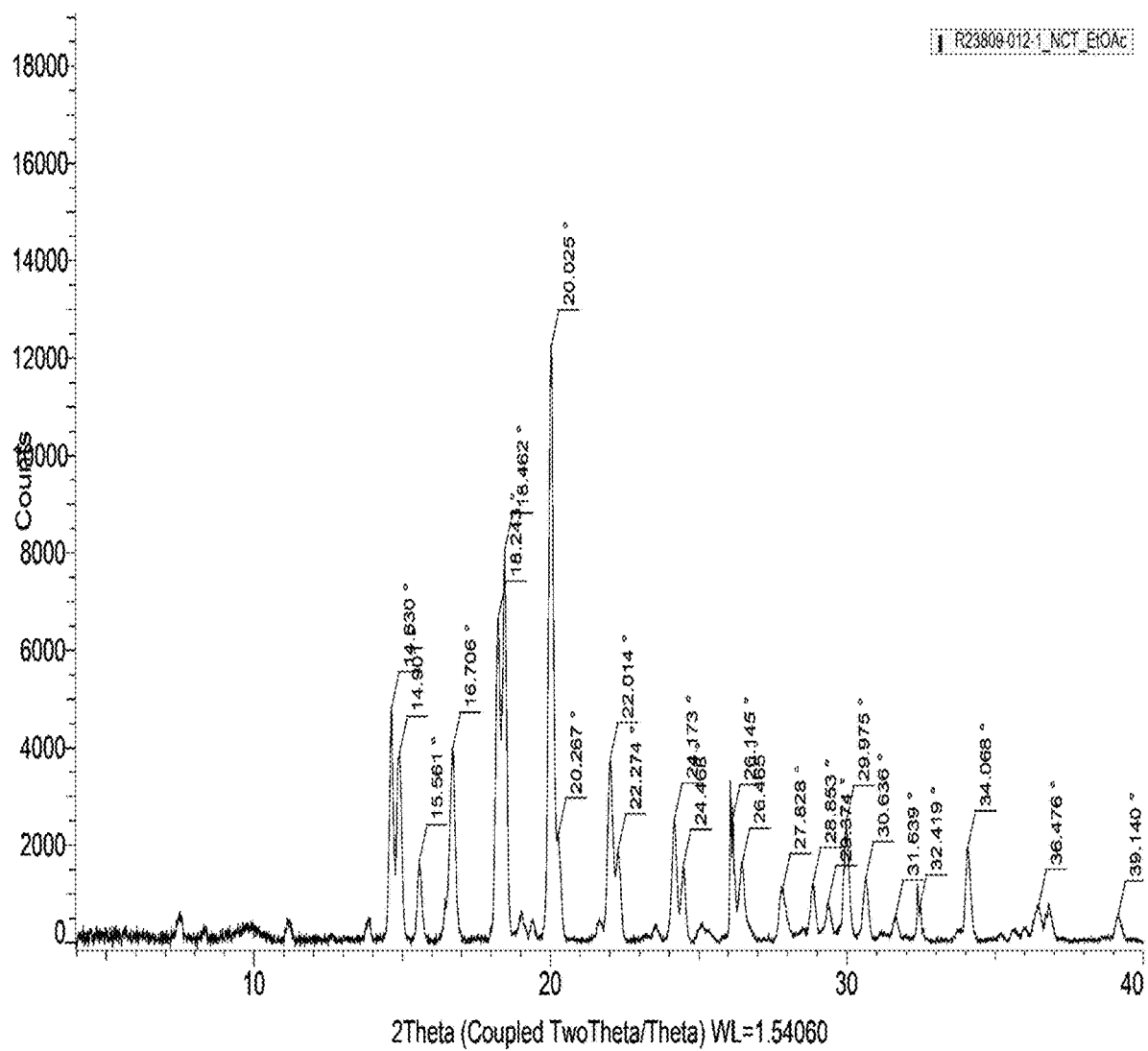
FIG. 3A is XRPD for CSPNCT.

The XRPD for CSPNCT displayed a typical crystalline pattern and has a unique diffraction pattern compared to CSP and NCT. The XRPD for CSPNCT is depicted in FIG. 3A. The peak list, expressed in 2θ produced from a Cu radiation source (λ=1.54 Å after Ni filtering), is as follows:

Cu Kαλ=1.54060

| Peak Position | Angle (° 2θ) | Angle (° 2θ) | Relative Intensity | d Value (Å) |
|---|---|---|---|---|
| 1 | 14.63 | 14.62988 | 39% | 6.05 |
| 2 | 14.90 | 14.90119 | 32% | 5.94 |
| 3 | 15.56 | 15.56149 | 14% | 5.69 |
| 4 | 16.71 | 16.70641 | 33% | 5.30 |
| 5 | 18.24 | 18.24253 | 54% | 4.86 |
| 6 | 18.46 | 18.46165 | 66% | 4.80 |
| 7 | 20.03 | 20.02535 | 100% | 4.43 |
| 8 | 20.27 | 20.26669 | 18% | 4.38 |
| 9 | 22.01 | 22.01394 | 31% | 4.03 |
| 10 | 22.27 | 22.27429 | 15% | 3.99 |
| 11 | 24.17 | 24.1732 | 21% | 3.68 |
| 12 | 24.47 | 24.46769 | 13% | 3.64 |
| 13 | 26.14 | 26.14478 | 20% | 3.41 |
| 14 | 26.47 | 26.4653 | 13% | 3.37 |
| 15 | 27.83 | 27.82752 | 9% | 3.20 |
| 16 | 28.85 | 28.8533 | 10% | 3.09 |
| 17 | 29.97 | 29.97498 | 20% | 2.98 |
| 18 | 30.64 | 30.63574 | 11% | 2.92 |
| 19 | 32.42 | 32.41929 | 5% | 2.76 |
| 20 | 34.07 | 34.06786 | 16% | 2.63 |
| 21 | 39.14 | 39.13952 | 4% | 2.30 |

Figure 3B:
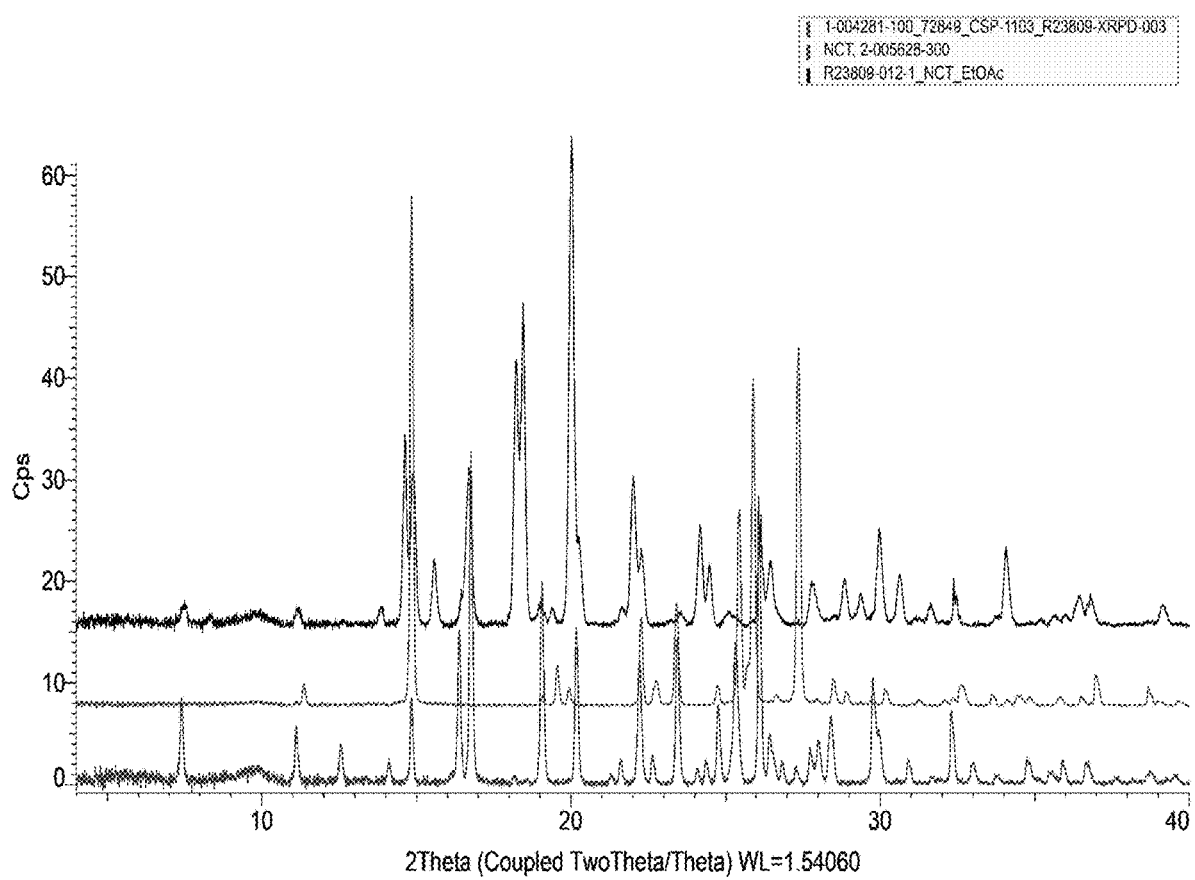
FIG. 3B is XRPD comparison of CSPNCT (top), CSP-1103 (bottom), and NCT (middle).

The comparison between CSPNCT, CSP and NCT is presented in FIG. 3B.

Photomicrographs were obtained for CSPNCT by PLM and then calibrated according to the objective magnification. The photomicrographs are provided in FIGS. 9A-9D. The particles exhibit birefringence indicating the material is crystalline. The particles appear as a conglomerate of needle-like fibers (4-8 μm by >40 μm) and larger crystals greater than 40 μm.

Example 7

A crystal of CSPNCT was characterized by single crystal diffraction analysis.

A suitable single crystal of CSPNCT was isolated and mounted on a glass fiber with paratone oil on an XtaLAB Synergy diffractometer equipped with a micro-focus rotating-anode X-ray tube Rigaku (Cu|Mo) X-ray source) and a Hybrid Pixel Array Detector (HyPix) detector. Temperature of the crystal was controlled with an Oxford Cryosystems low-temperature device. Data reduction was performed with the CrysAlisPro software using a multi-scan absorption correction. The structure was solved with the ShelXT1 structure solution program using the Intrinsic Phasing solution method and by using Olex22 as the graphical interface. The model was refined with ShelXL3 using least squares minimization.

Figure 4:
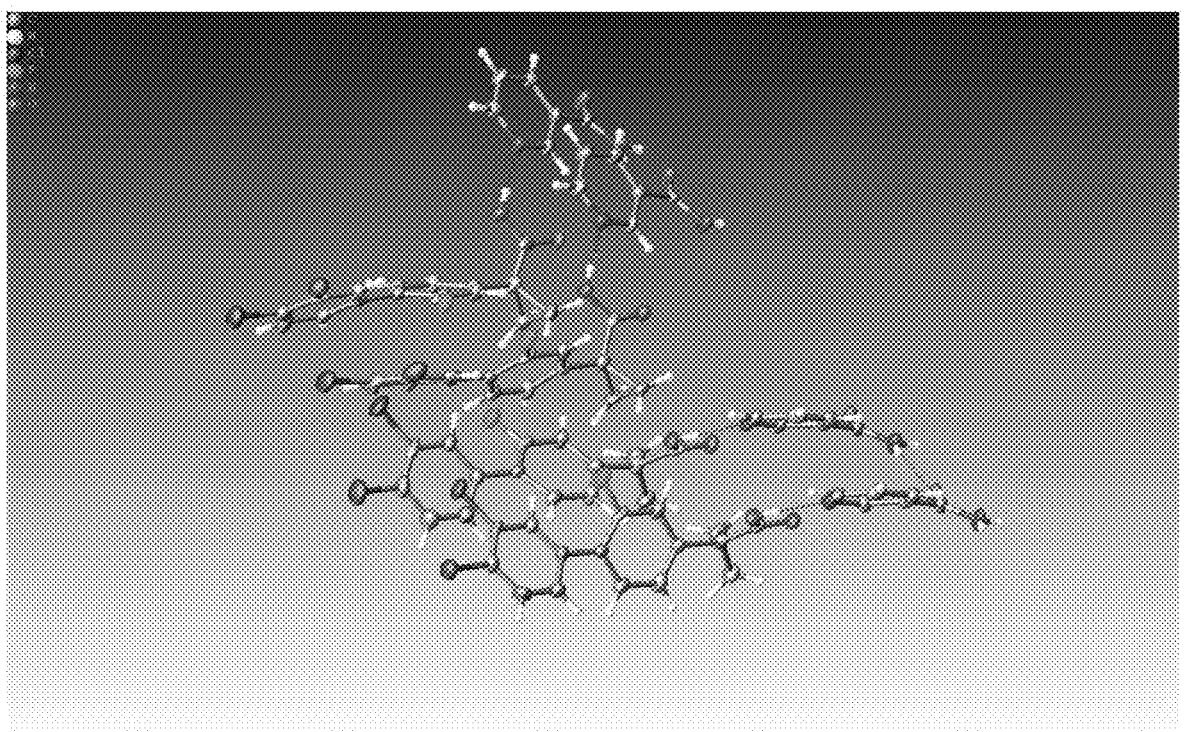
FIG. 4 depicts a unit cell of CSPNCT with of 4 NCT and 4 CSP molecules.

CSPNCT is formed by the cocrystallization of 4 NCT and 4 CSP co-crystals in the unit cell; see FIG. 4. Positional disorder on the orientation of the F-substituted phenyl ring of CSP was found crystallographically where the F-atoms point along two different distinct directions. The formation of a 2-fold supercell was observed for CSPNCT after careful examination of weak intensity reflections. The average picture of the CSPNCT structure is the same with and without the supercell where four (4) molecules of NCT and CSP cocrystallize. Crystallographic refinement of the supercell at 100° K showed that the distribution of the two directions of the F-substituted phenyl rings is approximately 80:20% as opposed to the initial at 250° K, and erroneous, 50:50% observed for the subcell (no-supercell consideration).

The apparent unit cell dimensions of CSPNCT are 5.1288 (2) Å×12.1484 (7) Å×32.2055 (16) Å, 90.618 (4)°, 91.393 (4)°, 90.394 (4)° at 250° K. Careful examination of the reciprocal lattice revealed weak in intensity reflections due the formation of a supercell with a 2-fold superlattice. The summary of crystallographic data for $C_{88}H_{68}Cl_8F_4N_8O_{12}$ (CSPNCT) (M=1789.10 g/mol)* is: triclinic, space group P-1 (no. 2), a=10.2281 (4) Å, b=13.0200 (7) Å, c=32.0677 (18) Å, α=89.774 (4)°, β=88.722 (4)°, γ=67.267 (4)°, V=3937.7 (4) Å$^3$, Z=2, T=100.00 (10) ° K, μ(Cu Kα)=3.296 mm-1, $D_{calc}$=1.509 g/mm$^3$, 17101 reflections measured (5.514°≤2Θ≤103.858°), 7845 unique ($R_{int}$=0.0553, $R_{sigma}$=0.1061) which were used in all calculations. The final $R_1$ was 0.0714 (I >2σ(I)) and $wR_2$ was 0.1842 (I>2σ (I)). *: Bulk properties are not significantly affected by this supercell and the apparent MW (447.02 g/mol) can describe CSPNCT for practical purposes.

Detailed crystallographic information of the refinement and structure of CSPNCT can be found in the attached tables. These tables have been created with Olex2, compiled on 2020.11.12 svn.r5f609507 for OlexSys.

TABLE A1

Crystal data and structure refinement for CSPNCT-supercell.

| | |
|---|---|
| Identification code | CSPNCT-supercell |
| Empirical formula | $C_{88}H_{68}Cl_8F_4N_8O_{12}$ |
| Formula weight | 1789.10 |
| Temperature/° K | 100.00(10) |
| Crystal system | triclinic |
| Space group | P-1 |
| a/Å, b/Å, c/Å | 10.2281(4), 13.0200(7), 32.0677(18) |
| α/°, β/°, γ/° | 89.774(4), 88.722(4), 67.267(4) |
| Volume/Å$^3$ | 3937.7(4) |
| Z | 2 |
| $ρ_{calc}$/mg mm$^{-3}$ | 1.509 |
| μ/mm$^{-1}$ | 3.296 |
| F(000) | 1840 |
| Crystal size/mm$^3$ | 0.21 × 0.05 × 0.02 |
| Radiation | Cu Kα (λ = 1.54184) |
| 2Θ range for data collection/° | 5.514 to 103.858° |
| Index ranges | −10 ≤ h ≤ 9, −13 ≤ k ≤ 13, −32 ≤ l ≤ 32 |
| Reflections collected | 17101 |
| Independent reflections | 7845[R($_{int}$) = 0.0553, $R_{sigma}$ = 0.1061] |

TABLE A1-continued

Crystal data and structure refinement for CSPNCT-supercell.

| | |
|---|---|
| Data/restraints/parameters | 7845/100/1038 |
| Goodness-of-fit on $F^2$ | 1.051 |
| Final R indexes [I > 2σ (I)] | $R_1$ = 0.0714, $wR_2$ = 0.1842 |
| Final R indexes [all data] | $R_1$ = 0.1137, $wR_2$ = 0.2123 |
| Largest diff. peak/hole/e Å$^{-3}$ | 0.525/−0.404 |

TABLE A2

Fractional Atomic Coordinates (×10$^4$) and Equivalent Isotropic Displacement Parameters (Å$^2$ × 10$^3$) for CSPNCT-supercell. $U_{eq}$ is defined as ⅓ of the trace of the orthogonalised $U_{IJ}$ tensor.

| Atom | x | y | z | U(eq) |
|---|---|---|---|---|
| Cl1 | 7416 (2) | 11370.7 (17) | 5085.6 (7) | 45.9 (6) |
| Cl2 | 5119 (2) | 12069.2 (16) | 5812.4 (6) | 38.2 (6) |
| O1 | 10397 (5) | 7849 (4) | 8097.0 (15) | 29.5 (13) |
| O2 | 10527 (5) | 6331 (4) | 8460.5 (16) | 31.5 (13) |
| C1 | 7701 (9) | 10589 (6) | 5538 (2) | 32 (2) |
| C2 | 6700 (8) | 10925 (6) | 5865 (3) | 28.2 (14) |
| C3 | 6953 (8) | 10337 (6) | 6232 (2) | 27.4 (19) |
| C4 | 8171 (8) | 9393 (6) | 6287 (2) | 25.0 (19) |
| C5 | 9144 (8) | 9059 (6) | 5947 (2) | 32 (2) |
| C6 | 8908 (9) | 9659 (5) | 5583 (3) | 40 (2) |
| C13 | 9557 (8) | 6605 (6) | 7777 (2) | 30 (2) |
| C14 | 10116 (9) | 5352 (6) | 7702 (3) | 39 (2) |
| C15 | 8656 (9) | 5943 (6) | 7884 (3) | 39 (2) |
| C16 | 10206 (8) | 6897 (7) | 8148 (3) | 27 (2) |
| F1 | 6101 (5) | 9257 (4) | 6875.9 (15) | 39.0 (7) |
| C7 | 8513 (8) | 8759 (6) | 6679 (2) | 24.1 (10) |
| C8 | 9919 (9) | 8108 (7) | 6787 (3) | 28.8 (11) |
| C9 | 10249 (9) | 7420 (7) | 7129 (3) | 28.8 (11) |
| C10 | 9184 (11) | 7362 (8) | 7401 (3) | 25.1 (11) |
| C11 | 7790 (9) | 8022 (7) | 7309 (3) | 27.7 (12) |
| C12 | 7518 (8) | 8650 (6) | 6960 (3) | 25.2 (12) |
| F1' | 6660 (30) | 9930 (20) | 7096 (11) | 39.0 (7) |
| C7' | 8330 (40) | 8590 (20) | 6636 (8) | 24.1 (10) |
| C8' | 9430 (50) | 7520 (20) | 6649 (10) | 28.8 (11) |
| C9' | 9900 (50) | 6860 (30) | 6999 (10) | 28.8 (11) |
| C10' | 9240 (70) | 7280 (40) | 7384 (10) | 25.1 (11) |
| C11' | 8150 (50) | 8320 (30) | 7389 (10) | 27.7 (12) |
| C12' | 7800 (40) | 8950 (30) | 7038 (8) | 25.2 (12) |
| Cl3 | 2402 (2) | 11538.3 (18) | 5202.1 (7) | 50.5 (7) |
| Cl4 | −92 (2) | 11848.7 (17) | 5858.1 (7) | 46.5 (6) |
| O3 | 5450 (5) | 7768 (4) | 8100.8 (15) | 28.3 (13) |
| O4 | 5625 (5) | 6308 (4) | 8490.3 (16) | 29.6 (13) |
| C17 | 2638 (9) | 10687 (6) | 5631 (3) | 33 (2) |
| C18 | 1583 (8) | 10786 (6) | 5918 (3) | 28.2 (14) |
| C19 | 1777 (8) | 10112 (6) | 6260 (2) | 29 (2) |
| C20 | 3126 (8) | 9285 (6) | 6332 (2) | 25.4 (19) |
| C21 | 4217 (9) | 9180 (7) | 6046 (2) | 34 (2) |
| C22 | 3970 (10) | 9856 (7) | 5698 (3) | 42 (2) |
| C29 | 4636 (8) | 6455 (6) | 7814 (2) | 31 (2) |
| C30 | 5205 (8) | 5201 (6) | 7761 (3) | 34 (2) |
| C31 | 3773 (8) | 5793 (6) | 7949 (2) | 32 (2) |
| C32 | 5281 (8) | 6830 (6) | 8168 (3) | 27.1 (19) |
| F2 | 1624 (5) | 9839 (4) | 7129.6 (15) | 39.0 (7) |
| C23 | 3453 (8) | 8531 (8) | 6707 (3) | 24.1 (10) |
| C24 | 4561 (9) | 7505 (7) | 6708 (3) | 28.8 (11) |
| C25 | 4940 (8) | 6820 (7) | 7048 (3) | 28.8 (11) |
| C26 | 4215 (9) | 7170 (7) | 7430 (3) | 25.1 (11) |
| C27 | 3079 (9) | 8172 (7) | 7438 (3) | 27.7 (12) |
| C28 | 2730 (8) | 8824 (6) | 7088 (3) | 25.2 (12) |
| F2' | 1090 (30) | 9100 (30) | 6878 (11) | 39.0 (7) |
| C23' | 3500 (30) | 8600 (40) | 6721 (10) | 24.1 (10) |
| C24' | 4880 (30) | 8030 (40) | 6830 (13) | 28.8 (11) |
| C25' | 5250 (40) | 7460 (40) | 7200 (12) | 28.8 (11) |
| C26' | 4210 (40) | 7330 (50) | 7467 (15) | 25.1 (11) |
| C27' | 2820 (40) | 7900 (40) | 7354 (13) | 27.7 (12) |
| C28' | 2460 (40) | 8560 (40) | 7006 (11) | 25.2 (12) |
| Cl5 | 2207 (2) | 2938.1 (17) | 4134.5 (7) | 48.2 (6) |
| Cl6 | 3732 (2) | 3573.3 (18) | 4872.7 (7) | 52.6 (7) |
| O5 | 3836 (5) | 7168 (4) | 1909.7 (16) | 30.5 (13) |
| O6 | 2533 (5) | 8609 (4) | 1513.5 (16) | 29.6 (13) |

TABLE A2-continued

Fractional Atomic Coordinates (×10⁴) and Equivalent Isotropic Displacement Parameters (Å² × 10³) for CSPNCT-supercell. $U_{eq}$ is defined as ⅓ of the trace of the orthogonalised $U_{IJ}$ tensor.

| Atom | x | y | z | U(eq) |
|---|---|---|---|---|
| C33 | 3316 (9) | 4372 (7) | 4430 (3) | 38 (2) |
| C34 | 2655 (8) | 4098 (6) | 4101 (3) | 35 (2) |
| C35 | 2368 (8) | 4706 (6) | 3735 (2) | 30 (2) |
| C36 | 2685 (8) | 5653 (6) | 3694 (2) | 26.7 (19) |
| C37 | 3291 (8) | 5952 (7) | 4034 (2) | 34 (2) |
| C38 | 3603 (8) | 5310 (6) | 4394 (3) | 39 (2) |
| C45 | 1682 (8) | 8436 (6) | 2205 (2) | 28 (2) |
| C46 | 184 (8) | 9111 (6) | 2074 (3) | 35 (2) |
| C47 | 1026 (8) | 9683 (6) | 2265 (3) | 35 (2) |
| C48 | 2705 (8) | 8083 (6) | 1840 (3) | 29 (2) |
| F3 | 465 (5) | 5935 (4) | 3121.8 (15) | 39.0 (7) |
| C39 | 2441 (11) | 6317 (7) | 3306 (2) | 24.1 (10) |
| C40 | 3309 (9) | 6903 (7) | 3194 (3) | 28.8 (11) |
| C41 | 3058 (9) | 7573 (7) | 2848 (3) | 28.8 (11) |
| C42 | 1937 (15) | 7693 (9) | 2582 (3) | 25.1 (11) |
| C43 | 1087 (9) | 7096 (7) | 2679 (3) | 27.7 (12) |
| C44 | 1365 (8) | 6455 (6) | 3031 (3) | 25.2 (12) |
| F3' | 1770 (40) | 5150 (20) | 2915 (11) | 39.0 (7) |
| C39' | 2400 (60) | 6390 (30) | 3323 (9) | 24.1 (10) |
| C40' | 2580 (70) | 7420 (30) | 3312 (11) | 28.8 (11) |
| C41' | 2360 (60) | 8070 (30) | 2960 (10) | 28.8 (11) |
| C42' | 1920 (100) | 7740 (50) | 2592 (12) | 25.1 (11) |
| C43' | 1700 (70) | 6750 (30) | 2596 (11) | 27.7 (12) |
| C44' | 1990 (50) | 6110 (30) | 2948 (9) | 25.2 (12) |
| Cl7 | 2995 (2) | 6869.3 (16) | 5806.9 (6) | 39.6 (6) |
| Cl8 | 926 (2) | 6487.0 (17) | 5162.0 (6) | 40.9 (6) |
| O7 | 1299 (5) | 2785 (4) | 8073.2 (15) | 28.7 (13) |
| O8 | 2569 (5) | 1363 (4) | 8476.6 (16) | 30.2 (13) |
| C49 | 1497 (8) | 5633 (6) | 5597 (2) | 28.5 (19) |
| C50 | 2394 (8) | 5790 (6) | 5877 (2) | 28 (2) |
| C51 | 2805 (8) | 5123 (6) | 6226 (2) | 28 (2) |
| C52 | 2331 (8) | 4278 (6) | 6302 (2) | 25.4 (19) |
| C53 | 1418 (8) | 4132 (6) | 6009 (2) | 30 (2) |
| C54 | 1015 (9) | 4799 (7) | 5665 (2) | 37 (2) |
| C61 | 3463 (8) | 1496 (6) | 7795 (2) | 28 (2) |
| C62 | 4975 (8) | 850 (6) | 7928 (3) | 33 (2) |
| C63 | 4164 (8) | 239 (6) | 7761 (3) | 34 (2) |
| C64 | 2409 (8) | 1876 (6) | 8147 (2) | 24.1 (19) |
| F4 | 3009 (5) | 4916 (4) | 7098.0 (15) | 39.0 (7) |
| C55 | 2723 (10) | 3537 (8) | 6673 (3) | 24.1 (10) |
| C56 | 2737 (9) | 2469 (7) | 6667 (3) | 28.8 (11) |
| C57 | 3001 (9) | 1798 (7) | 7025 (3) | 28.8 (11) |
| C58 | 3244 (10) | 2186 (7) | 7400 (3) | 25.1 (11) |
| C59 | 3251 (8) | 3238 (7) | 7417 (3) | 27.7 (12) |
| C60 | 2988 (8) | 3880 (6) | 7058 (3) | 25.2 (12) |
| F4' | 4250 (40) | 4290 (30) | 6890 (11) | 39.0 (7) |
| C55' | 2600 (50) | 3570 (40) | 6678 (10) | 24.1 (10) |
| C56' | 1870 (60) | 2900 (40) | 6769 (12) | 28.8 (11) |
| C57' | 2070 (50) | 2330 (40) | 7150 (12) | 28.8 (11) |
| C58' | 3070 (70) | 2330 (50) | 7432 (14) | 25.1 (11) |
| C59' | 3700 (50) | 3080 (40) | 7358 (11) | 27.7 (12) |
| C60' | 3500 (40) | 3640 (30) | 6983 (10) | 25.2 (12) |
| O9 | 4672 (6) | 3884 (4) | 274.9 (16) | 34.0 (14) |
| N1 | 8035 (6) | 1875 (5) | 1278.0 (19) | 29.7 (16) |
| N2 | 6609 (6) | 4287 (5) | 323.2 (18) | 30.5 (16) |
| C65 | 7595 (8) | 1019 (6) | 1263 (2) | 30 (2) |
| C66 | 6623 (8) | 978 (6) | 984 (2) | 31 (2) |
| C67 | 6065 (8) | 1834 (6) | 702 (2) | 26.3 (19) |
| C68 | 6508 (7) | 2710 (6) | 706 (2) | 23.3 (19) |
| C69 | 7504 (7) | 2693 (6) | 997 (2) | 22.9 (18) |
| C70 | 5871 (9) | 3674 (6) | 417 (2) | 27 (2) |
| O10 | 10307 (5) | 6151 (4) | 9738.9 (15) | 27.4 (13) |
| N3 | 7009 (6) | 8104 (5) | 8717.9 (19) | 29.7 (16) |
| N4 | 8401 (6) | 5702 (5) | 9672.6 (18) | 29.9 (16) |
| C71 | 7426 (8) | 8951 (6) | 8728 (2) | 32 (2) |
| C72 | 8362 (8) | 9034 (6) | 9020 (2) | 30 (2) |
| C73 | 8919 (8) | 8183 (6) | 9306 (2) | 30 (2) |
| C74 | 8492 (7) | 7287 (6) | 9295 (2) | 22.4 (18) |
| C75 | 7535 (8) | 7284 (6) | 8998 (2) | 26.3 (19) |
| C76 | 9129 (8) | 6329 (6) | 9586 (2) | 21.9 (18) |
| O11 | 5485 (6) | 1032 (4) | 9712.3 (15) | 31.5 (13) |
| N5 | 4204 (7) | 3196 (5) | 8714.5 (19) | 28.8 (16) |
| N6 | 3295 (6) | 1052 (5) | 9808.9 (19) | 31.5 (16) |
| C77 | 2876 (9) | 3959 (7) | 8729 (2) | 29 (2) |
| C78 | 1884 (8) | 3958 (6) | 9027 (2) | 28 (2) |
| C79 | 2258 (8) | 3150 (6) | 9328 (2) | 30 (2) |
| C80 | 3651 (8) | 2345 (6) | 9325 (2) | 23.8 (19) |
| C81 | 4569 (8) | 2419 (6) | 9011 (2) | 25.6 (19) |
| C82 | 4199 (9) | 1414 (6) | 9630 (2) | 27 (2) |
| O12 | 10518 (6) | 990 (4) | 9704.9 (15) | 31.6 (13) |
| N7 | 9327 (7) | 3119 (5) | 8695.5 (19) | 29.8 (16) |
| N8 | 8281 (6) | 1072 (5) | 9802.5 (19) | 30.4 (16) |
| C83 | 8011 (9) | 3917 (6) | 8705 (2) | 30 (2) |
| C84 | 7012 (8) | 3947 (6) | 9005 (2) | 31 (2) |
| C85 | 7351 (8) | 3146 (6) | 9313 (2) | 28 (2) |
| C86 | 8711 (8) | 2333 (6) | 9309 (2) | 24.7 (19) |
| C87 | 9655 (8) | 2349 (6) | 8995 (2) | 26.0 (19) |
| C88 | 9240 (9) | 1415 (6) | 9624 (2) | 26.1 (19) |

TABLE A3

Anisotropic Displacement Parameters (Å² × 10³) for CSPNCT-supercell. The Anisotropic displacement factor exponent takes the form: $-2\pi^2[h^2a^{*2}U_{11} + 2hka^*b^*U_{12} + \ldots]$.

| Atom | $U_{11}$ | $U_{22}$ | $U_{33}$ | $U_{23}$ | $U_{13}$ | $U_{12}$ |
|---|---|---|---|---|---|---|
| Cl1 | 51.6 (15) | 36.7 (13) | 46.9 (14) | 20.4 (11) | −3.7 (11) | −14.3 (11) |
| Cl2 | 34.5 (13) | 27.1 (11) | 48.2 (13) | 12.4 (10) | −9.2 (10) | −6.3 (10) |
| O1 | 33 (4) | 21 (3) | 35 (3) | 5 (2) | −10 (3) | −10 (3) |
| O2 | 36 (4) | 23 (3) | 31 (3) | 15 (3) | −7 (3) | −7 (3) |
| C1 | 38 (6) | 24 (5) | 35 (5) | 1 (4) | −1 (4) | −12 (5) |
| C2 | 27 (4) | 10 (3) | 46 (4) | 4 (3) | −21 (3) | −4 (3) |
| C3 | 24 (5) | 22 (5) | 35 (5) | 14 (4) | −12 (4) | −8 (4) |
| C4 | 32 (5) | 23 (5) | 26 (5) | 0 (4) | −4 (4) | −17 (4) |
| C5 | 33 (5) | 25 (5) | 43 (6) | 9 (4) | −10 (4) | −15 (4) |
| C6 | 34 (6) | 38 (6) | 46 (6) | 19 (5) | 1 (4) | −13 (5) |
| C13 | 25 (5) | 16 (4) | 45 (5) | 11 (4) | −8 (4) | −4 (4) |
| C14 | 43 (6) | 28 (5) | 44 (6) | 5 (4) | −6 (4) | −13 (4) |
| C15 | 42 (6) | 28 (5) | 51 (6) | 9 (4) | 6 (4) | −17 (5) |
| C16 | 22 (5) | 25 (5) | 36 (5) | −1 (4) | 6 (4) | −10 (4) |
| F1 | 38.4 (18) | 28.8 (15) | 49.9 (17) | 13.8 (12) | −2.5 (12) | −13.2 (13) |
| C7 | 24 (2) | 21 (2) | 29 (2) | −0.4 (18) | −2.1 (18) | −9.8 (19) |
| C8 | 24 (3) | 20 (3) | 40 (3) | 3 (2) | 0 (2) | −6 (2) |
| C9 | 16 (3) | 22 (3) | 43 (3) | 14 (2) | −4 (2) | −1 (2) |

TABLE A3-continued

Anisotropic Displacement Parameters (Å$^2$ × 10$^3$) for CSPNCT-supercell. The Anisotropic displacement factor exponent takes the form: $-2\pi^2[h^2a^{*2}U_{11} + 2hka^*b^*U_{12} + \ldots]$.

| Atom | $U_{11}$ | $U_{22}$ | $U_{33}$ | $U_{23}$ | $U_{13}$ | $U_{12}$ |
|---|---|---|---|---|---|---|
| C10 | 21 (3) | 22 (2) | 31 (2) | 5.0 (19) | −4.5 (18) | −6 (2) |
| C11 | 20 (3) | 25 (3) | 38 (3) | 10 (2) | −5 (2) | −9 (2) |
| C12 | 14 (3) | 9 (2) | 51 (3) | 5 (2) | 0 (2) | −3 (2) |
| F1' | 38.4 (18) | 28.8 (15) | 49.9 (17) | 13.8 (12) | −2.5 (12) | −13.2 (13) |
| C7' | 24 (2) | 21 (2) | 29 (2) | −0.4 (18) | −2.1 (18) | −9.8 (19) |
| C8' | 24 (3) | 20 (3) | 40 (3) | 3 (2) | 0 (2) | −6 (2) |
| C9' | 16 (3) | 22 (3) | 43 (3) | 14 (2) | −4 (2) | −1 (2) |
| C10' | 21 (3) | 22 (2) | 31 (2) | 5.0 (19) | −4.5 (18) | −6 (2) |
| C11' | 20 (3) | 25 (3) | 38 (3) | 10 (2) | −5 (2) | −9 (2) |
| C12' | 14 (3) | 9 (2) | 51 (3) | 5 (2) | 0 (2) | −3 (2) |
| Cl3 | 63.3 (17) | 37.7 (13) | 53.8 (15) | 24.9 (11) | −16.8 (12) | −22.4 (12) |
| Cl4 | 36.2 (14) | 28.1 (12) | 71.8 (16) | 14.0 (11) | −22.0 (11) | −7.6 (10) |
| O3 | 36 (4) | 23 (3) | 30 (3) | 11 (2) | −14 (2) | −14 (3) |
| O4 | 30 (3) | 26 (3) | 33 (3) | 8 (3) | −7 (3) | −11 (3) |
| C17 | 41 (6) | 11 (4) | 47 (6) | 12 (4) | −19 (5) | −9 (4) |
| C18 | 27 (4) | 10 (3) | 46 (4) | 4 (3) | −21 (3) | −4 (3) |
| C19 | 22 (5) | 24 (5) | 42 (5) | −1 (4) | −9 (4) | −8 (4) |
| C20 | 25 (5) | 24 (5) | 28 (5) | 3 (4) | −10 (4) | −10 (4) |
| C21 | 33 (5) | 28 (5) | 44 (5) | 12 (4) | −3 (4) | −14 (4) |
| C22 | 53 (7) | 35 (5) | 37 (6) | 9 (5) | 9 (5) | −17 (5) |
| C29 | 30 (5) | 25 (5) | 36 (5) | 6 (4) | −4 (4) | −10 (4) |
| C30 | 40 (6) | 14 (4) | 49 (6) | 1 (4) | −3 (4) | −11 (4) |
| C31 | 38 (6) | 27 (5) | 39 (5) | 1 (4) | −3 (4) | −20 (4) |
| C32 | 29 (5) | 12 (4) | 37 (5) | 5 (4) | 0 (4) | −4 (4) |
| F2 | 38.4 (18) | 28.8 (15) | 49.9 (17) | 13.8 (12) | −2.5 (12) | −13.2 (13) |
| C23 | 24 (2) | 21 (2) | 29 (2) | −0.4 (18) | −2.1 (18) | −9.8 (19) |
| C24 | 24 (3) | 20 (3) | 40 (3) | 3 (2) | 0 (2) | −6 (2) |
| C25 | 16 (3) | 22 (3) | 43 (3) | 14 (2) | −4 (2) | −1 (2) |
| C26 | 21 (3) | 22 (3) | 31 (2) | 5.0 (19) | −4.5 (18) | −6 (2) |
| C27 | 20 (3) | 25 (3) | 38 (3) | 10 (2) | −5 (2) | −9 (2) |
| C28 | 14 (3) | 9 (2) | 51 (3) | 5 (2) | 0 (2) | −3 (2) |
| F2' | 38.4 (18) | 28.8 (15) | 49.9 (17) | 13.8 (12) | −2.5 (12) | −13.2 (13) |
| C23' | 24 (2) | 21 (2) | 29 (2) | −0.4 (18) | −2.1 (18) | −9.8 (19) |
| C24' | 24 (3) | 20 (3) | 40 (3) | 3 (2) | 0 (2) | −6 (2) |
| C25' | 16 (3) | 22 (3) | 43 (3) | 14 (2) | −4 (2) | −1 (2) |
| C26' | 21 (3) | 22 (3) | 31 (2) | 5.0 (19) | −4.5 (18) | −6 (2) |
| C27' | 20 (3) | 25 (3) | 38 (3) | 10 (2) | −5 (2) | −9 (2) |
| C28' | 14 (3) | 9 (2) | 51 (3) | 5 (2) | 0 (2) | −3 (2) |
| Cl5 | 52.8 (15) | 25.2 (12) | 68.9 (16) | 9.5 (11) | 9.1 (12) | −18.0 (11) |
| Cl6 | 58.9 (16) | 38.6 (13) | 52.5 (15) | 25.2 (11) | −3.8 (12) | −10.4 (12) |
| O5 | 35 (4) | 18 (3) | 36 (3) | 10 (3) | 2 (3) | −7 (3) |
| O6 | 29 (3) | 22 (3) | 34 (3) | 14 (3) | −6 (3) | −6 (3) |
| C33 | 38 (6) | 32 (5) | 37 (6) | 16 (4) | 4 (4) | −8 (5) |
| C34 | 28 (5) | 13 (4) | 55 (6) | 9 (4) | 14 (4) | 0 (4) |
| C35 | 30 (5) | 23 (5) | 37 (5) | 5 (4) | 3 (4) | −10 (4) |
| C36 | 29 (5) | 20 (4) | 26 (5) | 3 (4) | 3 (4) | −5 (4) |
| C37 | 39 (6) | 26 (5) | 37 (5) | 2 (4) | 0 (4) | −14 (4) |
| C38 | 38 (6) | 35 (5) | 40 (6) | 10 (5) | −8 (4) | −8 (4) |
| C45 | 15 (5) | 21 (5) | 40 (5) | 10 (4) | 0 (4) | 0 (4) |
| C46 | 36 (6) | 27 (5) | 40 (5) | 7 (4) | −7 (4) | −11 (4) |
| C47 | 33 (5) | 20 (5) | 52 (6) | 1 (4) | 3 (4) | −11 (4) |
| C48 | 34 (6) | 13 (5) | 39 (6) | 6 (4) | −12 (4) | −7 (4) |
| F3 | 38.4 (18) | 28.8 (15) | 49.9 (17) | 13.8 (12) | −2.5 (12) | −13.2 (13) |
| C39 | 24 (2) | 21 (2) | 29 (2) | −0.4 (18) | −2.1 (18) | −9.8 (19) |
| C40 | 24 (3) | 20 (3) | 40 (3) | 3 (2) | 0 (2) | −6 (2) |
| C41 | 16 (3) | 22 (3) | 43 (3) | 14 (2) | −4 (2) | −1 (2) |
| C42 | 21 (3) | 22 (2) | 31 (2) | 5.0 (19) | −4.5 (18) | −6 (2) |
| C43 | 20 (3) | 25 (3) | 38 (3) | 10 (2) | −5 (2) | −9 (2) |
| C44 | 14 (3) | 9 (2) | 51 (3) | 5 (2) | 0 (2) | −3 (2) |
| F3' | 38.4 (18) | 28.8 (15) | 49.9 (17) | 13.8 (12) | −2.5 (12) | −13.2 (13) |
| C39' | 24 (2) | 21 (2) | 29 (2) | −0.4 (18) | −2.1 (18) | −9.8 (19) |
| C40' | 24 (3) | 20 (3) | 40 (3) | 3 (2) | 0 (2) | −6 (2) |
| C41' | 16 (3) | 22 (3) | 43 (3) | 14 (2) | −4 (2) | −1 (2) |
| C42' | 21 (3) | 22 (3) | 31 (2) | 5.0 (19) | −4.5 (18) | −6 (2) |
| C43' | 20 (3) | 25 (3) | 38 (3) | 10 (2) | −5 (2) | −9 (2) |
| C44' | 14 (3) | 9 (2) | 51 (3) | 5 (2) | 0 (2) | −3 (2) |
| Cl7 | 43.9 (14) | 30.2 (12) | 48.1 (13) | 18.1 (10) | −4.7 (10) | −18.0 (10) |
| Cl8 | 46.0 (15) | 35.1 (12) | 39.0 (13) | 15.8 (10) | −9.0 (10) | −12.7 (11) |
| O7 | 27 (4) | 21 (3) | 34 (3) | 3 (3) | 1 (2) | −4 (3) |
| O8 | 35 (3) | 20 (3) | 34 (3) | 7 (3) | 0 (3) | −9 (3) |
| C49 | 21 (5) | 28 (5) | 32 (5) | 10 (4) | −2 (4) | −4 (4) |
| C50 | 24 (5) | 18 (4) | 42 (5) | 10 (4) | 8 (4) | −8 (4) |
| C51 | 33 (5) | 18 (4) | 30 (5) | 3 (4) | 2 (4) | −6 (4) |
| C52 | 22 (5) | 29 (5) | 27 (5) | 7 (4) | −1 (4) | −12 (4) |
| C53 | 34 (5) | 25 (5) | 34 (5) | 4 (4) | −5 (4) | −13 (4) |

TABLE A3-continued

Anisotropic Displacement Parameters (Å² × 10³) for CSPNCT-supercell. The Anisotropic displacement factor exponent takes the form: $-2\pi^2[h^2a^{*2}U_{11} + 2hka^*b^*U_{12} + \ldots]$.

| Atom | $U_{11}$ | $U_{22}$ | $U_{33}$ | $U_{23}$ | $U_{13}$ | $U_{12}$ |
|---|---|---|---|---|---|---|
| C54 | 45 (6) | 40 (5) | 33 (5) | 1 (4) | −11 (4) | −23 (5) |
| C61 | 30 (5) | 23 (5) | 34 (5) | 11 (4) | −16 (4) | −12 (4) |
| C62 | 24 (5) | 24 (5) | 50 (6) | 6 (4) | 4 (4) | −7 (4) |
| C63 | 35 (5) | 19 (5) | 43 (5) | 11 (4) | −3 (4) | −5 (4) |
| C64 | 27 (5) | 16 (5) | 31 (5) | 6 (4) | −4 (4) | −10 (4) |
| F4 | 38.4 (18) | 28.8 (15) | 49.9 (17) | 13.8 (12) | −2.5 (12) | −13.2 (13) |
| C55 | 24 (2) | 21 (2) | 29 (2) | −0.4 (18) | −2.1 (18) | −9.8 (19) |
| C56 | 24 (3) | 20 (3) | 40 (3) | 3 (2) | 0 (2) | −6 (2) |
| C57 | 16 (3) | 22 (3) | 43 (3) | 14 (2) | −4 (2) | −1 (2) |
| C58 | 21 (3) | 22 (2) | 31 (2) | 5.0 (19) | −4.5 (18) | −6 (2) |
| C59 | 20 (3) | 25 (3) | 38 (3) | 10 (2) | −5 (2) | −9 (2) |
| C60 | 14 (3) | 9 (2) | 51 (3) | 5 (2) | 0 (2) | −3 (2) |
| F4' | 38.4 (18) | 28.8 (15) | 49.9 (17) | 13.8 (12) | −2.5 (12) | −13.2 (13) |
| C55' | 24 (2) | 21 (2) | 29 (2) | −0.4 (18) | −2.1 (18) | −9.8 (19) |
| C56' | 24 (3) | 20 (3) | 40 (3) | 3 (2) | 0 (2) | −6 (2) |
| C57' | 16 (3) | 22 (3) | 43 (3) | 14 (2) | −4 (2) | −1 (2) |
| C58' | 21 (3) | 22 (2) | 31 (2) | 5.0 (19) | −4.5 (18) | −6 (2) |
| C59' | 20 (3) | 25 (3) | 38 (3) | 10 (2) | −5 (2) | −9 (2) |
| C60' | 14 (3) | 9 (2) | 51 (3) | 5 (2) | 0 (2) | −3 (2) |
| O9 | 27 (4) | 35 (3) | 44 (4) | 20 (3) | −13 (3) | −16 (3) |
| N1 | 32 (4) | 28 (4) | 30 (4) | 10 (3) | −7 (3) | −11 (3) |
| N2 | 31 (4) | 30 (4) | 32 (4) | 18 (3) | −15 (3) | −13 (3) |
| C65 | 27 (5) | 28 (5) | 32 (5) | 3 (4) | −3 (4) | −6 (4) |
| C66 | 35 (5) | 17 (4) | 42 (5) | 7 (4) | −4 (4) | −11 (4) |
| C67 | 26 (5) | 24 (5) | 29 (5) | 1 (4) | −4 (4) | −9 (4) |
| C68 | 21 (5) | 24 (5) | 23 (5) | 8 (4) | −1 (4) | −6 (4) |
| C69 | 18 (5) | 20 (4) | 29 (5) | 10 (4) | 0 (4) | −6 (4) |
| C70 | 34 (6) | 30 (5) | 25 (5) | 4 (4) | −1 (4) | −21 (5) |
| O10 | 27 (4) | 28 (3) | 29 (3) | 14 (2) | −10 (3) | −12 (3) |
| N3 | 24 (4) | 25 (4) | 37 (4) | 7 (3) | −5 (3) | −7 (3) |
| N4 | 28 (4) | 29 (4) | 36 (4) | 19 (3) | −16 (3) | −13 (3) |
| C71 | 34 (5) | 21 (5) | 37 (5) | 11 (4) | −4 (4) | −7 (4) |
| C72 | 35 (5) | 19 (4) | 37 (5) | 6 (4) | −5 (4) | −12 (4) |
| C73 | 24 (5) | 29 (5) | 37 (5) | 3 (4) | −3 (4) | −12 (4) |
| C74 | 19 (5) | 17 (4) | 28 (5) | 0 (4) | 1 (4) | −4 (4) |
| C75 | 28 (5) | 21 (5) | 30 (5) | 11 (4) | 0 (4) | −10 (4) |
| C76 | 27 (5) | 21 (4) | 16 (4) | −1 (3) | −2 (4) | −6 (4) |
| O11 | 24 (4) | 39 (3) | 32 (3) | 18 (3) | −7 (3) | −13 (3) |
| N5 | 29 (5) | 17 (4) | 38 (4) | 11 (3) | −4 (3) | −6 (4) |
| N6 | 20 (4) | 35 (4) | 38 (4) | 17 (3) | −8 (3) | −9 (3) |
| C77 | 34 (6) | 25 (5) | 32 (5) | 6 (4) | −5 (4) | −14 (5) |
| C78 | 25 (5) | 19 (4) | 33 (5) | 3 (4) | −12 (4) | 1 (4) |
| C79 | 25 (6) | 31 (5) | 33 (5) | −5 (4) | 0 (4) | −10 (5) |
| C80 | 29 (6) | 24 (5) | 20 (4) | 4 (4) | −9 (4) | −11 (4) |
| C81 | 24 (5) | 24 (5) | 34 (5) | 8 (4) | −4 (4) | −15 (4) |
| C82 | 26 (6) | 33 (5) | 25 (5) | 4 (4) | −1 (4) | −14 (5) |
| O12 | 21 (4) | 36 (3) | 38 (3) | 21 (3) | −9 (3) | −11 (3) |
| N7 | 32 (5) | 25 (4) | 30 (4) | 3 (3) | −3 (3) | −9 (4) |
| N8 | 21 (4) | 32 (4) | 35 (4) | 25 (3) | −9 (3) | −7 (3) |
| C83 | 37 (6) | 18 (5) | 38 (5) | 3 (4) | −3 (4) | −12 (5) |
| C84 | 18 (5) | 22 (5) | 49 (6) | 3 (4) | −4 (4) | −3 (4) |
| C85 | 30 (6) | 22 (5) | 30 (5) | 4 (4) | −6 (4) | −9 (4) |
| C86 | 23 (5) | 17 (4) | 31 (5) | 6 (4) | −8 (4) | −5 (4) |
| C87 | 25 (5) | 29 (5) | 22 (5) | 6 (4) | −4 (4) | −8 (4) |
| C88 | 23 (6) | 31 (5) | 24 (5) | 7 (4) | −1 (4) | −11 (4) |

TABLE A4

Bond Lengths for CSPNCT-supercell.

| Atom | Atom | Length/Å |
|---|---|---|
| Cl1 | C1 | 1.734(8) |
| Cl2 | C2 | 1.736(8) |
| O1 | C16 | 1.336(9) |
| O2 | C16 | 1.216(9) |
| C1 | C2 | 1.395(11) |
| C1 | C6 | 1.364(11) |
| C2 | C3 | 1.376(10) |
| C3 | C4 | 1.385(10) |
| C4 | C5 | 1.410(10) |
| C4 | C7 | 1.475(10) |
| C4 | C7' | 1.499(19) |
| C5 | C6 | 1.374(11) |
| C13 | C14 | 1.524(11) |
| C13 | C15 | 1.520(10) |
| C13 | C16 | 1.495(11) |
| C13 | C10 | 1.512(10) |
| C13 | C10' | 1.503(19) |
| C14 | C15 | 1.496(11) |
| F1 | C12 | 1.388(9) |
| C7 | C8 | 1.408(11) |

TABLE A4-continued

Bond Lengths for CSPNCT-supercell.

| Atom | Atom | Length/Å |
|---|---|---|
| C7 | C12 | 1.392(10) |
| C8 | C9 | 1.376(11) |
| C9 | C10 | 1.404(12) |
| C10 | C11 | 1.388(12) |
| C11 | C12 | 1.352(10) |
| F1' | C12' | 1.37(2) |
| C7' | C8' | 1.41(2) |
| C7' | C12' | 1.40(2) |
| C8' | C9' | 1.38(2) |
| C9' | C10' | 1.40(2) |
| C10' | C11' | 1.38(2) |
| C11' | C12' | 1.36(2) |
| Cl3 | C17 | 1.725(8) |
| Cl4 | C18 | 1.751(8) |
| O3 | C32 | 1.314(8) |
| O4 | C32 | 1.218(8) |
| C17 | C18 | 1.369(11) |
| C17 | C22 | 1.395(11) |
| C18 | C19 | 1.372(10) |
| C19 | C20 | 1.407(10) |
| C20 | C21 | 1.394(10) |
| C20 | C23 | 1.510(10) |
| C20 | C23' | 1.503(19) |
| C21 | C22 | 1.383(11) |
| C29 | C30 | 1.516(10) |
| C29 | C31 | 1.511(10) |
| C29 | C32 | 1.498(11) |
| C29 | C26 | 1.507(10) |
| C29 | C26' | 1.54(2) |
| C30 | C31 | 1.482(10) |
| F2 | C28 | 1.373(8) |
| C23 | C24 | 1.378(11) |
| C23 | C28 | 1.388(11) |
| C24 | C25 | 1.371(11) |
| C25 | C26 | 1.400(11) |
| C26 | C27 | 1.372(11) |
| C27 | C28 | 1.374(10) |
| F2' | C28' | 1.38(2) |
| C23' | C24' | 1.37(2) |
| C23' | C28' | 1.40(2) |
| C24' | C25' | 1.38(2) |
| C25' | C26' | 1.41(2) |
| C26' | C27' | 1.38(2) |
| C27' | C28' | 1.37(2) |
| Cl5 | C34 | 1.742(8) |
| Cl6 | C33 | 1.718(8) |
| O5 | C48 | 1.323(9) |
| O6 | C48 | 1.228(8) |
| C33 | C34 | 1.384(12) |
| C33 | C38 | 1.367(11) |
| C34 | C35 | 1.385(11) |
| C35 | C36 | 1.397(10) |
| C36 | C37 | 1.395(11) |
| C36 | C39 | 1.481(10) |
| C36 | C39' | 1.485(19) |
| C37 | C38 | 1.392(11) |
| C45 | C46 | 1.510(10) |
| C45 | C47 | 1.509(10) |
| C45 | C48 | 1.501(11) |
| C45 | C42 | 1.506(10) |
| C45 | C42' | 1.498(19) |
| C46 | C47 | 1.480(11) |
| F3 | C44 | 1.363(8) |
| C39 | C40 | 1.417(11) |
| C39 | C44 | 1.382(11) |
| C40 | C41 | 1.376(11) |
| C41 | C42 | 1.404(12) |
| C42 | C43 | 1.402(12) |
| C43 | C44 | 1.371(10) |
| F3' | C44' | 1.36(2) |
| C39' | C40' | 1.42(2) |
| C39' | C44' | 1.38(2) |
| C40' | C41' | 1.38(2) |
| C41' | C42' | 1.40(2) |
| C42' | C43' | 1.40(2) |
| C43' | C44' | 1.37(2) |

TABLE A4-continued

Bond Lengths for CSPNCT-supercell.

| Atom | Atom | Length/Å |
|---|---|---|
| Cl7 | C50 | 1.750(7) |
| Cl8 | C49 | 1.745(8) |
| O7 | C64 | 1.311(8) |
| O8 | C64 | 1.227(8) |
| C49 | C50 | 1.370(11) |
| C49 | C54 | 1.370(10) |
| C50 | C51 | 1.382(10) |
| C51 | C52 | 1.383(10) |
| C52 | C53 | 1.402(10) |
| C52 | C55 | 1.490(10) |
| C52 | C55' | 1.479(19) |
| C53 | C54 | 1.372(11) |
| C61 | C62 | 1.517(10) |
| C61 | C63 | 1.516(10) |
| C61 | C64 | 1.491(10) |
| C61 | C58 | 1.520(10) |
| C61 | C58' | 1.534(19) |
| C62 | C63 | 1.464(11) |
| F4 | C60 | 1.364(8) |
| C55 | C56 | 1.384(11) |
| C55 | C60 | 1.383(11) |
| C56 | C57 | 1.406(11) |
| C57 | C58 | 1.371(12) |
| C58 | C59 | 1.375(11) |
| C59 | C60 | 1.389(10) |
| F4' | C60' | 1.37(2) |
| C55' | C56' | 1.38(2) |
| C55' | C60' | 1.39(2) |
| C56' | C57' | 1.40(2) |
| C57' | C58' | 1.38(2) |
| C58' | C59' | 1.38(2) |
| C59' | C60' | 1.39(2) |
| O9 | C70 | 1.246(8) |
| N1 | C65 | 1.355(9) |
| N1 | C69 | 1.344(9) |
| N2 | C70 | 1.323(9) |
| C65 | C66 | 1.369(10) |
| C66 | C67 | 1.381(10) |
| C67 | C68 | 1.380(10) |
| C68 | C69 | 1.391(10) |
| C68 | C70 | 1.497(10) |
| O10 | C76 | 1.248(8) |
| N3 | C71 | 1.328(9) |
| N3 | C75 | 1.344(9) |
| N4 | C76 | 1.326(9) |
| C71 | C72 | 1.387(11) |
| C72 | C73 | 1.387(10) |
| C73 | C74 | 1.396(10) |
| C74 | C75 | 1.381(10) |
| C74 | C76 | 1.496(10) |
| O11 | C82 | 1.247(8) |
| N5 | C77 | 1.338(9) |
| N5 | C81 | 1.336(9) |
| N6 | C82 | 1.310(9) |
| C77 | C78 | 1.378(10) |
| C78 | C79 | 1.371(10) |
| C79 | C80 | 1.405(10) |
| C80 | C81 | 1.389(10) |
| C80 | C82 | 1.494(10) |
| O12 | C88 | 1.240(8) |
| N7 | C83 | 1.345(9) |
| N7 | C87 | 1.338(9) |
| N8 | C88 | 1.342(9) |
| C83 | C84 | 1.376(10) |
| C84 | C85 | 1.383(10) |
| C85 | C86 | 1.385(10) |
| C86 | C87 | 1.385(10) |
| C86 | C88 | 1.502(10) |

TABLE A5

Bond Angles for CSPNCT-supercell.

| Atom | Atom | Atom | Angle/° |
|---|---|---|---|
| C2 | C1 | Cl1 | 119.8 (6) |
| C6 | C1 | Cl1 | 120.9 (6) |
| C6 | C1 | C2 | 119.4 (7) |
| C1 | C2 | Cl2 | 120.8 (6) |
| C3 | C2 | Cl2 | 119.2 (6) |
| C3 | C2 | C1 | 119.9 (7) |
| C2 | C3 | C4 | 121.8 (7) |
| C3 | C4 | C5 | 116.8 (7) |
| C3 | C4 | C7 | 123.8 (7) |
| C3 | C4 | C7' | 123.1 (15) |
| C5 | C4 | C7 | 119.4 (7) |
| C5 | C4 | C7' | 118.5 (14) |
| C6 | C5 | C4 | 121.5 (8) |
| C1 | C6 | C5 | 120.5 (8) |
| C15 | C13 | C14 | 58.9 (5) |
| C16 | C13 | C14 | 112.1 (6) |
| C16 | C13 | C15 | 113.7 (7) |
| C16 | C13 | C10 | 120.3 (8) |
| C16 | C13 | C10' | 123 (3) |
| C10 | C13 | C14 | 118.0 (7) |
| C10 | C13 | C15 | 118.8 (8) |
| C10' | C13 | C14 | 114 (2) |
| C10' | C13 | C15 | 118 (4) |
| C15 | C14 | C13 | 60.4 (5) |
| C14 | C15 | C13 | 60.7 (5) |
| O1 | C16 | C13 | 112.5 (7) |
| O2 | C16 | O1 | 123.7 (7) |
| O2 | C16 | C13 | 123.8 (7) |
| C8 | C7 | C4 | 122.1 (7) |
| C12 | C7 | C4 | 124.9 (7) |
| C12 | C7 | C8 | 112.8 (7) |
| C9 | C8 | C7 | 122.8 (8) |
| C8 | C9 | C10 | 121.1 (8) |
| C9 | C10 | C13 | 120.8 (8) |
| C11 | C10 | C13 | 121.9 (8) |
| C11 | C10 | C9 | 117.3 (7) |
| C12 | C11 | C10 | 119.3 (8) |
| F1 | C12 | C7 | 116.7 (7) |
| C11 | C12 | F1 | 116.7 (7) |
| C11 | C12 | C7 | 126.6 (8) |
| C8' | C7' | C4 | 123 (2) |
| C12' | C7' | C4 | 122 (2) |
| C12' | C7' | C8' | 110.5 (19) |
| C9' | C8' | C7' | 127 (2) |
| C8' | C9' | C10' | 118 (2) |
| C9' | C10' | C13 | 123 (2) |
| C11' | C10' | C13 | 119 (2) |
| C11' | C10' | C9' | 118 (2) |
| C12' | C11' | C10' | 121 (2) |
| F1' | C12' | C7' | 120 (2) |
| C11' | C12' | F1' | 113 (2) |
| C11' | C12' | C7' | 126 (2) |
| C18 | C17 | Cl3 | 123.5 (6) |
| C18 | C17 | C22 | 117.3 (7) |
| C22 | C17 | Cl3 | 119.2 (7) |
| C17 | C18 | Cl4 | 119.1 (6) |
| C17 | C18 | C19 | 123.3 (7) |
| C19 | C18 | Cl4 | 117.6 (7) |
| C18 | C19 | C20 | 119.5 (7) |
| C19 | C20 | C23 | 123.3 (7) |
| C19 | C20 | C23' | 123.7 (14) |
| C21 | C20 | C19 | 118.0 (7) |
| C21 | C20 | C23 | 118.7 (7) |
| C21 | C20 | C23' | 117.9 (13) |
| C22 | C21 | C20 | 120.8 (8) |
| C21 | C22 | C17 | 121.1 (8) |
| C30 | C29 | C26' | 127 (3) |
| C31 | C29 | C30 | 58.6 (5) |
| C31 | C29 | C26' | 124 (2) |
| C32 | C29 | C30 | 113.6 (7) |
| C32 | C29 | C31 | 113.9 (7) |
| C32 | C29 | C26 | 119.1 (7) |
| C32 | C29 | C26' | 111 (3) |
| C26 | C29 | C30 | 118.4 (7) |
| C26 | C29 | C31 | 119.0 (7) |
| C31 | C30 | C29 | 60.5 (5) |

TABLE A5-continued

Bond Angles for CSPNCT-supercell.

| Atom | Atom | Atom | Angle/° |
|---|---|---|---|
| C30 | C31 | C29 | 60.9 (5) |
| O3 | C32 | C29 | 114.5 (7) |
| O4 | C32 | O3 | 122.6 (7) |
| O4 | C32 | C29 | 122.9 (7) |
| C24 | C23 | C20 | 122.4 (7) |
| C24 | C23 | C28 | 113.7 (7) |
| C28 | C23 | C20 | 123.7 (7) |
| C25 | C24 | C23 | 124.3 (8) |
| C24 | C25 | C26 | 119.8 (8) |
| C25 | C26 | C29 | 121.3 (8) |
| C27 | C26 | C29 | 121.3 (8) |
| C27 | C26 | C25 | 117.4 (7) |
| C26 | C27 | C28 | 120.4 (8) |
| F2 | C28 | C23 | 119.3 (7) |
| F2 | C28 | C27 | 116.5 (7) |
| C27 | C28 | C23 | 124.1 (7) |
| C24' | C23' | C20 | 121 (2) |
| C24' | C23' | C28' | 116.3 (18) |
| C28' | C23' | C20 | 122 (2) |
| C23' | C24' | C25' | 123 (2) |
| C24' | C25' | C26' | 121 (2) |
| C25' | C26' | C29 | 120 (2) |
| C27' | C26' | C29 | 123 (2) |
| C27' | C26' | C25' | 116.0 (19) |
| C28' | C27' | C26' | 122 (2) |
| F2' | C28' | C23' | 114 (2) |
| C27' | C28' | F2' | 123 (2) |
| C27' | C28' | C23' | 121 (2) |
| C34 | C33 | Cl6 | 121.2 (7) |
| C38 | C33 | Cl6 | 121.0 (7) |
| C38 | C33 | C34 | 117.8 (7) |
| C33 | C34 | Cl5 | 120.0 (6) |
| C33 | C34 | C35 | 121.9 (7) |
| C35 | C34 | Cl5 | 118.0 (7) |
| C34 | C35 | C36 | 120.4 (8) |
| C35 | C36 | C39 | 122.9 (7) |
| C35 | C36 | C39' | 125.9 (14) |
| C37 | C36 | C35 | 117.2 (7) |
| C37 | C36 | C39 | 119.8 (7) |
| C37 | C36 | C39' | 116.9 (14) |
| C38 | C37 | C36 | 121.1 (8) |
| C33 | C38 | C37 | 121.4 (8) |
| C47 | C45 | C46 | 58.7 (5) |
| C48 | C45 | C46 | 112.3 (7) |
| C48 | C45 | C47 | 112.9 (6) |
| C48 | C45 | C42 | 119.3 (8) |
| C42 | C45 | C46 | 119.9 (8) |
| C42 | C45 | C47 | 119.3 (8) |
| C42' | C45 | C46 | 119 (4) |
| C42' | C45 | C47 | 117 (3) |
| C42' | C45 | C48 | 121 (4) |
| C47 | C46 | C45 | 60.6 (5) |
| C46 | C47 | C45 | 60.7 (5) |
| O5 | C48 | C45 | 113.5 (7) |
| O6 | C48 | O5 | 123.1 (7) |
| O6 | C48 | C45 | 123.4 (7) |
| C40 | C39 | C36 | 120.9 (7) |
| C44 | C39 | C36 | 124.9 (7) |
| C44 | C39 | C40 | 114.1 (7) |
| C41 | C40 | C39 | 122.0 (8) |
| C40 | C41 | C42 | 121.5 (8) |
| C41 | C42 | C45 | 120.3 (8) |
| C43 | C42 | C45 | 122.1 (8) |
| C43 | C42 | C41 | 117.6 (7) |
| C44 | C43 | C42 | 118.7 (8) |
| F3 | C44 | C39 | 117.6 (7) |
| F3 | C44 | C43 | 116.3 (7) |
| C43 | C44 | C39 | 126.0 (7) |
| C40' | C39' | C36 | 124 (2) |
| C44' | C39' | C36 | 122 (2) |
| C44' | C39' | C40' | 113.5 (18) |
| C41' | C40' | C39' | 123 (2) |
| C40' | C41' | C42' | 120 (2) |
| C41' | C42' | C45 | 121 (2) |
| C43' | C42' | C45 | 121 (2) |
| C43' | C42' | C41' | 117.8 (18) |

TABLE A5-continued

Bond Angles for CSPNCT-supercell.

| Atom | Atom | Atom | Angle/° |
|---|---|---|---|
| C44' | C43' | C42' | 120 (2) |
| F3' | C44' | C39' | 120 (2) |
| F3' | C44' | C43' | 115 (2) |
| C43' | C44' | C39' | 125 (2) |
| C50 | C49 | Cl8 | 121.6 (6) |
| C54 | C49 | Cl8 | 119.3 (6) |
| C54 | C49 | C50 | 119.0 (7) |
| C49 | C50 | Cl7 | 120.2 (6) |
| C49 | C50 | C51 | 120.8 (7) |
| C51 | C50 | Cl7 | 119.0 (6) |
| C50 | C51 | C52 | 121.3 (7) |
| C51 | C52 | C53 | 116.8 (7) |
| C51 | C52 | C55 | 124.0 (7) |
| C51 | C52 | C55' | 126.5 (14) |
| C53 | C52 | C55 | 119.2 (7) |
| C53 | C52 | C55' | 116.5 (13) |
| C54 | C53 | C52 | 121.4 (7) |
| C49 | C54 | C53 | 120.7 (7) |
| C62 | C61 | C58 | 117.8 (7) |
| C62 | C61 | C58' | 124 (2) |
| C63 | C61 | C62 | 57.7 (5) |
| C63 | C61 | C58 | 119.0 (7) |
| C63 | C61 | C58' | 127 (3) |
| C64 | C61 | C62 | 114.2 (6) |
| C64 | C61 | C63 | 112.7 (6) |
| C64 | C61 | C58 | 120.1 (7) |
| C64 | C61 | C58' | 112 (3) |
| C63 | C62 | C61 | 61.1 (5) |
| C62 | C63 | C61 | 61.2 (5) |
| O7 | C64 | C61 | 114.6 (7) |
| O8 | C64 | O7 | 123.3 (7) |
| O8 | C64 | C61 | 122.2 (7) |
| C56 | C55 | C52 | 122.2 (7) |
| C60 | C55 | C52 | 123.3 (7) |
| C60 | C55 | C56 | 114.4 (7) |
| C55 | C56 | C57 | 122.4 (8) |
| C58 | C57 | C56 | 120.7 (8) |
| C57 | C58 | C61 | 121.7 (8) |
| C57 | C58 | C59 | 118.6 (7) |
| C59 | C58 | C61 | 119.7 (8) |
| C58 | C59 | C60 | 119.2 (8) |
| F4 | C60 | C55 | 119.2 (7) |
| F4 | C60 | C59 | 116.1 (7) |
| C55 | C60 | C59 | 124.7 (7) |
| C56' | C55' | C52 | 123 (2) |
| C56' | C55' | C60' | 115.9 (18) |
| C60' | C55' | C52 | 121 (2) |
| C55' | C56' | C57' | 120 (2) |
| C58' | C57' | C56' | 123 (2) |
| C57' | C58' | C61 | 121 (2) |
| C57' | C58' | C59' | 116.0 (19) |
| C59' | C58' | C61 | 123 (2) |
| C58' | C59' | C60' | 120 (2) |
| F4' | C60' | C55' | 116 (2) |
| F4' | C60' | C59' | 120 (2) |
| C55' | C60' | C59' | 124 (2) |
| C69 | N1 | C65 | 117.4 (6) |
| N1 | C65 | C66 | 122.7 (7) |
| C65 | C66 | C67 | 119.4 (7) |
| C68 | C67 | C66 | 119.2 (7) |
| C67 | C68 | C69 | 118.2 (7) |
| C67 | C68 | C70 | 120.3 (7) |
| C69 | C68 | C70 | 121.4 (7) |
| N1 | C69 | C68 | 123.1 (7) |
| O9 | C70 | N2 | 121.8 (7) |
| O9 | C70 | C68 | 119.9 (6) |
| N2 | C70 | C68 | 118.3 (7) |
| C71 | N3 | C75 | 118.5 (7) |
| N3 | C71 | C72 | 122.8 (7) |
| C71 | C72 | C73 | 118.8 (7) |
| C72 | C73 | C74 | 118.7 (7) |
| C73 | C74 | C76 | 119.8 (7) |
| C75 | C74 | C73 | 118.5 (7) |
| C75 | C74 | C76 | 121.5 (6) |
| N3 | C75 | C74 | 122.7 (7) |
| O10 | C76 | N4 | 122.5 (7) |
| O10 | C76 | C74 | 119.6 (6) |
| N4 | C76 | C74 | 117.9 (7) |
| C81 | N5 | C77 | 117.2 (7) |
| N5 | C77 | C78 | 123.1 (7) |
| C79 | C78 | C77 | 119.5 (7) |
| C78 | C79 | C80 | 118.9 (7) |
| C79 | C80 | C82 | 124.6 (7) |
| C81 | C80 | C79 | 117.2 (7) |
| C81 | C80 | C82 | 118.2 (7) |
| N5 | C81 | C80 | 124.1 (7) |
| O11 | C82 | N6 | 122.7 (7) |
| O11 | C82 | C80 | 119.0 (7) |
| N6 | C82 | C80 | 118.3 (8) |
| C87 | N7 | C83 | 117.6 (7) |
| N7 | C83 | C84 | 122.3 (7) |
| C83 | C84 | C85 | 120.0 (7) |
| C84 | C85 | C86 | 118.0 (7) |
| C85 | C86 | C88 | 124.2 (7) |
| C87 | C86 | C85 | 118.7 (7) |
| C87 | C86 | C88 | 117.1 (7) |
| N7 | C87 | C86 | 123.4 (7) |
| O12 | C88 | N8 | 122.5 (7) |
| O12 | C88 | C86 | 120.3 (7) |
| N8 | C88 | C86 | 117.2 (7) |

TABLE A6

Torsion Angles for CSPNCT-supercell.

| A | B | C | D | Angle/° |
|---|---|---|---|---|
| Cl1 | C1 | C2 | Cl2 | 4.0 (9) |
| Cl1 | C1 | C2 | C3 | −177.0 (6) |
| Cl1 | C1 | C6 | C5 | 178.3 (6) |
| Cl2 | C2 | C3 | C4 | 177.5 (5) |
| C1 | C2 | C3 | C4 | −1.5 (11) |
| C2 | C1 | C6 | C5 | −0.3 (12) |
| C2 | C3 | C4 | C5 | −0.1 (10) |
| C2 | C3 | C4 | C7 | 177.6 (7) |
| C2 | C3 | C4 | C7' | −165 (2) |
| C3 | C4 | C5 | C6 | 1.5 (11) |
| C3 | C4 | C7 | C8 | −154.5 (7) |
| C3 | C4 | C7 | C12 | 31.7 (12) |
| C3 | C4 | C7' | C8' | 166.9 (16) |
| C3 | C4 | C7' | C12' | −39 (5) |
| C4 | C5 | C6 | C1 | −1.3 (12) |
| C4 | C7 | C8 | C9 | −172.9 (8) |
| C4 | C7 | C12 | F1 | −5.1 (12) |
| C4 | C7 | C12 | C11 | 175.6 (8) |
| C4 | C7' | C8' | C9' | 160 (5) |
| C4 | C7' | C12' | F1' | 27 (6) |
| C4 | C7' | C12' | C11' | −165 (5) |
| C5 | C4 | C7 | C8 | 23.2 (11) |
| C5 | C4 | C7 | C12 | −150.7 (8) |
| C5 | C4 | C7' | C8' | 2 (3) |
| C5 | C4 | C7' | C12' | 156 (3) |
| C6 | C1 | C2 | Cl2 | −177.3 (6) |
| C6 | C1 | C2 | C3 | 1.7 (11) |
| C13 | C10 | C11 | C12 | −177.5 (8) |
| C13 | C10' | C11' | C12' | −178 (6) |
| C14 | C13 | C16 | O1 | 145.2 (6) |
| C14 | C13 | C16 | O2 | −34.7 (10) |
| C14 | C13 | C10 | C9 | −70.5 (13) |
| C14 | C13 | C10 | C11 | 109.4 (11) |
| C14 | C13 | C10' | C9' | −25 (7) |
| C14 | C13 | C10' | C11' | 148 (4) |
| C15 | C13 | C16 | O1 | −150.3 (6) |
| C15 | C13 | C16 | O2 | 29.8 (11) |
| C15 | C13 | C10 | C9 | −138.4 (10) |
| C15 | C13 | C10 | C11 | 41.4 (14) |
| C15 | C13 | C10' | C9' | −91 (6) |
| C15 | C13 | C10' | C11' | 82 (6) |
| C16 | C13 | C14 | C15 | 105.1 (7) |

TABLE A6-continued

Torsion Angles for CSPNCT-supercell.

| A | B | C | D | Angle/° |
|---|---|---|---|---|
| C16 | C13 | C15 | C14 | −102.5 (7) |
| C16 | C13 | C10 | C9 | 73.2 (12) |
| C16 | C13 | C10 | C11 | −107.0 (12) |
| C16 | C13 | C10' | C9' | 116 (5) |
| C16 | C13 | C10' | C11' | −70 (6) |
| C7 | C4 | C5 | C6 | −176.4 (7) |
| C7 | C8 | C9 | C10 | −2.4 (14) |
| C8 | C7 | C12 | F1 | −179.5 (7) |
| C8 | C7 | C12 | C11 | 1.2 (13) |
| C8 | C9 | C10 | C13 | −179.8 (8) |
| C8 | C9 | C10 | C11 | 0.3 (16) |
| C9 | C10 | C11 | C12 | 2.4 (16) |
| C10 | C13 | C14 | C15 | −108.4 (9) |
| C10 | C13 | C15 | C14 | 107.1 (8) |
| C10 | C13 | C16 | O1 | −0.4 (10) |
| C10 | C13 | C16 | O2 | 179.7 (7) |
| C10 | C11 | C12 | F1 | 177.4 (9) |
| C10 | C11 | C12 | C7 | −3.3 (15) |
| C12 | C7 | C8 | C9 | 1.6 (12) |
| C7' | C4 | C5 | C6 | 167 (2) |
| C7' | C8' | C9' | C10' | −1 (5) |
| C8' | C7' | C12' | F1' | −176 (2) |
| C8' | C7' | C12' | C11' | −8 (4) |
| C8' | C9' | C10' | C13 | 174 (6) |
| C8' | C9' | C10' | C11' | 1 (6) |
| C9' | C10' | C11' | C12' | −4 (7) |
| C10' | C13 | C14 | C15 | −109 (3) |
| C10' | C13 | C15 | C14 | 102.5 (18) |
| C10' | C13 | C16 | O1 | 3 (2) |
| C10' | C13 | C16 | O2 | −177 (2) |
| C10' | C11' | C12' | F1' | 177 (4) |
| C10' | C11' | C12' | C7' | 9 (7) |
| C12' | C7' | C8' | C9' | 4 (3) |
| C13 | C17 | C18 | C14 | −1.6 (9) |
| C13 | C17 | C18 | C19 | −179.6 (6) |
| C13 | C17 | C22 | C21 | 177.7 (6) |
| C14 | C18 | C19 | C20 | −176.7 (5) |
| C17 | C18 | C19 | C20 | 1.3 (11) |
| C18 | C17 | C22 | C21 | −1.7 (12) |
| C18 | C19 | C20 | C21 | −0.6 (10) |
| C18 | C19 | C20 | C23 | 177.8 (7) |
| C18 | C19 | C20 | C23' | 172 (3) |
| C19 | C20 | C21 | C22 | −1.2 (11) |
| C19 | C20 | C23 | C24 | 156.3 (8) |
| C19 | C20 | C23 | C28 | −27.5 (13) |
| C19 | C20 | C23' | C24' | −161.9 (14) |
| C19 | C20 | C23' | C28' | 13 (6) |
| C20 | C21 | C22 | C17 | 2.4 (12) |
| C20 | C23 | C24 | C25 | 176.5 (8) |
| C20 | C23 | C28 | F2 | 2.1 (13) |
| C20 | C23 | C28 | C27 | −175.7 (8) |
| C20 | C23' | C24' | C25' | 175 (6) |
| C20 | C23' | C28' | F2' | 7 (7) |
| C20 | C23' | C28' | C27' | 178 (5) |
| C21 | C20 | C23 | C24 | −25.3 (13) |
| C21 | C20 | C23 | C28 | 150.9 (8) |
| C21 | C20 | C23' | C24' | 11 (3) |
| C21 | C20 | C23' | C28' | −174 (4) |
| C22 | C17 | C18 | C14 | 177.8 (6) |
| C22 | C17 | C18 | C19 | −0.2 (11) |
| C29 | C26 | C27 | C28 | 178.5 (8) |
| C29 | C26' | C27' | C28' | −170 (6) |
| C30 | C29 | C32 | O3 | 145.3 (7) |
| C30 | C29 | C32 | O4 | −34.6 (10) |
| C30 | C29 | C26 | C25 | −33.7 (12) |
| C30 | C29 | C26 | C27 | 144.2 (9) |
| C30 | C29 | C26' | C25' | −70 (6) |
| C30 | C29 | C26' | C27' | 99 (5) |
| C31 | C29 | C32 | O3 | −150.1 (6) |
| C31 | C29 | C32 | O4 | 30.1 (11) |
| C31 | C29 | C26 | C25 | −101.6 (10) |
| C31 | C29 | C26 | C27 | 76.3 (11) |
| C31 | C29 | C26' | C25' | −144 (4) |
| C31 | C29 | C26' | C27' | 25 (7) |
| C32 | C29 | C30 | C31 | 104.6 (7) |
| C32 | C29 | C31 | C30 | −104.0 (7) |
| C32 | C29 | C26 | C25 | 111.4 (10) |
| C32 | C29 | C26 | C27 | −70.6 (11) |
| C32 | C29 | C26' | C25' | 75 (5) |
| C32 | C29 | C26' | C27' | −116 (5) |
| C23 | C20 | C21 | C22 | −179.7 (8) |
| C23 | C24 | C25 | C26 | −2.5 (14) |
| C24 | C23 | C28 | F2 | 178.5 (8) |
| C24 | C23 | C28 | C27 | 0.8 (13) |
| C24 | C25 | C26 | C29 | −177.8 (8) |
| C24 | C25 | C26 | C27 | 4.2 (13) |
| C25 | C26 | C27 | C28 | −3.5 (13) |
| C26 | C29 | C30 | C31 | −108.4 (8) |
| C26 | C29 | C31 | C30 | 107.4 (8) |
| C26 | C29 | C32 | O3 | −1.5 (10) |
| C26 | C29 | C32 | O4 | 178.7 (7) |
| C26 | C27 | C28 | F2 | −176.8 (8) |
| C26 | C27 | C28 | C23 | 1.1 (14) |
| C28 | C23 | C24 | C25 | 0.0 (14) |
| C23' | C20 | C21 | C22 | −175 (3) |
| C23' | C24' | C25' | C26' | 7 (6) |
| C24' | C23' | C28' | F2' | −178 (2) |
| C24' | C23' | C28' | C27' | −6 (5) |
| C24' | C25' | C26' | C29 | 164 (5) |
| C24' | C25' | C26' | C27' | −7 (7) |
| C25' | C26' | C27' | C28' | 0 (8) |
| C26' | C29 | C30 | C31 | −111 (2) |
| C26' | C29 | C31 | C30 | 116 (3) |
| C26' | C29 | C32 | O3 | −4.8 (18) |
| C26' | C29 | C32 | O4 | 175.4 (17) |
| C26' | C27' | C28' | F2' | 178 (4) |
| C26' | C27' | C28' | C23' | 7 (8) |
| C28' | C23' | C24' | C25' | −1 (3) |
| Cl5 | C34 | C35 | C36 | 179.0 (6) |
| Cl6 | C33 | C34 | Cl5 | 1.0 (10) |
| Cl6 | C33 | C34 | C35 | −177.2 (6) |
| Cl6 | C33 | C38 | C37 | 178.9 (6) |
| C33 | C34 | C35 | C36 | −2.8 (12) |
| C34 | C33 | C38 | C37 | −2.3 (12) |
| C34 | C35 | C36 | C37 | −0.2 (11) |
| C34 | C35 | C36 | C39 | 178.2 (8) |
| C34 | C35 | C36 | C39' | −179 (3) |
| C35 | C36 | C37 | C38 | 1.9 (11) |
| C35 | C36 | C39 | C40 | −150.2 (9) |
| C35 | C36 | C39 | C44 | 31.7 (14) |
| C35 | C36 | C39' | C40' | 171.8 (15) |
| C35 | C36 | C39' | C44' | −11 (5) |
| C36 | C37 | C38 | C33 | −0.6 (12) |
| C36 | C39 | C40 | C41 | −176.5 (8) |
| C36 | C39 | C44 | F3 | −0.4 (14) |
| C36 | C39 | C44 | C43 | 177.5 (8) |
| C36 | C39' | C40' | C41' | 178 (6) |
| C36 | C39' | C44' | F3' | 3 (7) |
| C36 | C39' | C44' | C43' | 179 (6) |
| C37 | C36 | C39 | C40 | 28.2 (14) |
| C37 | C36 | C39 | C44 | −150.0 (9) |
| C37 | C36 | C39' | C40' | −7 (4) |
| C37 | C36 | C39' | C44' | 171 (4) |
| C38 | C33 | C34 | Cl5 | −177.9 (6) |
| C38 | C33 | C34 | C35 | 4.0 (12) |
| C45 | C42 | C43 | C44 | −178.7 (9) |
| C45 | C42' | C43' | C44' | 177 (7) |
| C46 | C45 | C48 | O5 | −154.3 (6) |
| C46 | C45 | C48 | O6 | 27.9 (10) |
| C46 | C45 | C42 | C41 | −143.4 (10) |
| C46 | C45 | C42 | C43 | 37.0 (15) |
| C46 | C45 | C42' | C41' | −106 (6) |
| C46 | C45 | C42' | C43' | 75 (5) |
| C47 | C45 | C48 | O5 | 141.5 (7) |
| C47 | C45 | C48 | O6 | −36.3 (10) |
| C47 | C45 | C42 | C41 | −74.8 (14) |
| C47 | C45 | C42 | C43 | 105.6 (11) |
| C47 | C45 | C42' | C41' | −38 (8) |
| C47 | C45 | C42' | C43' | 142 (5) |
| C48 | C45 | C46 | C47 | −104.1 (7) |
| C48 | C45 | C47 | C46 | 103.0 (7) |
| C48 | C45 | C42 | C41 | 71.0 (13) |

TABLE A6-continued

Torsion Angles for CSPNCT-supercell.

| A | B | C | D | Angle/° |
|---|---|---|---|---|
| C48 | C45 | C42 | C43 | −108.6 (13) |
| C48 | C45 | C42' | C41' | 106 (6) |
| C48 | C45 | C42' | C43' | −73 (7) |
| C39 | C36 | C37 | C38 | −176.6 (8) |
| C39 | C40 | C41 | C42 | −1.2 (16) |
| C40 | C39 | C44 | F3 | −178.7 (8) |
| C40 | C39 | C44 | C43 | −0.8 (15) |
| C40 | C41 | C42 | C45 | 179.7 (9) |
| C40 | C41 | C42 | C43 | −0.6 (17) |
| C41 | C42 | C43 | C44 | 1.7 (17) |
| C42 | C45 | C46 | C47 | 108.1 (9) |
| C42 | C45 | C47 | C46 | −109.2 (9) |
| C42 | C45 | C48 | O5 | −6.3 (10) |
| C42 | C45 | C48 | O6 | 175.9 (7) |
| C42 | C43 | C44 | F3 | 176.9 (9) |
| C42 | C43 | C44 | C39 | −1.0 (16) |
| C44 | C39 | C40 | C41 | 1.9 (15) |
| C39' | C36 | C37 | C38 | −180 (3) |
| C39' | C40' | C41' | C42' | 2 (5) |
| C40' | C39' | C44' | F3' | −179 (2) |
| C40' | C39' | C44' | C43' | −3 (5) |
| C40' | C41' | C42' | C45 | −180 (7) |
| C40' | C41' | C42' | C43' | 0 (7) |
| C41' | C42' | C43' | C44' | −3 (7) |
| C42' | C45 | C46 | C47 | 105 (2) |
| C42' | C45 | C47 | C46 | −110 (3) |
| C42' | C45 | C48 | O5 | −4 (2) |
| C42' | C45 | C48 | O6 | 177.9 (19) |
| C42' | C43' | C44' | F3' | −179 (4) |
| C42' | C43' | C44' | C39' | 4 (7) |
| C44' | C39' | C40' | C41' | 0 (3) |
| Cl7 | C50 | C51 | C52 | 178.3 (6) |
| Cl8 | C49 | C50 | Cl7 | 0.2 (10) |
| Cl8 | C49 | C50 | C51 | 178.3 (6) |
| Cl8 | C49 | C54 | C53 | −178.4 (6) |
| C49 | C50 | C51 | C52 | 0.2 (11) |
| C50 | C49 | C54 | C53 | 0.3 (12) |
| C50 | C51 | C52 | C53 | 0.0 (11) |
| C50 | C51 | C52 | C55 | −179.4 (8) |
| C50 | C51 | C52 | C55' | −175 (3) |
| C51 | C52 | C53 | C54 | 0.0 (11) |
| C51 | C52 | C55 | C56 | −153.5 (9) |
| C51 | C52 | C55 | C60 | 31.9 (14) |
| C51 | C52 | C55' | C56' | 166.9 (14) |
| C51 | C52 | C55' | C60' | −6 (6) |
| C52 | C53 | C54 | C49 | −0.1 (12) |
| C52 | C55 | C56 | C57 | −175.1 (8) |
| C52 | C55 | C60 | F4 | −5.5 (13) |
| C52 | C55 | C60 | C59 | 175.0 (8) |
| C52 | C55' | C56' | C57' | −174 (6) |
| C52 | C55' | C60' | F4' | −8 (7) |
| C52 | C55' | C60' | C59' | 174 (5) |
| C53 | C52 | C55 | C56 | 27.1 (14) |
| C53 | C52 | C55 | C60 | −147.5 (8) |
| C53 | C52 | C55' | C56' | −8 (3) |
| C53 | C52 | C55' | C60' | 179 (4) |
| C54 | C49 | C50 | Cl7 | −178.4 (6) |
| C54 | C49 | C50 | C51 | −0.4 (12) |
| C61 | C58 | C59 | C60 | −177.2 (8) |
| C61 | C58' | C59' | C60' | 167 (6) |
| C62 | C61 | C64 | O7 | 151.8 (6) |
| C62 | C61 | C64 | O8 | −29.2 (10) |
| C62 | C61 | C58 | C57 | 98.3 (10) |
| C62 | C61 | C58 | C59 | −83.4 (11) |
| C62 | C61 | C58' | C57' | 136 (4) |
| C62 | C61 | C58' | C59' | −42 (7) |
| C63 | C61 | C64 | O7 | −144.7 (6) |
| C63 | C61 | C64 | O8 | 34.2 (10) |
| C63 | C61 | C58 | C57 | 31.8 (13) |
| C63 | C61 | C58 | C59 | −149.9 (8) |
| C63 | C61 | C58' | C57' | 64 (6) |
| C63 | C61 | C58' | C59' | −114 (5) |
| C64 | C61 | C62 | C63 | 102.4 (7) |
| C64 | C61 | C63 | C62 | −105.2 (7) |
| C64 | C61 | C58 | C57 | −114.4 (10) |
| C64 | C61 | C58 | C59 | 63.9 (11) |
| C64 | C61 | C58' | C57' | −81 (6) |
| C64 | C61 | C58' | C59' | 102 (5) |
| C55 | C52 | C53 | C54 | 179.4 (8) |
| C55 | C56 | C57 | C58 | 0.7 (14) |
| C56 | C55 | C60 | F4 | 179.5 (8) |
| C56 | C55 | C60 | C59 | 0.0 (14) |
| C56 | C57 | C58 | C61 | 177.1 (8) |
| C56 | C57 | C58 | C59 | −1.2 (14) |
| C57 | C58 | C59 | C60 | 1.2 (13) |
| C58 | C61 | C62 | C63 | −108.3 (8) |
| C58 | C61 | C63 | C62 | 106.3 (8) |
| C58 | C61 | C64 | O7 | 3.4 (10) |
| C58 | C61 | C64 | O8 | −177.7 (7) |
| C58 | C59 | C60 | F4 | 179.9 (7) |
| C58 | C59 | C60 | C55 | −0.5 (13) |
| C60 | C55 | C56 | C57 | 0.0 (14) |
| C55' | C52 | C53 | C54 | 175 (3) |
| C55' | C56' | C57' | C58' | −6 (6) |
| C56' | C55' | C60' | F4' | 178 (2) |
| C56' | C55' | C60' | C59' | 1 (5) |
| C56' | C57' | C58' | C61 | −167 (3) |
| C56' | C57' | C58' | C59' | 11 (7) |
| C57' | C58' | C59' | C60' | −10 (7) |
| C58' | C61 | C62 | C63 | −115 (3) |
| C58' | C61 | C63 | C62 | 110 (3) |
| C58' | C61 | C64 | O7 | 5.1 (17) |
| C58' | C61 | C64 | O8 | −176.0 (16) |
| C58' | C59' | C60' | F4' | −173 (4) |
| C58' | C59' | C60' | C55' | 5 (7) |
| C60' | C55' | C56' | C57' | −1 (3) |
| N1 | C65 | C66 | C67 | 0.5 (12) |
| C65 | N1 | C69 | C68 | 2.0 (10) |
| C65 | C66 | C67 | C68 | 0.4 (11) |
| C66 | C67 | C68 | C69 | −0.1 (11) |
| C66 | C67 | C68 | C70 | −177.1 (7) |
| C67 | C68 | C69 | N1 | −1.2 (11) |
| C67 | C68 | C70 | O9 | 23.3 (11) |
| C67 | C68 | C70 | N2 | −157.1 (7) |
| C69 | N1 | C65 | C66 | −1.7 (11) |
| C69 | C68 | C70 | O9 | −153.6 (7) |
| C69 | C68 | C70 | N2 | 26.0 (10) |
| C70 | C68 | C69 | N1 | 175.8 (7) |
| N3 | C71 | C72 | C73 | 1.8 (12) |
| C71 | N3 | C75 | C74 | −0.1 (11) |
| C71 | C72 | C73 | C74 | −1.4 (11) |
| C72 | C73 | C74 | C75 | 0.3 (11) |
| C72 | C73 | C74 | C76 | 177.0 (7) |
| C73 | C74 | C75 | N3 | 0.4 (11) |
| C73 | C74 | C76 | O10 | −22.4 (10) |
| C73 | C74 | C76 | N4 | 157.2 (7) |
| C75 | N3 | C71 | C72 | −1.1 (11) |
| C75 | C74 | C76 | O10 | 154.2 (7) |
| C75 | C74 | C76 | N4 | −26.2 (10) |
| C76 | C74 | C75 | N3 | −176.2 (7) |
| N5 | C77 | C78 | C79 | 0.5 (11) |
| C77 | N5 | C81 | C80 | 1.5 (11) |
| C77 | C78 | C79 | C80 | 0.4 (11) |
| C78 | C79 | C80 | C81 | −0.3 (10) |
| C78 | C79 | C80 | C82 | −179.5 (7) |
| C79 | C80 | C81 | N5 | −0.6 (11) |
| C79 | C80 | C82 | O11 | −151.7 (7) |
| C79 | C80 | C82 | N6 | 26.6 (11) |
| C81 | N5 | C77 | C78 | −1.4 (11) |
| C81 | C80 | C82 | O11 | 29.2 (10) |
| C81 | C80 | C82 | N6 | −152.5 (7) |
| C82 | C80 | C81 | N5 | 178.6 (7) |
| N7 | C83 | C84 | C85 | 0.7 (11) |
| C83 | N7 | C87 | C86 | 0.3 (11) |
| C83 | C84 | C85 | C86 | 0.4 (11) |
| C84 | C85 | C86 | C87 | −1.1 (10) |
| C84 | C85 | C86 | C88 | 179.5 (7) |
| C85 | C86 | C87 | N7 | 0.8 (11) |
| C85 | C86 | C88 | O12 | −152.7 (7) |
| C85 | C86 | C88 | N8 | 28.7 (11) |
| C87 | N7 | C83 | C84 | −1.0 (11) |

TABLE A6-continued

Torsion Angles for CSPNCT-supercell.

| A | B | C | D | Angle/° |
|---|---|---|---|---|
| C87 | C86 | C88 | O12 | 27.9 (10) |
| C87 | C86 | C88 | N8 | −150.7 (7) |
| C88 | C86 | C87 | N7 | −179.8 (7) |

TABLE A7

Hydrogen Atom Coordinates (Å × 10⁴) and Isotropic Displacement Parameters (Å² × 10³) for CSPNCT-supercell.

| Atom | x | y | z | U(eq) |
|---|---|---|---|---|
| H1 | 10860.44 | 7939.64 | 8296.74 | 44 |
| H3 | 6272.84 | 10584.72 | 6454.74 | 33 |
| H5 | 9981.16 | 8405.73 | 5970.16 | 39 |
| H6 | 9590.88 | 9423.99 | 5361.48 | 48 |
| H14A | 10201.63 | 5086.42 | 7409.55 | 47 |
| H14B | 10857.67 | 4867.38 | 7888.39 | 47 |
| H15A | 8498.8 | 5820.18 | 8182.24 | 47 |
| H15B | 7842.89 | 6039.19 | 7703.5 | 47 |
| H8 | 10670.69 | 8144.99 | 6617.07 | 35 |
| H9 | 11213.54 | 6976.22 | 7182.27 | 35 |
| H11 | 7035.56 | 8032.5 | 7489.51 | 33 |
| H8' | 9906.73 | 7223.02 | 6391.95 | 35 |
| H9' | 10641.78 | 6148.72 | 6978.64 | 35 |
| H11' | 7634.84 | 8605.14 | 7642.13 | 33 |
| H3A | 5912.1 | 7883.64 | 8295.62 | 43 |
| H19 | 1006.66 | 10201.95 | 6446.36 | 35 |
| H21 | 5141.95 | 8638.5 | 6090.24 | 41 |
| H22 | 4719.52 | 9751.07 | 5501.47 | 50 |
| H30A | 5267.2 | 4900.41 | 7474.37 | 41 |
| H30B | 5969.35 | 4743.82 | 7946.63 | 41 |
| H31A | 3647.76 | 5702.42 | 8252.16 | 39 |
| H31B | 2945.8 | 5858.96 | 7780.03 | 39 |
| H24 | 5097.7 | 7256.63 | 6456.46 | 35 |
| H25 | 5692.9 | 6108.85 | 7024.71 | 35 |
| H27 | 2529.08 | 8417.35 | 7688.14 | 33 |
| H24' | 5612.5 | 8028.35 | 6642.1 | 35 |
| H25' | 6217.29 | 7154.55 | 7277.31 | 35 |
| H27' | 2078.88 | 7833.54 | 7523.06 | 33 |
| H5A | 4442.71 | 7080.88 | 1717.9 | 46 |
| H35 | 1951.4 | 4476.07 | 3510.4 | 36 |
| H37 | 3493.79 | 6604.22 | 4019.43 | 40 |
| H38 | 4024.11 | 5529.78 | 4620.11 | 47 |
| H46A | 6.16 | 9214.52 | 1771.63 | 42 |
| H46B | −600.78 | 9045.71 | 2243.4 | 42 |
| H47A | 764.23 | 9973.07 | 2552.69 | 42 |
| H47B | 1371.12 | 10141.86 | 2080.96 | 42 |
| H40 | 4089.19 | 6831.64 | 3363.98 | 35 |
| H41 | 3655.9 | 7962.32 | 2787.33 | 35 |
| H43 | 331.66 | 7135.87 | 2503.58 | 33 |
| H40' | 2859.76 | 7669.53 | 3559.4 | 35 |
| H41' | 2517.1 | 8745.21 | 2967.91 | 35 |
| H43' | 1358.95 | 6517.86 | 2356.11 | 33 |
| H7 | 698.54 | 2897.91 | 8268.8 | 43 |
| H51 | 3424.79 | 5248.93 | 6416.94 | 34 |
| H53 | 1070.73 | 3558.45 | 6050.83 | 36 |
| H54 | 396.15 | 4681.4 | 5471.43 | 45 |
| H62A | 5750.25 | 903.64 | 7750.75 | 40 |
| H62B | 5160.67 | 790.97 | 8230.93 | 40 |
| H63A | 3840.14 | −204.35 | 7959.14 | 41 |
| H63B | 4429.68 | −91.69 | 7479.17 | 41 |
| H56 | 2562.53 | 2180.24 | 6412.15 | 35 |
| H57 | 3011.12 | 1066.66 | 7006.33 | 35 |
| H59 | 3434.29 | 3523.55 | 7671.9 | 33 |
| H56' | 1227.83 | 2818.55 | 6574.28 | 35 |
| H57' | 1498.44 | 1922.33 | 7216.01 | 35 |
| H59' | 4274.47 | 3202.37 | 7564.42 | 33 |
| H2A | 6254.28 | 4860.77 | 155.68 | 37 |
| H2B | 7453.37 | 4120.82 | 428.06 | 37 |
| H65 | 7977.14 | 423.02 | 1453.78 | 36 |
| H66 | 6334.3 | 366.58 | 983.76 | 37 |
| H67 | 5384.91 | 1820.2 | 507.33 | 32 |
| H69 | 7824.57 | 3287.07 | 997.51 | 27 |
| H4A | 8745.89 | 5135.82 | 9843.98 | 36 |
| H4B | 7572.57 | 5851.88 | 9558.81 | 36 |
| H71 | 7067.02 | 9524.79 | 8527.35 | 38 |
| H72 | 8617 | 9662.33 | 9023.26 | 36 |
| H73 | 9578.57 | 8208.5 | 9505.51 | 36 |
| H75 | 7237.79 | 6677.64 | 8991.13 | 32 |
| H6A | 3588.04 | 517.61 | 9995.33 | 38 |
| H6B | 2395.59 | 1342.61 | 9742.54 | 38 |
| H77 | 2602.47 | 4528.34 | 8524.68 | 35 |
| H78 | 949.74 | 4512.81 | 9024.77 | 34 |
| H79 | 1586.41 | 3134.16 | 9534.77 | 36 |
| H81 | 5516.48 | 1883.89 | 9007.6 | 31 |
| H8A | 8551.53 | 524.98 | 9984.24 | 36 |
| H8B | 7382.21 | 1392.96 | 9737.68 | 36 |
| H83 | 7761.63 | 4478.42 | 8497.54 | 37 |
| H84 | 6089.43 | 4518.53 | 8999.82 | 37 |
| H85 | 6671.06 | 3152.73 | 9520.66 | 33 |
| H87 | 10582.56 | 1783.27 | 8992.33 | 31 |

TABLE 8

Atomic Occupancy for CSPNCT-supercell.

| Atom | Occupancy |
|---|---|
| F1 | 0.894(3) |
| H8 | 0.894(3) |
| C10 | 0.894(3) |
| C12 | 0.894(3) |
| C8' | 0.106(3) |
| H9' | 0.106(3) |
| H11' | 0.106(3) |
| C23 | 0.894(3) |
| C25 | 0.894(3) |
| C27 | 0.894(3) |
| F2' | 0.106(3) |
| H24' | 0.106(3) |
| C26' | 0.106(3) |
| C28' | 0.106(3) |
| C40 | 0.894(3) |
| H41 | 0.894(3) |
| H43 | 0.894(3) |
| C39' | 0.106(3) |
| C41' | 0.106(3) |
| C43' | 0.106(3) |
| F4 | 0.894(3) |
| H56 | 0.894(3) |
| C58 | 0.894(3) |
| C60 | 0.894(3) |
| C56' | 0.106(3) |
| H57' | 0.106(3) |
| H59' | 0.106(3) |
| C7 | 0.894(3) |
| C9 | 0.894(3) |
| C11 | 0.894(3) |
| F1' | 0.106(3) |
| H8' | 0.106(3) |
| C10' | 0.106(3) |
| C12' | 0.106(3) |
| C24 | 0.894(3) |
| H25 | 0.894(3) |
| H27 | 0.894(3) |
| C23' | 0.106(3) |
| C25' | 0.106(3) |
| C27' | 0.106(3) |
| F3 | 0.894(3) |
| H40 | 0.894(3) |
| C42 | 0.894(3) |
| C44 | 0.894(3) |
| C40' | 0.106(3) |
| H41' | 0.106(3) |

TABLE 8-continued

Atomic Occupancy for CSPNCT-supercell.

| Atom | Occupancy |
|------|-----------|
| H43' | 0.106(3) |
| C55  | 0.894(3) |
| C57  | 0.894(3) |
| C59  | 0.894(3) |
| F4'  | 0.106(3) |
| H56' | 0.106(3) |
| C58' | 0.106(3) |
| C60' | 0.106(3) |
| C8   | 0.894(3) |
| H9   | 0.894(3) |
| H11  | 0.894(3) |
| C7'  | 0.106(3) |
| C9'  | 0.106(3) |
| C11' | 0.106(3) |
| F2   | 0.894(3) |
| H24  | 0.894(3) |
| C26  | 0.894(3) |
| C28  | 0.894(3) |
| C24' | 0.106(3) |
| H25' | 0.106(3) |
| H27' | 0.106(3) |
| C39  | 0.894(3) |
| C41  | 0.894(3) |
| C43  | 0.894(3) |
| F3'  | 0.106(3) |
| H40' | 0.106(3) |
| C42' | 0.106(3) |
| C44' | 0.106(3) |
| C56  | 0.894(3) |
| H57  | 0.894(3) |
| H59  | 0.894(3) |
| C55' | 0.106(3) |
| C57' | 0.106(3) |
| C59' | 0.106(3) |

Example 8

The DSC for CSPNCT displayed an endothermic event with an onset at 114.0° C., a peak maximum of 116.7° C., and a ΔH of 60.5 J/g with an endset at 121.1° C. This event was followed by a broader endothermic event with a peak maximum at 159.1° C. and an endset at 183.2° C. Degradation appears to start occurring around 135° C. by TGA. Mass loss from ambient temperature to 105.0° C. was 0.3%, and to 122.0° C. was 0.6%, and to 183.2° C. was 7.2% (total mass loss).

Figure 5:
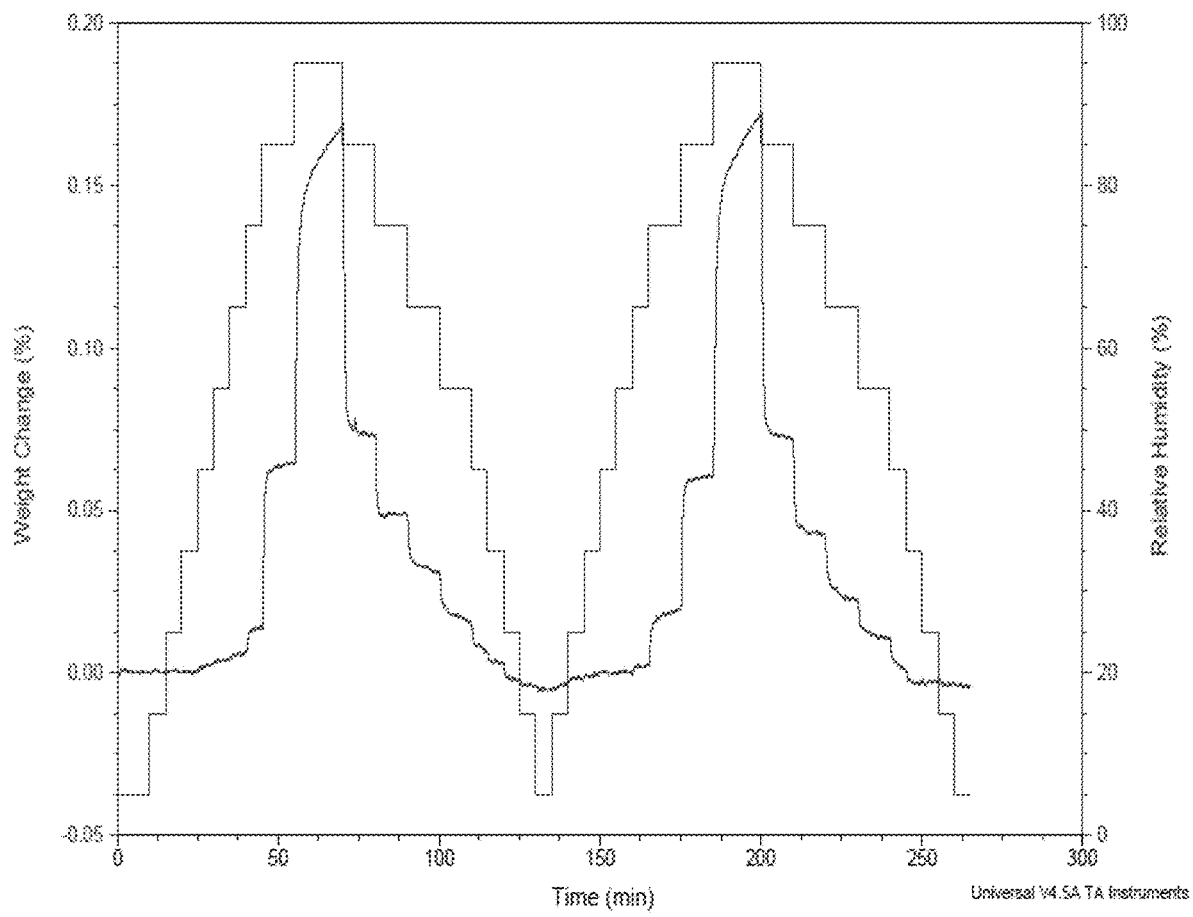
FIG. 5 is DVS kinetic plot for CSPNCT (5-95% RH, 25° C.).
Figure 6:
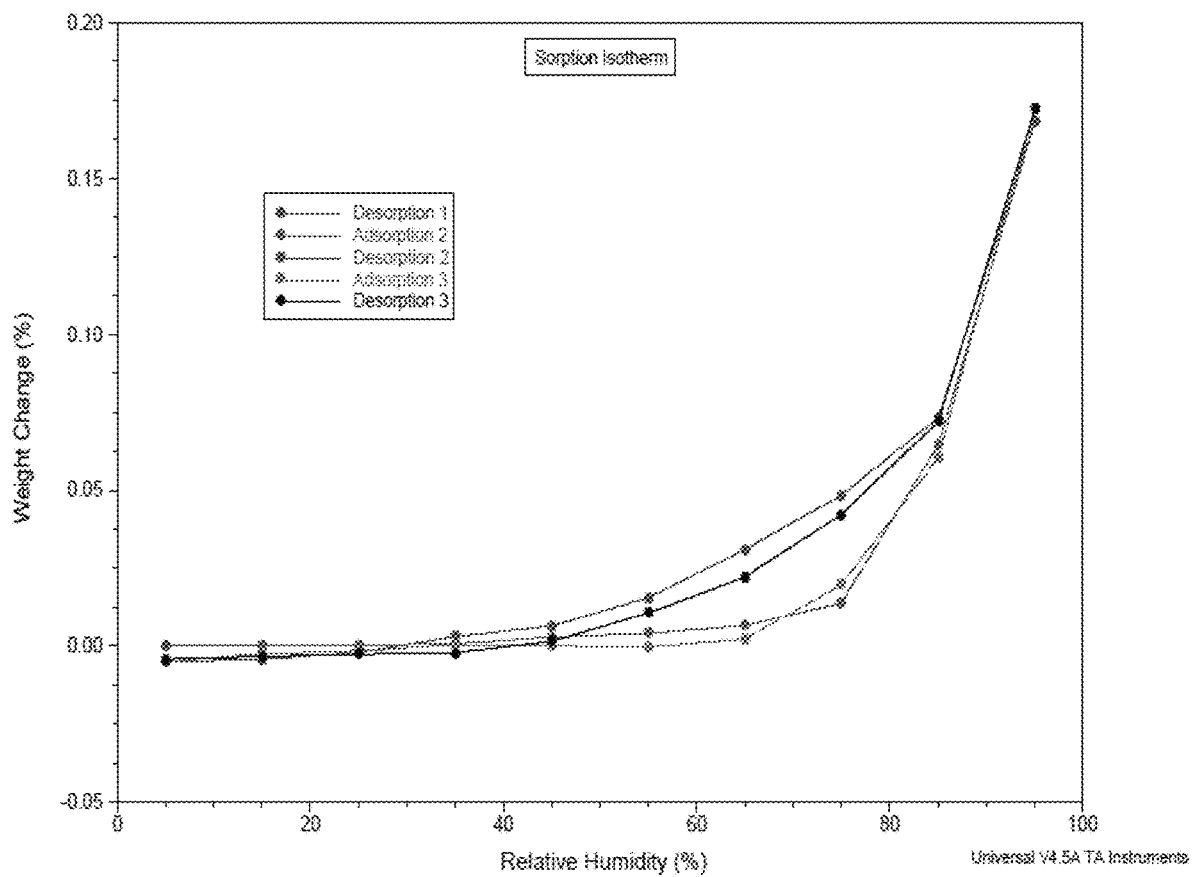
FIG. 6 is DVS isothermal plot for CSPNCT (5-95% RH, 25° C.).

Results from a completed DVS experiment for CSPNCT (R23809-012-001) from 5-95% RH are presented in FIGS. 5 and 6 for the kinetic and isothermal DVS curves, respectively and in Table 11.

TABLE 11

R23809-DVS-012-001, CSPNCT

| Cycle 1 of 2 | RH Start (%) | RH Stop (%) | Mass Change (%) | Cycle 2 of 2 | RH Start (%) | RH Stop (%) | Mass Change (%) |
|---|---|---|---|---|---|---|---|
| Adsorption | 5 | 95 | 0.17 | Adsorption | 5 | 95 | 0.18 |
| Desorption | 95 | 5 | -0.17 | Desorption | 95 | 5 | -0.17 |

The average water sorbed or desorbed for this material is 0.17±0.00% between 5-95% RH. This material should be considered non-hygroscopic at 95% RH (<0.2%, Ph. Eur. 9.0).

Figure 7:
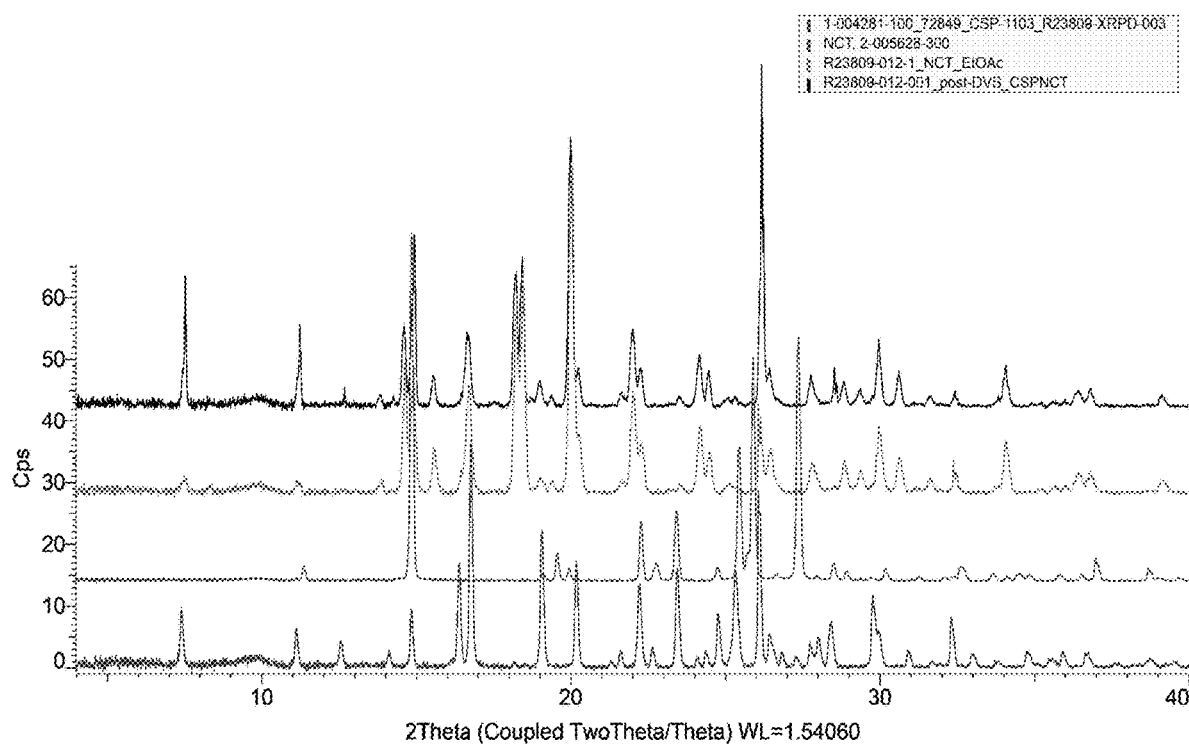
FIG. 7 is XRPD for pre-exposed (second from top) and post-exposed (top) DVS sample of CSPNCT (5-95% RH, 25° C.).

The XRPD results for the preexposed and post-exposed materials are presented in FIG. 7 and are comparable to each other. There were no solid state form changes for either CSP, CSPNCT, and NCT after exposure to two DVS sorption/desorption cycles. These conclusions were based on the XRPD patterns of the post-exposed materials having comparable XRPD patterns to the pre-exposed materials.

Table 12A, 12B and 12C display the tabular results for the water vapor sorption and desorption of CSP, CSPNCT, and NCT, respectively.

TABLE 12A

R23809-DVS-003, CSP-1103, lot N1200856 (1-004281-100, 72849)

| Cycle 1 of 2 | RH Start (%) | RH Stop (%) | Mass Change (%) | Cycle 2 of 2 | RH Start (%) | RH Stop (%) | Mass Change (%) |
|---|---|---|---|---|---|---|---|
| Adsorption | 5 | 95 | 1.10 | Adsorption | 5 | 95 | 1.13 |
| Desorption | 95 | 5 | -1.11 | Desorption | 95 | 5 | -1.13 |

TABLE 12B

R23809-DVS-012-001, CSPNCT

| Cycle 1 of 2 | RH Start (%) | RH Stop (%) | Mass Change (%) | Cycle 2 of 2 | RH Start (%) | RH Stop (%) | Mass Change (%) |
|---|---|---|---|---|---|---|---|
| Adsorption | 5 | 95 | 0.17 | Adsorption | 5 | 95 | 0.18 |
| Desorption | 95 | 5 | -0.17 | Desorption | 95 | 5 | -0.17 |

TABLE 12C

R23809-DVS-NCT

| Cycle 1 of 2 | RH Start (%) | RH Stop (%) | Mass Change (%) | Cycle 2 of 2 | RH Start (%) | RH Stop (%) | Mass Change (%) |
|---|---|---|---|---|---|---|---|
| Adsorption | 5 | 95 | 1.11 | Adsorption | 5 | 95 | 1.18 |
| Desorption | 95 | 5 | -1.11 | Desorption | 95 | 5 | -1.18 |

Figure 8A:
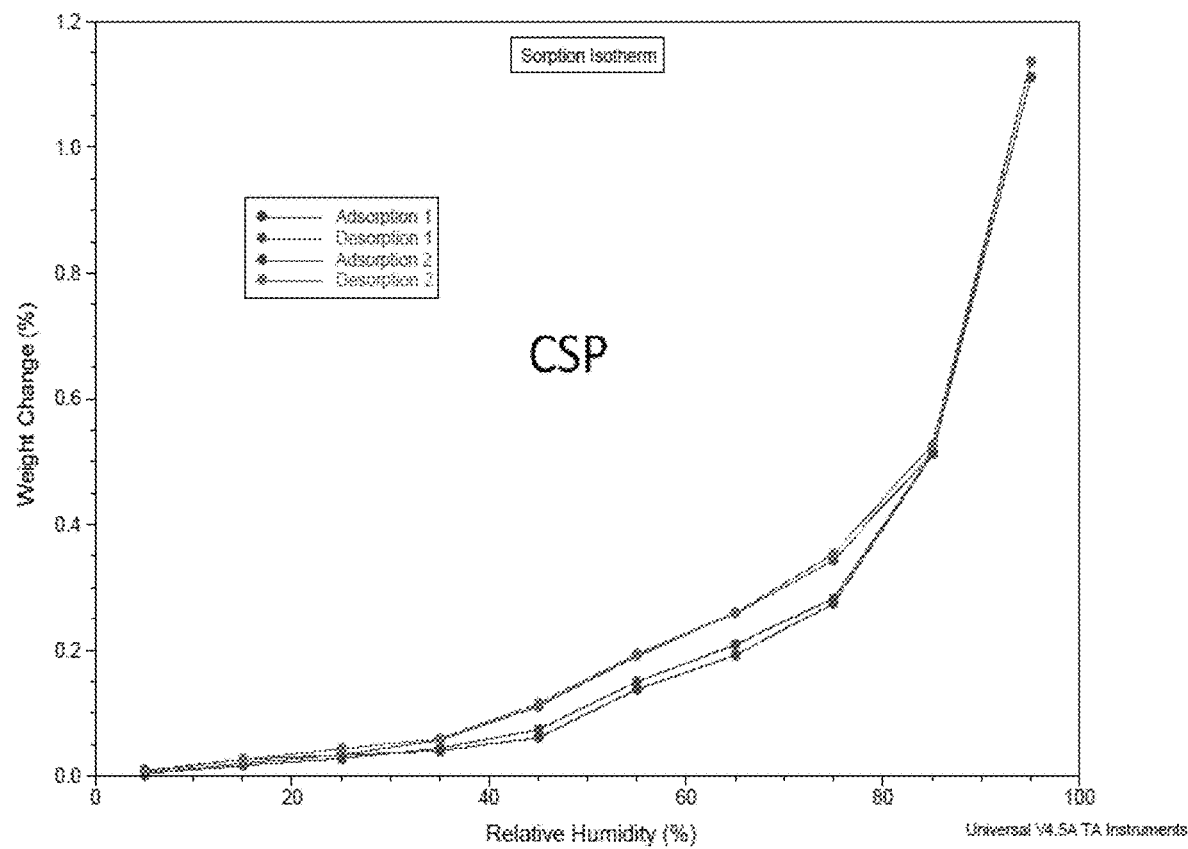
FIGS. 8A-8C depict isotherms for the water vapor sorption and desorption of CSP, CSPNCT, and NCT, respectively. All the isotherms have the same scales for the Percentage Weight Change (y-axis) and the Percentage Relative Humidity (x-axis) for comparative purposes.
Figure 8B:
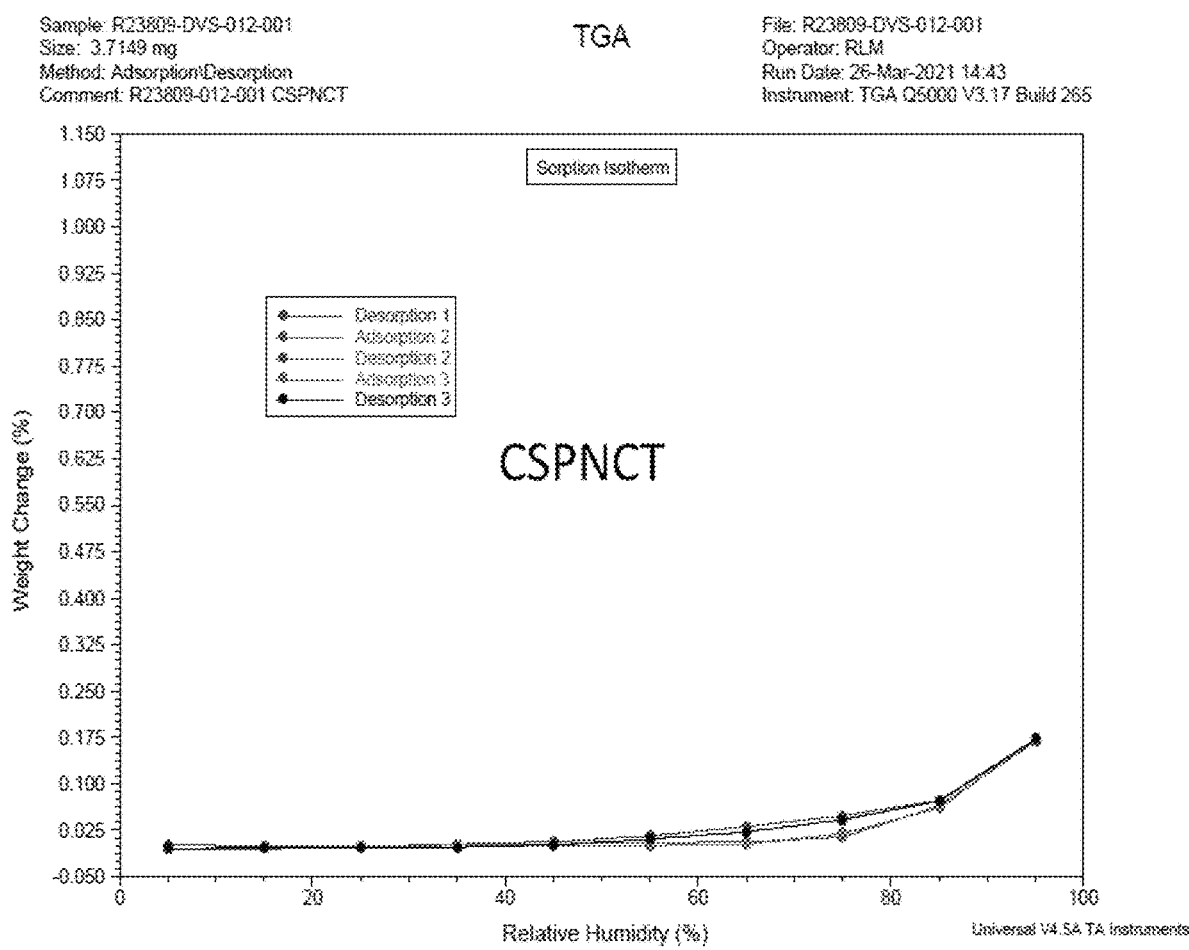
Figure 8C:
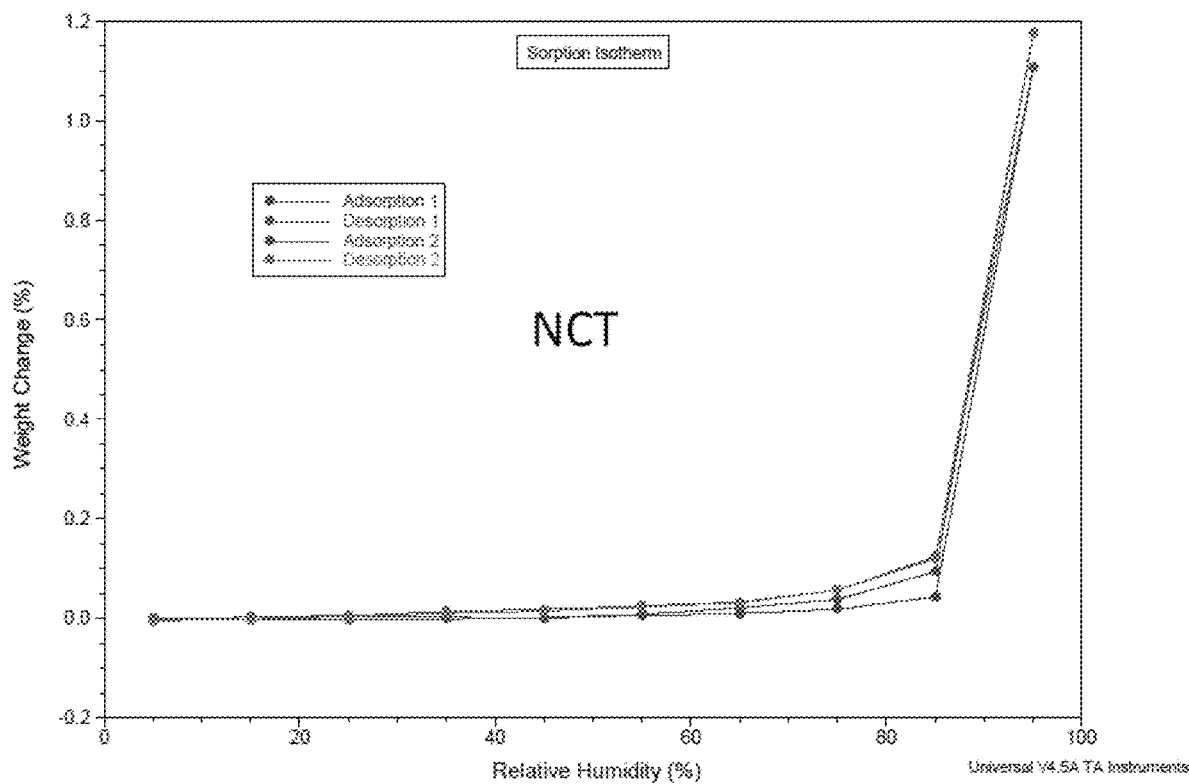
Figure 9A:
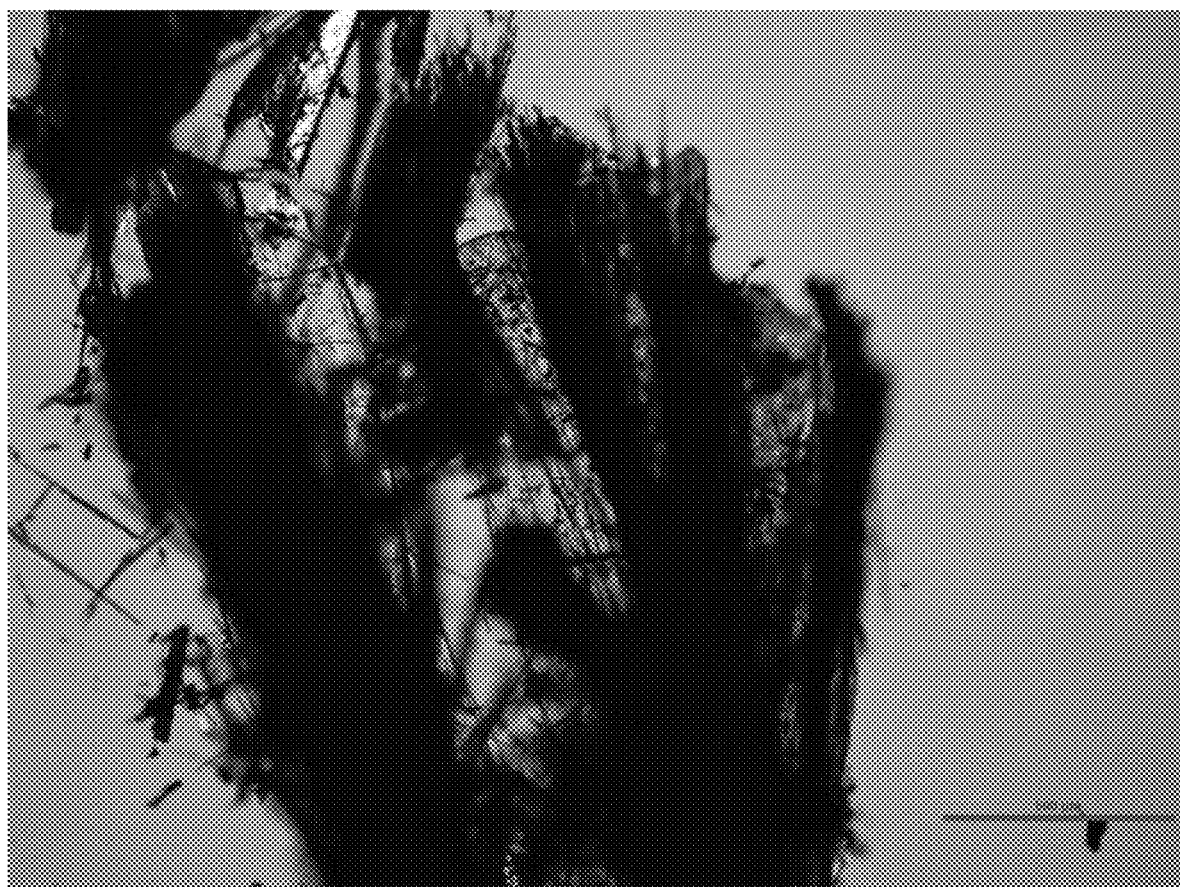
FIGS. 9A-9D are photomicrographs at various magnifications of CSPNCT.
Figure 9B:
Figure 9C:
Figure 9D:
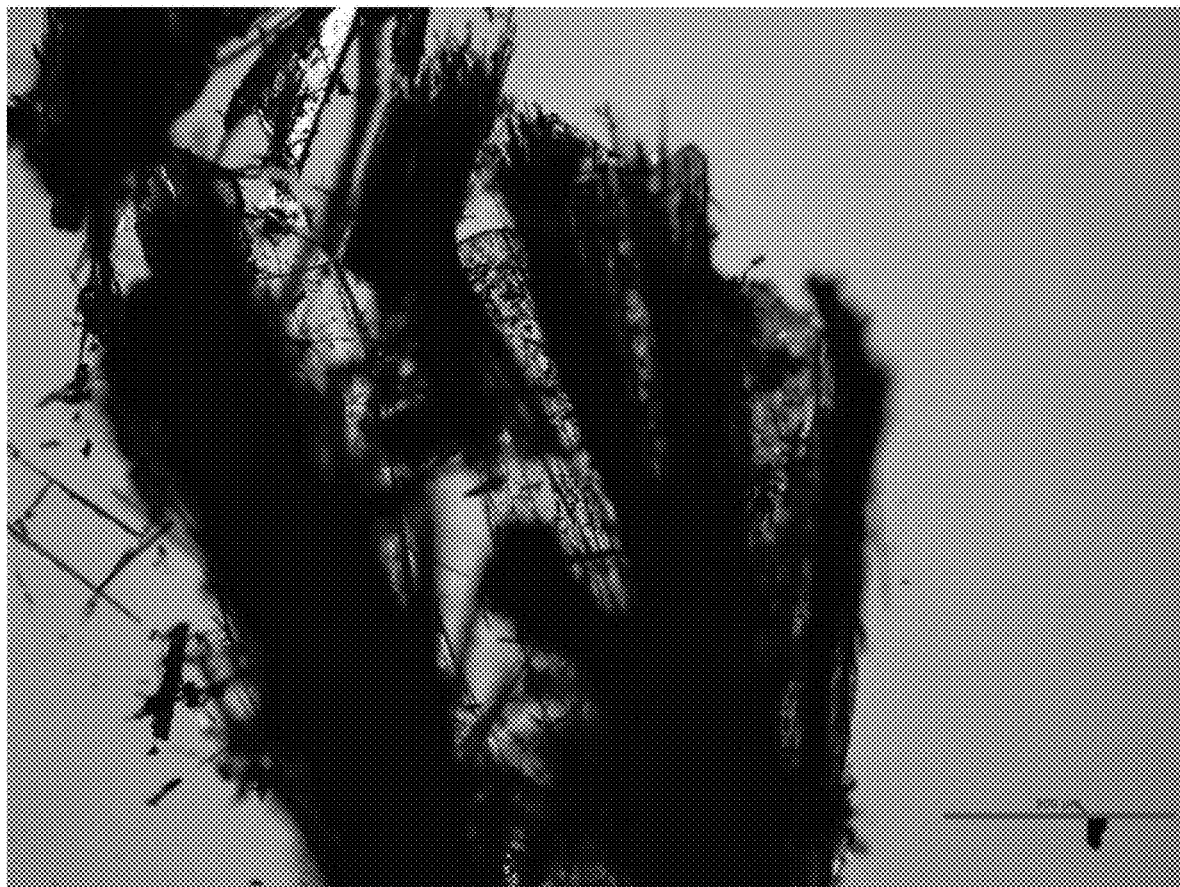

FIGS. 8A, 8B and 8C display the isotherms for the water vapor sorption and desorption of CSP, CSPNCT, and NCT, respectively.

The non-hygroscopicity of CSPNCT is a distinct advantage over CSP-1103 alone, based on the DVS results.

Example 9

The HPLC assay for CSP-1103 and Coformers was developed.
Method Conditions:
  Column: Agilent Poroshell 120 EC-C18, 4.6×50 mm, 2.7 μm
  Mobile Phase A: 0.05% TFA in Water
  Mobile Phase B: 0.05% TFA in ACN
  Flow Rate: 1.0 mL/min
  Profile: Gradient (See Table 13A below)
  Column Temp: 40° C.
  UV Detection: 262 nm (Bandwidth=4 nm; Reference=OFF)
    220 nm (Bandwidth=4 nm; Reference=OFF)
  Concentration: 0.03 mg/L
  Sample Diluent: 0.05% TFA in 50/50 (v/v) Water/ACN
  Injection Volume: 2.0 μL Needle Wash Mode: Vial rinse
Needle Wash Solvent: Diluent
Run Time: 15 minutes.

TABLE 13A

| Time (min) | % Mobile Phase A | % Mobile Phase B |
|---|---|---|
| 0.0 | 90 | 10 |
| 2.0 | 90 | 10 |
| 7.0 | 10 | 90 |

TABLE 13A-continued

| Time (min) | % Mobile Phase A | % Mobile Phase B |
|---|---|---|
| 10.0 | 10 | 90 |
| 10.1 | 90 | 10 |
| 15.0 | 90 | 10 |

Expected retention times are provided in Table 13B.

TABLE 13B

| Compound | Retention Time (min) | Relative Retention Time |
|---|---|---|
| Ascorbic Acid | 0.54 | 0.07 |
| Nicotinamide | 0.56 | 0.07 |
| Phenylalanine | 1.36 | 0.18 |
| Saccharin | 1.40 | 0.18 |
| Caffeine | 2.02 | 0.27 |
| Caffeic Acid | 2.48 | 0.33 |
| Vanillin | 3.88 | 0.51 |
| Benzoic Acid | 4.71 | 0.62 |
| CSP-1103 | 7.59 | 1.00 |

Glutamic acid was not detected. Citric acid elutes at the injection void with very poor response. All other components were detected with reasonable response levels at 262 nm. Two pairs of unresolved coformers existed: nicotinamide and ascorbic acid, and phenylalanine and saccharin.

Method linearity was demonstrated for CSP-1103 from 3-300 µg/mL. A mixture of coformers was prepared and stored at 4° C. to be used for future RT marking of the components.

Example 10

A second set of coformers were investigated, focusing on the acid-acid homosynthon supramolecular structural interaction. Two screens were attempted: (1) saturated solution cocrystallization and (2) solvent-assisted grinding cocrystallization. The results are presented in Table 14.

TABLE 14

| | Saturated Solution Cocrystallization | | | | | | |
|---|---|---|---|---|---|---|---|
| R23809-015-### | Solvent (50 µL) | CSP (mmol) | Coformer | MW (mg/mmol) | mmol | Designation | XRPD Comments |
| 001 | ethyl acetate: ethanol 1:1 | 0.10 | Succinic Acid | 118.09 | NA | CSPSCA | CSP & SCA |
| 002 | | 0.10 | p-Coumaric Acid | 164.16 | NA | CSPCOU | CSP & COU |
| 003 | | 0.10 | Hippuric Acid | 179.18 | NA | CSPHPA | CSP & HPA |
| 004 | | 0.10 | Fumaric Acid | 116.07 | NA | CSPFMA | CSP & FMA |
| | Solvent Assisted Grinding Cocrystallization | | | | | | |
| R23809-015-### | Solvent | CSP (mmol) | Coformer | MW (mg/mmol) | mmol | Designation | XRPD Comments |
| 005 | ethyl acetate: ethanol 1:1 | 0.11 | Succinic Acid | 118.09 | 0.12 | CSPSCA | CSP & SCA |
| 006 | | 0.11 | p-Coumaric Acid | 164.16 | 0.11 | CSPCOU | CSP & COU |
| 007 | | 0.11 | Hippuric Acid | 179.18 | 0.12 | CSPHPA | CSP & HPA |
| 008 | | 0.11 | Fumaric Acid | 116.07 | 0.11 | CSPFMA | CSP & FMA |

No novel co-crystals were discovered through either of these screens.

All publications, patent applications, patents, and other references mentioned herein are incorporated by reference. The references cited herein are not admitted being prior art to the claimed disclosure. In the case of conflict, the present specification, including definitions, will control.

What is claimed is:

1. A method of treating Alzheimer's disease in a human in need thereof, comprising administering a therapeutically effective dosage regimen of a co-crystal comprising itanapraced and nicotinamide to the human,
   wherein the co-crystal has an X-ray Powder Diffraction Pattern (XRPD) with specific peaks, expressed in 2θ produced from a Cu radiation source ($\lambda=1.54$ Å after Ni filtering), at about 14.63°; 14.90°; 15.56°; 16.71°; 18.24°; 18.46°, 20.03°; 20.27°; 22.01°, 22.27°; 24.17°; 24.47°; 26.14°; 26.47°; 27.83°; 28.85°; 29.97°; 30.64°; 32.42°; 34.07°; and 39.14°, all +/−0.2 degrees 2θ.

2. The method of claim 1, wherein a stoichiometric ratio of itanapraced to nicotinamide is from about 0:8:1.2 to about 1.2:0.8.

3. The method of claim 1, wherein the X-ray Powder Diffraction Pattern (XRPD) is substantially the same as the X-ray Powder Diffraction Pattern (XRPD) shown in FIG. 3A.

4. The method of claim 1, wherein the co-crystal is administered orally.

5. The method of claim 4, wherein the co-crystal is administered in a solid dosage form.

6. The method of claim 5, wherein the solid dosage form is a tablet.

7. The method of claim 5, wherein the solid dosage form is formulated as an immediate release formulation.

8. The method of claim 4, wherein the co-crystal is administered at a dose from about 3 mg/day to about 3000 mg/day.

9. The method of claim 8, wherein the dose is from about 5 mg/day to about 2000 mg/day.

10. The method of claim 1, wherein the co-crystal is administered from 1 to 4 times per day.

* * * * *